US010668094B2

(12) United States Patent
Karlish et al.

(10) Patent No.: US 10,668,094 B2
(45) Date of Patent: Jun. 2, 2020

(54) SELECTIVE INHIBITORS OF ALPHA2-CONTAINING ISOFORMS OF NA,K-ATPASE AND USE THEREOF FOR REDUCTION OF INTRAOCULAR PRESSURE

(71) Applicant: Yeda Research and Development Co. Ltd., Rehovot (IL)

(72) Inventors: Steven J. D. Karlish, Rehovot (IL); Adriana Katz, Rehovot (IL); Daniel M. Tal, Rehovot (IL); Arie Marcovich, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 115 days.

(21) Appl. No.: 15/745,441

(22) PCT Filed: Jul. 19, 2016

(86) PCT No.: PCT/IL2016/050785
§ 371 (c)(1),
(2) Date: Jan. 17, 2018

(87) PCT Pub. No.: WO2017/013648
PCT Pub. Date: Jan. 26, 2017

(65) Prior Publication Data
US 2018/0207189 A1    Jul. 26, 2018

Related U.S. Application Data

(63) Continuation-in-part of application No. PCT/IL2015/050741, filed on Jul. 19, 2015.

(60) Provisional application No. 62/302,226, filed on Mar. 2, 2016.

(51) Int. Cl.
| | |
|---|---|
| *C07H 17/00* | (2006.01) |
| *C07J 43/00* | (2006.01) |
| *C07J 19/00* | (2006.01) |
| *A61K 31/7052* | (2006.01) |
| *A61P 27/06* | (2006.01) |
| *A61P 9/00* | (2006.01) |

(52) U.S. Cl.
CPC ............ *A61K 31/7052* (2013.01); *A61P 9/00* (2018.01); *A61P 27/06* (2018.01); *C07H 17/00* (2013.01); *C07J 43/003* (2013.01); *C07J 19/005* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling et al. | |
| 3,879,262 A | 4/1975 | Schuurs et al. | |
| 3,901,654 A | 8/1975 | Gross | |
| 3,925,355 A * | 12/1975 | Piasio ................. | C07J 43/003 536/6.2 |
| 3,935,074 A | 1/1976 | Rubinstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,190,496 A | 2/1980 | Rubenstein et al. | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 5,972,630 A | 10/1999 | Cromer et al. | |
| 9,938,316 B2 * | 4/2018 | Karlish ................. | C07J 43/003 |
| 2003/0207431 A1 | 11/2003 | Ghoshal et al. | |
| 2004/0210044 A1 | 10/2004 | Slattum et al. | |
| 2008/0199895 A1 | 8/2008 | Karlish et al. | |
| 2016/0244479 A1 | 8/2016 | Karlish et al. | |

FOREIGN PATENT DOCUMENTS

| | | |
|---|---|---|
| DE | e 224037 | 6/1985 |
| EP | 0532187 | 3/1993 |
| FR | 2262670 | 9/1975 |
| WO | WO 98/52961 | 11/1998 |
| WO | WO 2006/044916 | 4/2006 |
| WO | WO 2007/016656 | 2/2007 |
| WO | WO 2015/029035 | 3/2015 |
| WO | WO 2017/013637 | 1/2017 |
| WO | WO 2017/013648 | 1/2017 |

OTHER PUBLICATIONS

Wolff, Manfred E. "Burger's Medicinal Chemistry, 5ed, Part I", John Wiley & Sons, 1995, pp. 975-977 (Year: 1995).*
Banker, G.S. et al, "Modern Pharmaceutics, 3ed.", Marcel Dekker, New York, 1996, p. 596 (Year: 1996).*
Adamczyk et al., Journal of Organic Chemistry, 1995, vol. 60(11), pp. 3557-3560 (Year: 1995).*
Hara et al., Journal of Labelled Compounds and Radiopharmaceuticals—1977, vol. 13(2), pp. 222-223 (Year: 1977).*
Communication Relating to the Results of the Partial International Search dated Oct. 17, 2016 From the International Searching Authority Re. Application No. PCT/IL2016/050785.
Communication Relating to the Results of the Partial International Search dated Oct. 27, 2015 From the International Searching Authority Re. Application No. PCT/IL2015/050741.

(Continued)

*Primary Examiner* — Traviss C McIntosh, III

(57) ABSTRACT

Provided herein are alpha2-selective Na,K-ATPase inhibitors and prodrugs thereof, characterized by having a cyclic moiety attached to a digoxin or digitoxin derivative, as well as uses thereof in lowering intraocular pressure and in treating glaucoma and heart conditions.

17 Claims, 4 Drawing Sheets

Specification includes a Sequence Listing.

(56) References Cited

OTHER PUBLICATIONS

International Preliminary Report on Patentability dated Feb. 1, 2018 From the International Bureau of WIPO Re. Application No. PCT/IL2015/050741. (16 Pages).
International Preliminary Report on Patentability dated Feb. 1, 2018 From the International Bureau of WIPO Re. Application No. PCT/IL2016/050785. (15 Pages).
International Preliminary Report on Patentability dated Mar. 10, 2016 From the International Bureau of WIPO Re. Application No. PCT/IL2014/050773.
International Search Report and the Written Opinion dated Nov. 18, 2014 From the International Searching Authority Re. Application No. PCT/IL2014/050773.
International Search Report and the Written Opinion dated Jan. 22, 2016 From the International Searching Authority Re. Application No. PCT/IL2015/050741.
International Search Report and Written Opinion dated Dec. 19, 2016 From the International Searching Authority Re. Application No. PCT/IL2016/050785. (23 Pages).
Notice of Allowance dated Jan. 11, 2018 From the US Patent and Trademark Office Re. U.S. Appl. No. 14/913,366. (7 pages).
Office Action and Search Report dated Oct. 17, 2016 From the State Intellectual Property Office of the People's Republic of China Re. Application No. 201480059614.5 and Its Translation Into English.
Office Action dated May 2, 2017 From the State Intellectual Property Office of the People's Republic of China Re. Application No. 201480059614.5 and Its Translation Into English. (10 Pages).
Official Action dated Dec. 1, 2009 From the US Patent and Trademark Office Re. U.S. Appl. No. 11/905,833.
Official Action dated Apr. 2, 2010 From the US Patent and Trademark Office Re. U.S. Appl. No. 11/905,833.
Official Action dated Jul. 14, 2017 From the US Patent and Trademark Office Re. U.S. Appl. No. 14/913,366.(28 Pages).
Restriction Official Action dated Apr. 5, 2017 From the US Patent and Trademark Office Re. U.S. Appl. No. 14/913,366. (12 pages).
Supplementary European Search Report and the European Search Opinion dated Mar. 3, 2017 From the European Patent Office Re. Application No. 14839412.5. (10 Pages).
Adamczyk et al. "Digoxin Dialdehyde Reductive Aminations. Structure Proof of the Perhydro-1,4-Oxazepine Product", Steroids, XP004026467, 60(11): 753-758, Nov. 1, 1995. Compound 3, Preparation Thereof in Scheme 1, p. 754, 1st col.
Adamczyk et al. "Unexpectedly Facile Hydrolysis of Digoxin Esters. The Importance of Appropriate Controls in Lipase-Mediated Hydrolysis", The Journal of Organic Chemistry, XP055221120, 60(11): 3557-3560, Jun. 1, 1995. Table 1, Compounds 7a-7e, Preparation Thereof on p. 3559, 1st col.
Bachrach et al. "Attachment of Drugs to Polydimethylsiloxanes", European Polymer Journal, XP024053540, 20(5): 493-500, Jan. 1984. Abstract, p. 498, col. 1, Para 1-2, Compound I.
Bers "Cardiac Excitation-Contraction Coupling", Nature, 415: 198-205, Jan. 10, 2002.
Bitter "Heterologous Gene Expression in Yeast", Methods in Enzymology, 152(Chap.70): 673-684, 1987.
Bitter et al. "Expression and Secretion Vectors for Yeast", Methods in Enzymology, 153(Chap.33): 516-544, 1987.
Cohen et al. "Purification of Na+,K+-ATPase Expressed in Pichia Pastoris Reveals an Essential Role of Phospholipid-Protein Interactions", The Journal of Biological Chemistry, 280(17); 16610-16618, Apr. 29, 2005.
Cornelius "Cholesterol Modulation of Molecular Activity of Reconstituted Shark Na+,K+-ATPase", Biochimica et Biophysica Acta, 1235: 205-212, 1995.
Cornelius "Modulation of Na,K-ATPase and Na-ATPase Activity by Phospholipids and Cholesterol. I. Steady-State Kinetics", Biochemistry, 40(30); 8842-8851, 2001.
Crambert et al. "New Molecular Determinants Controlling the Accessibility of Quabain to Its Binding Site in Human Na,K-ATPase α Isoforms", Molecular Pharmacology, 65(2): 335-341, 2004.

Crambert et al. "Transport and Pharmacological Properties of Nine Different Human Na,K-ATPase Isozymes", The Journal of Biological Chemistry, 275(3): 1976-1986, Jan. 21, 2000.
Ferraiolo et al. "Digoxin-Induced Decrease in Intraocular Pressure in the Cat", European Journal of Pharmacology, XP023839155, 55(1): 19-22, Apr. 1, 1979. Abstract.
Ferrari et al. "PST2238: A New Antihypertensive Compound That Antagonizes the Long-Term Pressor Effect of Ouabain", The Journal of Pharmacology and Experimental Therapeutics, JPET, 285(1): 83-94, 1998.
Ferrari et al. "Rostafuroxin: An Ouabain Antagonist That Corrects Renal and Vascular Na+-K+-ATPase Alterations in Ouabain and Adducin-Dependent Hypertension", American Journal of Physiology—Regulatory, Integrative and Comparative Physiology, 290: R529-R535, 2006.
Hara et al. "Heart Uptake of Radioiodine Labeled Cardenolides", Journal of Labelled Compounds and Radiopharmaceuticals, XP055348816, 13(2): 222-223, Jan. 1977. p. 222, Para 3-5, p. 223, Compound I.
Hardt et al. "Effect of Systemic Digitalis Application on Intraocular Pressure [Zum Einfluss von Systemischer Digitalis-Applikation auf den Intraocularen Druck]", Graefe's Archive for Clinical and Experimental Ophthalmology, 219(2): 76-79, Aug. 1982. Abstract.
Hartmanis et al. "Solubilization of a Membrane-Bound Diol Dehydratase With Retention of EPR G=2.02 Signal by Using 2-(N-Cyclohexylamino)Ethanesulfonic Acid Buffer", Proc. Natl. Acad. Sci. USA, 84: 76-79, Jan. 1987.
Haviv et al. "Stabilization of Na+,K+-ATPase Purified From Pichia Pastoris Membranes by Specific Interactions With Lipids", Biochemistry, 46: 12855-12867, Published on Web Oct. 16, 2007.
Hayashi et al. "Minimum Enzyme Unit for Na+/K+-ATPase is the αβ-Promoter. Determination by Low-Angle Laser Light Scattering Photometry Coupled With High-Performance Gel Chromatography for Substantially Simultaneous Measurement of ATPase Activity and Molecular Weight", Biochimica et Biophysica Acta, 983: 217-229, 1989.
Jørgensen "Purification of Na+,K+-ATPase: Enzyme Sources, Preparative Problems, and Preparation From Mammalian Kidney", Methods in Enzymology, 156(2): 29-43, 1988.
Jørgensen et al. "Role of Conserved TGDGVND-Loop in Mg2+ Binding, Phosphorylation, and Energy Transfer in Na,K-ATPase", Journal of Bioenergetics and Biomembranes, 35(5): 367-377, Oct. 2001.
Juhaszova et al. "Distinct Distribution of Different Na+ Pump α Subunit Isoforms in Plasmalemma", Annals New York Academy of Sciences, 834: 524-536, 1997.
Kapri-Pardes et al. "Stabilization of the Alpha2 Isoform of Na,K-ATPase by Mutations in a Phospholipid Binding Pocket", The Journal of Biological Chemistry, 286(50): 42888-42899, Dec. 16, 2011.
Katz et al. "Digoxin Derivatives With Enhanced Selectivity for the Alpha2 Isoform of Na,K-ATPase. Effects on Intraocular Pressure in Rabbits", The Journal of Biological Chemistry, XP055241264, 289(30): 21153-21162, Jul. 25, 2014. Abstract, p. 21153, Left col., Para 2, p. 21155, Right col., Lines 17-21, p. 21162, Right col., Para 2, p. 15, Table 1, p. 21157, Table 1, Table S1.
Katz et al. "Selectivity of Digitalis Glycosides for Isoforms of Human Na,K-ATPase", The Journal of Biological Chemistry, 285(25): 19582-19592, JBC Papers in Press Apr. 13, 2010.
Keating et al. "Potentiometric Digoxin Antibody Measurements With Antigen-Ionophore Based Membrane Electrodes", Analytical Chemistry, XP055221088, 56(4): 801-806, Apr. 1, 1984. Fig.2, Final Compound, Compounds Analyzed in Figs.3-4, Preparation.
Laursen et al. "Structures and Characterization of Digoxin- and Bufalin-Bound Na+, K+-ATPase Compared With the Ouabain-Bound Complex", Proc. Natl. Acad. Sci. USA, PNAS, 112(6): 1755-1760, Feb. 10, 2015.
Lifshitz et al. "Functional Interactions of Phospholemman (PLM) (FXYD1) With Na+,K+-ATPase. Purification of α1/β1/PLM Complexes Expressed in Pichia Pastoris", The Journal of Biological Chemistry, 281(23): 15790-15799, Jun. 9, 2006.

(56) References Cited

OTHER PUBLICATIONS

Lifshitz et al. "Purification of the Human Alpha2 Isoform of Na,K-ATPase Expressed in Pichia Pastoris. Stabilization by Lipids and FXYD1", Biochemistry, 46: 14937-14950, Published on Web Dec. 2, 2007.

Lingrel "NA,K-ATPase: Isoform Structure, Function, and Expression", Journal of Bioenergetics and Biomembrane, 24(3): 263-270, 1992.

Mishra et al. "FXYD Proteins Stabilize Na,K-ATPase. Amplificaiton of Specific Phosphatidylserine-Protein Interactions", The Journal of Biological Chemistry, 286(11): 9699-9712, Mar. 18, 2011.

Müller-Ehmsen et al. "Ouabain and Substrate Affinities of Human Na+-K+-ATPase α1β1, α2β1 and α3β1 When Expressed Separately in Yeast Cells", American Journal of Physiology—Cell Physiology, 281: C1355-C1364, Oct. 2001.

Roeder et al. "Radioiodination of Hydroxyphenyl-Ethylamine Derivatives of Some Digitalisglycosides and Their Aglycones [Zur Radiojodmarkierung von Tyraminderivativen Einiger Digitalisglykoside und Deren Aglyka]", Journal of Labelled Compounds and Radiopharmaceuticals, XP055221078, 15: 197-214, Jan. 1978. Compounds 19, 20, 25, 26, Preparation.

Serrano-Wu et al. "Sordarin Oxazepine Derivatives as Potent Antifungal Agents", Bioorganic and Medicinal Chemistry Letters, 12: 2757-2760, 2002.

Specht et al. "Two Different Na,K-ATPases in the Optic Nerve: Cells of Origin and Axonal Transport", Proc. Natl. Acad. Sci. USA, 81: 1234-1238, Feb. 1984.

Strugatsky et al. "Expression of Na+,K+-ATPase in Pichia Pastoris. Analysis of Wild Type and D369N Mutant Proteins by Fe2+-Catalyzed Oxidative Cleavage", The Journal of Biological Chemistry, 278(46): 46064-46073, Nov. 14, 2003.

Sweadner "Isozymes of the Na+/K+-ATPase", Biochimica et Biophysica Acta, 988: 185-220, 1989.

Sweadner "Two Molecular Froms of (Na+ + K+)-Stimulated ATPase in Brain. Separation, and Difference in Affinity for Strophanthidin", The Journal of Biological Chemistry, 254(13): 6060-6067, Jul. 10, 1979.

Tian et al. "Signal-Transducing Function of Na+-K+-ATPase is Essential for Ouabain's Effect on [Ca2+]I in Rat Cardiac Myocytes", American Journal of Physiology—Heart and Circulation Physiology, 281: H1899-H1907, 2001.

Xie et al. "Na+/K+-ATPase as A Signal Transducer", European Journal of Biochemistry, 269: 2434-2439, Feb. 2002.

Yeagle et al. "Effects of Cholesterol on (Na+,K+)-ATPase ATP Hydrolyzing Activity in Bovine Kidney", Biochemistry, 27: 6449-6452, 1988.

Office Action dated Jun. 21, 2018 From the Israel Patent Office Re. Application No. 244359 and Its Translation Into English. (6 Pages).

\* cited by examiner

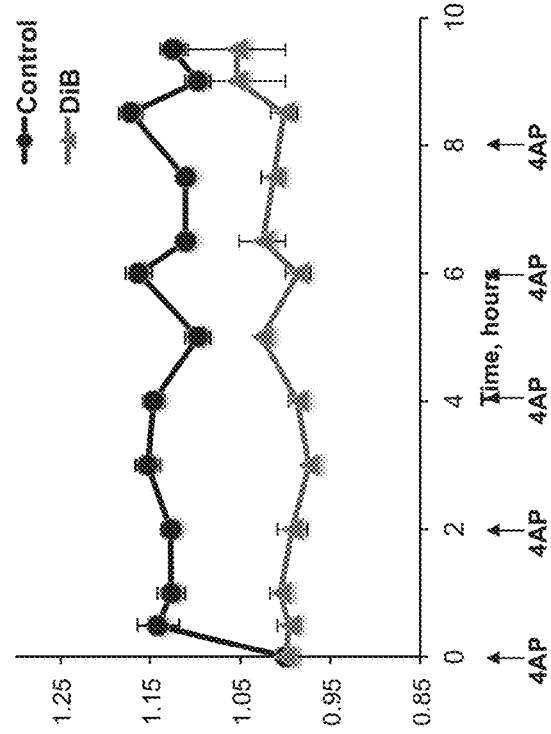
FIG. 1A
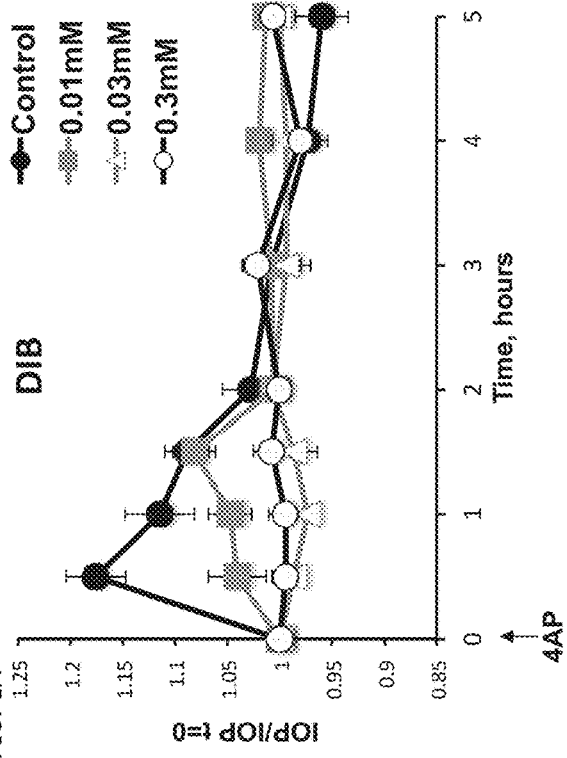
FIG. 1C
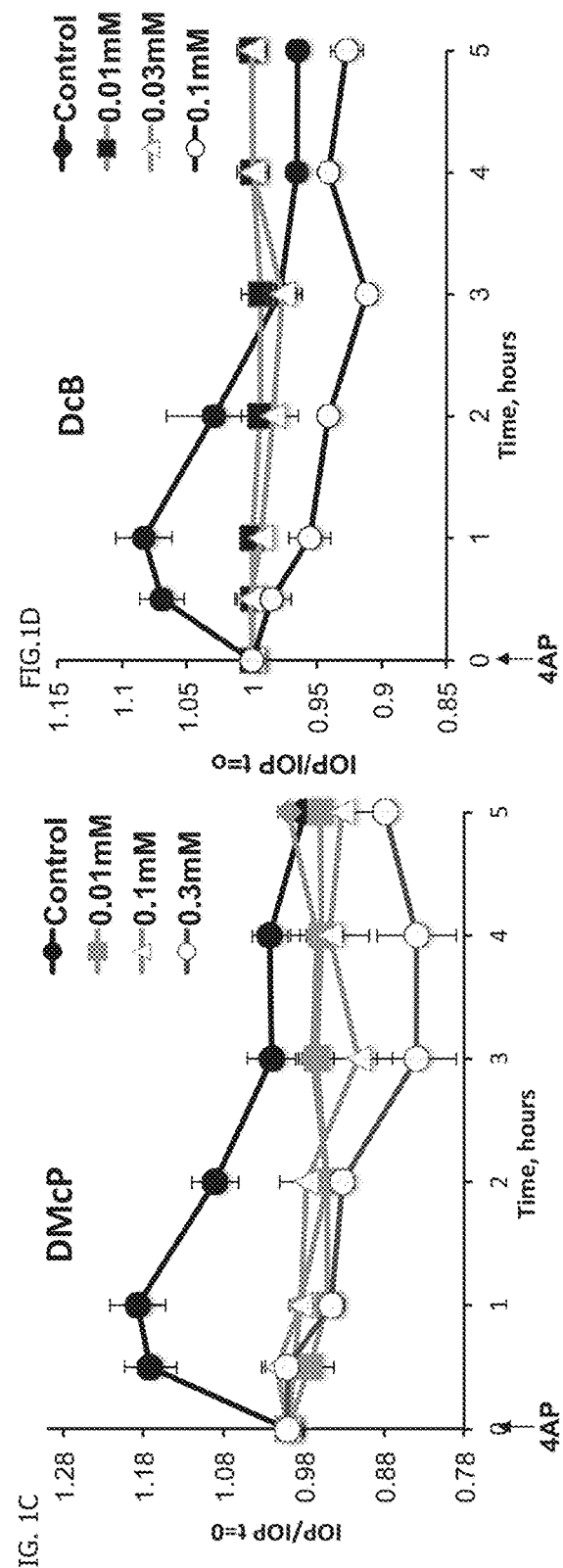
FIG. 1B
FIG. 1D

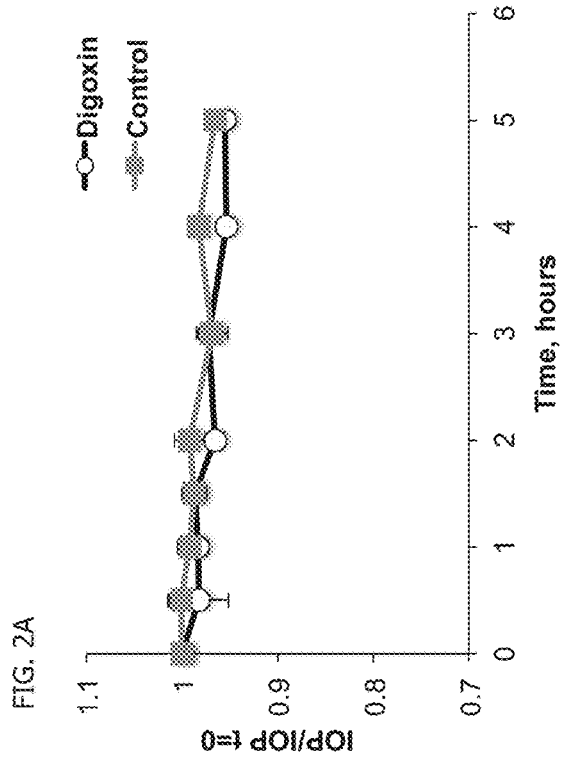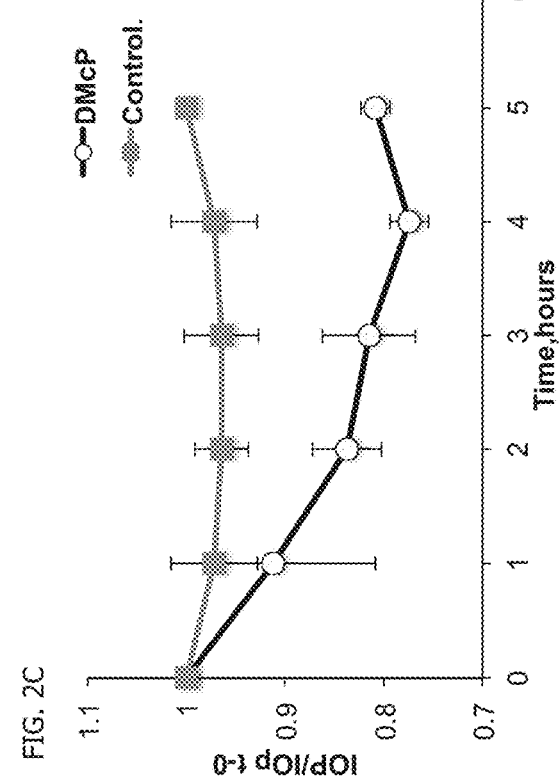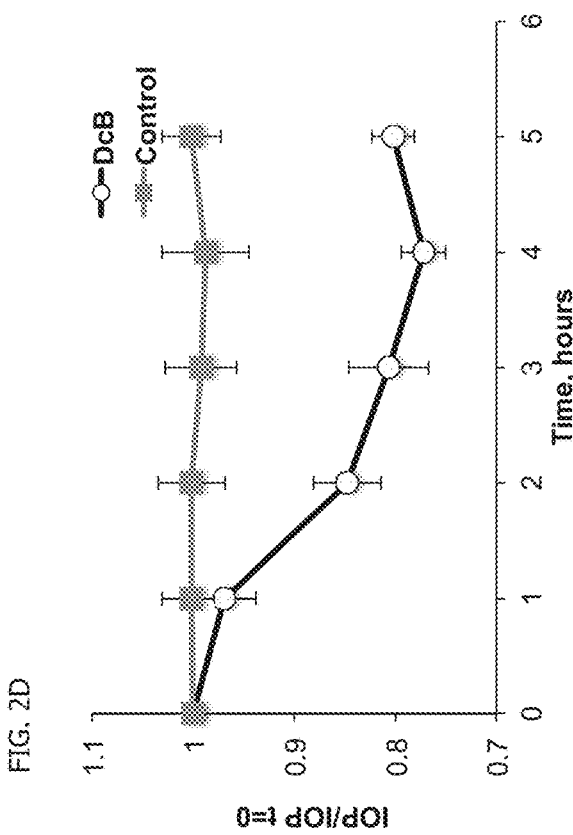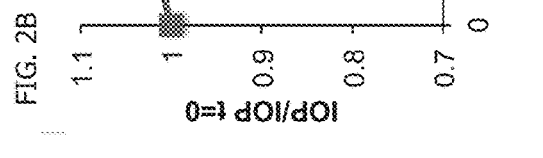

SEQUENCE LISTING

```
<160> NUMBER OF SEQ ID NOS: 19

<210> SEQ ID NO 1
<211> LENGTH: 1023
<212> TYPE: PRT
<213> ORGANISM: homo sapiens

<400> SEQUENCE: 1

Met Gly Lys Gly Val Gly Arg Asp Lys Tyr Glu Pro Ala Ala Val Ser
1               5                   10                  15

Glu Gln Gly Asp Lys Lys Gly Lys Lys Gly Lys Lys Asp Arg Asp Met
                20                  25                  30

Asp Glu Leu Lys Lys Glu Val Ser Met Asp His Lys Leu Ser Leu
            35                  40                  45

Asp Glu Leu His Arg Lys Tyr Gly Thr Asp Leu Ser Arg Gly Leu Thr
        50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Ser Ile Gln Ala Ala Thr Glu Glu Glu Pro Gln Asn Asp
        115                 120                 125

Asn Leu Tyr Leu Gly Val Val Leu Ser Ala Val Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175
```

```
Lys Met Ser Ile Asn Ala Glu Glu Val Val Gly Asp Leu Val Glu
            180                 185                 190

Val Lys Gly Gly Asp Arg Ile Pro Ala Asp Leu Arg Ile Ile Ser Ala
            195                 200                 205

Asn Gly Cys Lys Val Asp Asn Ser Ser Leu Thr Gly Glu Ser Glu Pro
            210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Gln Thr Pro Ile Ala Ala Glu Ile
            275                 280                 285

Glu His Phe Ile His Ile Ile Thr Gly Val Ala Val Phe Leu Gly Val
            290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
            355                 360                 365

Ser Thr Ser Thr Ile Cys Ser Asp Lys Thr Gly Thr Leu Thr Gln Asn
            370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
            435                 440                 445

Gly Asp Ala Ser Glu Ser Ala Leu Leu Lys Cys Ile Glu Leu Cys Cys
450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
            500                 505                 510

Arg Ile Leu Asp Arg Cys Ser Ser Ile Leu Leu His Gly Lys Glu Gln
            515                 520                 525

Pro Leu Asp Glu Glu Leu Lys Asp Ala Phe Gln Asn Ala Tyr Leu Glu
            530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
            580                 585                 590
```

-continued

```
Asp Pro Pro Arg Ala Ala Val Pro Asp Ala Val Gly Lys Cys Arg Ser
        595                 600                 605

Ala Gly Ile Lys Val Ile Met Val Thr Gly Asp His Pro Ile Thr Ala
610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
        675                 680                 685

Val Phe Ala Arg Thr Ser Pro Gln Gln Lys Leu Ile Ile Val Glu Gly
690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975

Ala Leu Arg Met Tyr Pro Leu Lys Pro Thr Trp Trp Phe Cys Ala Phe
            980                 985                 990

Pro Tyr Ser Leu Leu Ile Phe Val Tyr Asp Glu Val Arg Lys Leu Ile
        995                 1000                1005

Ile Arg Arg Arg Pro Gly Gly Trp Val Glu Lys Glu Thr Tyr Tyr
```

1010            1015            1020

<210> SEQ ID NO 2
<211> LENGTH: 1020
<212> TYPE: PRT
<213> ORGANISM: homo sapiens

<400> SEQUENCE: 2

Met Gly Arg Gly Ala Gly Arg Glu Tyr Ser Pro Ala Ala Thr Thr Ala
1               5                   10                  15

Glu Asn Gly Gly Gly Lys Lys Lys Gln Lys Glu Lys Glu Leu Asp Glu
            20                  25                  30

Leu Lys Lys Glu Val Ala Met Asp Asp His Lys Leu Ser Leu Asp Glu
        35                  40                  45

Leu Gly Arg Lys Tyr Gln Val Asp Leu Ser Lys Gly Leu Thr Asn Gln
    50                  55                  60

Arg Ala Gln Asp Val Leu Ala Arg Asp Gly Pro Asn Ala Leu Thr Pro
65                  70                  75                  80

Pro Pro Thr Thr Pro Glu Trp Val Lys Phe Cys Arg Gln Leu Phe Gly
                85                  90                  95

Gly Phe Ser Ile Leu Leu Trp Ile Gly Ala Ile Leu Cys Phe Leu Ala
            100                 105                 110

Tyr Gly Ile Gln Ala Ala Met Glu Asp Glu Pro Ser Asn Asp Asn Leu
        115                 120                 125

Tyr Leu Gly Val Val Leu Ala Ala Val Val Ile Val Thr Gly Cys Phe
    130                 135                 140

Ser Tyr Tyr Gln Glu Ala Lys Ser Ser Lys Ile Met Asp Ser Phe Lys
145                 150                 155                 160

Asn Met Val Pro Gln Gln Ala Leu Val Ile Arg Glu Gly Glu Lys Met
                165                 170                 175

Gln Ile Asn Ala Glu Glu Val Val Val Gly Asp Leu Val Glu Val Lys
            180                 185                 190

Gly Gly Asp Arg Val Pro Ala Asp Leu Arg Ile Ile Ser Ser His Gly
        195                 200                 205

Cys Lys Val Asp Asn Ser Ser Leu Thr Gly Glu Ser Glu Pro Gln Thr
    210                 215                 220

Arg Ser Pro Glu Phe Thr His Glu Asn Pro Leu Glu Thr Arg Asn Ile
225                 230                 235                 240

Cys Phe Phe Ser Thr Asn Cys Val Glu Gly Thr Ala Arg Gly Ile Val
                245                 250                 255

Ile Ala Thr Gly Asp Arg Thr Val Met Gly Arg Ile Ala Thr Leu Ala
            260                 265                 270

Ser Gly Leu Glu Val Gly Arg Thr Pro Ile Ala Met Glu Ile Glu His
        275                 280                 285

Phe Ile Gln Leu Ile Thr Gly Val Ala Val Phe Leu Gly Val Ser Phe
    290                 295                 300

Phe Val Leu Ser Leu Ile Leu Gly Tyr Ser Trp Leu Glu Ala Val Ile
305                 310                 315                 320

Phe Leu Ile Gly Ile Ile Val Ala Asn Val Pro Glu Gly Leu Leu Ala
                325                 330                 335

Thr Val Thr Val Cys Leu Thr Leu Thr Ala Lys Arg Met Ala Arg Lys
            340                 345                 350

Asn Cys Leu Val Lys Asn Leu Glu Ala Val Glu Thr Leu Gly Ser Thr
        355                 360                 365

-continued

```
Ser Thr Ile Cys Ser Asp Lys Thr Gly Thr Leu Thr Gln Asn Arg Met
    370                 375                 380

Thr Val Ala His Met Trp Phe Asp Asn Gln Ile His Glu Ala Asp Thr
385                 390                 395                 400

Thr Glu Asp Gln Ser Gly Ala Thr Phe Asp Lys Arg Ser Pro Thr Trp
                405                 410                 415

Thr Ala Leu Ser Arg Ile Ala Gly Leu Cys Asn Arg Ala Val Phe Lys
                420                 425                 430

Ala Gly Gln Glu Asn Ile Ser Val Ser Lys Arg Asp Thr Ala Gly Asp
                435                 440                 445

Ala Ser Glu Ser Ala Leu Leu Lys Cys Ile Glu Leu Ser Cys Gly Ser
450                 455                 460

Val Arg Lys Met Arg Asp Arg Asn Pro Lys Val Ala Glu Ile Pro Phe
465                 470                 475                 480

Asn Ser Thr Asn Lys Tyr Gln Leu Ser Ile His Glu Arg Glu Asp Ser
                485                 490                 495

Pro Gln Ser His Val Leu Val Met Lys Gly Ala Pro Glu Arg Ile Leu
                500                 505                 510

Asp Arg Cys Ser Thr Ile Leu Val Gln Gly Lys Glu Ile Pro Leu Asp
                515                 520                 525

Lys Glu Met Gln Asp Ala Phe Gln Asn Ala Tyr Met Glu Leu Gly Gly
530                 535                 540

Leu Gly Glu Arg Val Leu Gly Phe Cys Gln Leu Asn Leu Pro Ser Gly
545                 550                 555                 560

Lys Phe Pro Arg Gly Phe Lys Phe Asp Thr Asp Glu Leu Asn Phe Pro
                565                 570                 575

Thr Glu Lys Leu Cys Phe Val Gly Leu Met Ser Met Ile Asp Pro Pro
                580                 585                 590

Arg Ala Ala Val Pro Asp Ala Val Gly Lys Cys Arg Ser Ala Gly Ile
                595                 600                 605

Lys Val Ile Met Val Thr Gly Asp His Pro Ile Thr Ala Lys Ala Ile
610                 615                 620

Ala Lys Gly Val Gly Ile Ile Ser Glu Gly Asn Glu Thr Val Glu Asp
625                 630                 635                 640

Ile Ala Ala Arg Leu Asn Ile Pro Met Ser Gln Val Asn Pro Arg Glu
                645                 650                 655

Ala Lys Ala Cys Val Val His Gly Ser Asp Leu Lys Asp Met Thr Ser
                660                 665                 670

Glu Gln Leu Asp Glu Ile Leu Lys Asn His Thr Glu Ile Val Phe Ala
                675                 680                 685

Arg Thr Ser Pro Gln Gln Lys Leu Ile Ile Val Glu Gly Cys Gln Arg
690                 695                 700

Gln Gly Ala Ile Val Ala Val Thr Gly Asp Gly Val Asn Asp Ser Pro
705                 710                 715                 720

Ala Leu Lys Lys Ala Asp Ile Gly Ile Ala Met Gly Ile Ser Gly Ser
                725                 730                 735

Asp Val Ser Lys Gln Ala Ala Asp Met Ile Leu Leu Asp Asp Asn Phe
                740                 745                 750

Ala Ser Ile Val Thr Gly Val Glu Glu Gly Arg Leu Ile Phe Asp Asn
                755                 760                 765

Leu Lys Lys Ser Ile Ala Tyr Thr Leu Thr Ser Asn Ile Pro Glu Ile
770                 775                 780

Thr Pro Phe Leu Leu Phe Ile Ile Ala Asn Ile Pro Leu Pro Leu Gly
```

```
                785                 790                 795                 800
        Thr Val Thr Ile Leu Cys Ile Asp Leu Gly Thr Asp Met Val Pro Ala
                        805                 810                 815

Ile Ser Leu Ala Tyr Glu Ala Ala Glu Ser Asp Ile Met Lys Arg Gln
                        820                 825                 830

Pro Arg Asn Ser Gln Thr Asp Lys Leu Val Asn Glu Arg Leu Ile Ser
                        835                 840                 845

Met Ala Tyr Gly Gln Ile Gly Met Ile Gln Ala Leu Gly Gly Phe Phe
                850                 855                 860

Thr Tyr Phe Val Ile Leu Ala Glu Asn Gly Phe Leu Pro Ser Arg Leu
        865                 870                 875                 880

Leu Gly Ile Arg Leu Asp Trp Asp Asp Arg Thr Met Asn Asp Leu Glu
                        885                 890                 895

Asp Ser Tyr Gly Gln Glu Trp Thr Tyr Glu Gln Arg Lys Val Val Glu
                        900                 905                 910

Phe Thr Cys His Thr Ala Phe Phe Ala Ser Ile Val Val Gln Trp
                        915                 920                 925

Ala Asp Leu Ile Ile Cys Lys Thr Arg Arg Asn Ser Val Phe Gln Gln
                930                 935                 940

Gly Met Lys Asn Lys Ile Leu Ile Phe Gly Leu Leu Glu Glu Thr Ala
        945                 950                 955                 960

Leu Ala Ala Phe Leu Ser Tyr Cys Pro Gly Met Gly Val Ala Leu Arg
                        965                 970                 975

Met Tyr Pro Leu Lys Val Thr Trp Trp Phe Cys Ala Phe Pro Tyr Ser
                        980                 985                 990

Leu Leu Ile Phe Ile Tyr Asp Glu  Val Arg Lys Leu Ile  Leu Arg Arg
                        995                 1000                1005

Tyr Pro  Gly Gly Trp Val Glu  Lys Glu Thr Tyr Tyr
                1010                1015                1020

<210> SEQ ID NO 3
<211> LENGTH: 1013
<212> TYPE: PRT
<213> ORGANISM: homo sapiens

<400> SEQUENCE: 3

Met Gly Asp Lys Lys Asp Asp Lys Asp Ser Pro Lys Lys Asn Lys Gly
        1               5                   10                  15

Lys Glu Arg Arg Asp Leu Asp Asp Leu Lys Lys Glu Val Ala Met Thr
                        20                  25                  30

Glu His Lys Met Ser Val Glu Val Cys Arg Lys Tyr Asn Thr Asp
                    35                  40                  45

Cys Val Gln Gly Leu Thr His Ser Lys Ala Gln Glu Ile Leu Ala Arg
                50                  55                  60

Asp Gly Pro Asn Ala Leu Thr Pro Pro Thr Thr Pro Glu Trp Val
        65                  70                  75                  80

Lys Phe Cys Arg Gln Leu Phe Gly Gly Phe Ser Ile Leu Leu Trp Ile
                        85                  90                  95

Gly Ala Ile Leu Cys Phe Leu Ala Tyr Gly Ile Gln Ala Gly Thr Glu
                        100                 105                 110

Asp Asp Pro Ser Gly Asp Asn Leu Tyr Leu Gly Ile Val Leu Ala Ala
                        115                 120                 125

Val Val Ile Ile Thr Gly Cys Phe Ser Tyr Tyr Gln Glu Ala Lys Ser
                130                 135                 140
```

-continued

```
Ser Lys Ile Met Glu Ser Phe Lys Asn Met Val Pro Gln Gln Ala Leu
145                 150                 155                 160

Val Ile Arg Glu Gly Glu Lys Met Gln Val Asn Ala Glu Glu Val Val
            165                 170                 175

Val Gly Asp Leu Val Glu Ile Lys Gly Gly Asp Arg Val Pro Ala Asp
            180                 185                 190

Leu Arg Ile Ile Ser Ala His Gly Cys Lys Val Asp Asn Ser Ser Leu
        195                 200                 205

Thr Gly Glu Ser Glu Pro Gln Thr Arg Ser Pro Asp Cys Thr His Asp
210                 215                 220

Asn Pro Leu Glu Thr Arg Asn Ile Thr Phe Phe Ser Thr Asn Cys Val
225                 230                 235                 240

Glu Gly Thr Ala Arg Gly Val Val Ala Thr Gly Asp Arg Thr Val
                245                 250                 255

Met Gly Arg Ile Ala Thr Leu Ala Ser Gly Leu Glu Val Gly Lys Thr
                260                 265                 270

Pro Ile Ala Ile Glu Ile Glu His Phe Ile Gln Leu Ile Thr Gly Val
            275                 280                 285

Ala Val Phe Leu Gly Val Ser Phe Phe Ile Leu Ser Leu Ile Leu Gly
290                 295                 300

Tyr Thr Trp Leu Glu Ala Val Ile Phe Leu Ile Gly Ile Ile Val Ala
305                 310                 315                 320

Asn Val Pro Glu Gly Leu Leu Ala Thr Val Thr Val Cys Leu Thr Leu
                325                 330                 335

Thr Ala Lys Arg Met Ala Arg Lys Asn Cys Leu Val Lys Asn Leu Glu
                340                 345                 350

Ala Val Glu Thr Leu Gly Ser Thr Ser Thr Ile Cys Ser Asp Lys Thr
            355                 360                 365

Gly Thr Leu Thr Gln Asn Arg Met Thr Val Ala His Met Trp Phe Asp
370                 375                 380

Asn Gln Ile His Glu Ala Asp Thr Thr Glu Asp Gln Ser Gly Thr Ser
385                 390                 395                 400

Phe Asp Lys Ser Ser His Thr Trp Val Ala Leu Ser His Ile Ala Gly
                405                 410                 415

Leu Cys Asn Arg Ala Val Phe Lys Gly Gly Gln Asp Asn Ile Pro Val
                420                 425                 430

Leu Lys Arg Asp Val Ala Gly Asp Ala Ser Glu Ser Ala Leu Leu Lys
            435                 440                 445

Cys Ile Glu Leu Ser Ser Gly Ser Val Lys Leu Met Arg Glu Arg Asn
450                 455                 460

Lys Lys Val Ala Glu Ile Pro Phe Asn Ser Thr Asn Lys Tyr Gln Leu
465                 470                 475                 480

Ser Ile His Glu Thr Glu Asp Pro Asn Asp Asn Arg Tyr Leu Leu Val
                485                 490                 495

Met Lys Gly Ala Pro Glu Arg Ile Leu Asp Arg Cys Ser Thr Ile Leu
                500                 505                 510

Leu Gln Gly Lys Glu Gln Pro Leu Asp Glu Glu Met Lys Glu Ala Phe
            515                 520                 525

Gln Asn Ala Tyr Leu Glu Leu Gly Gly Leu Gly Glu Arg Val Leu Gly
            530                 535                 540

Phe Cys His Tyr Tyr Leu Pro Glu Glu Gln Phe Pro Lys Gly Phe Ala
545                 550                 555                 560

Phe Asp Cys Asp Asp Val Asn Phe Thr Thr Asp Asn Leu Cys Phe Val
```

-continued

```
                565                 570                 575
Gly Leu Met Ser Met Ile Asp Pro Pro Arg Ala Val Pro Asp Ala
                580                 585                 590
Val Gly Lys Cys Arg Ser Ala Gly Ile Lys Val Ile Met Val Thr Gly
                595                 600                 605
Asp His Pro Ile Thr Ala Lys Ala Ile Ala Lys Gly Val Gly Ile Ile
610                 615                 620
Ser Glu Gly Asn Glu Thr Val Glu Asp Ile Ala Arg Leu Asn Ile
625                 630                 635                 640
Pro Val Ser Gln Val Asn Pro Arg Asp Ala Lys Ala Cys Val Ile His
                645                 650                 655
Gly Thr Asp Leu Lys Asp Phe Thr Ser Glu Gln Ile Asp Glu Ile Leu
                660                 665                 670
Gln Asn His Thr Glu Ile Val Phe Ala Arg Thr Ser Pro Gln Gln Lys
                675                 680                 685
Leu Ile Ile Val Glu Gly Cys Gln Arg Gln Gly Ala Ile Val Ala Val
                690                 695                 700
Thr Gly Asp Gly Val Asn Asp Ser Pro Ala Leu Lys Lys Ala Asp Ile
705                 710                 715                 720
Gly Val Ala Met Gly Ile Ala Gly Ser Asp Val Ser Lys Gln Ala Ala
                725                 730                 735
Asp Met Ile Leu Leu Asp Asp Asn Phe Ala Ser Ile Val Thr Gly Val
                740                 745                 750
Glu Glu Gly Arg Leu Ile Phe Asp Asn Leu Lys Lys Ser Ile Ala Tyr
                755                 760                 765
Thr Leu Thr Ser Asn Ile Pro Glu Ile Thr Pro Phe Leu Leu Phe Ile
770                 775                 780
Met Ala Asn Ile Pro Leu Pro Leu Gly Thr Ile Thr Ile Leu Cys Ile
785                 790                 795                 800
Asp Leu Gly Thr Asp Met Val Pro Ala Ile Ser Leu Ala Tyr Glu Ala
                805                 810                 815
Ala Glu Ser Asp Ile Met Lys Arg Gln Pro Arg Asn Pro Arg Thr Asp
                820                 825                 830
Lys Leu Val Asn Glu Arg Leu Ile Ser Met Ala Tyr Gly Gln Ile Gly
                835                 840                 845
Met Ile Gln Ala Leu Gly Gly Phe Phe Ser Tyr Phe Val Ile Leu Ala
                850                 855                 860
Glu Asn Gly Phe Leu Pro Gly Asn Leu Val Gly Ile Arg Leu Asn Trp
865                 870                 875                 880
Asp Asp Arg Thr Val Asn Asp Leu Glu Asp Ser Tyr Gly Gln Gln Trp
                885                 890                 895
Thr Tyr Glu Gln Arg Lys Val Val Glu Phe Thr Cys His Thr Ala Phe
                900                 905                 910
Phe Val Ser Ile Val Val Gln Trp Ala Asp Leu Ile Ile Cys Lys
                915                 920                 925
Thr Arg Arg Asn Ser Val Phe Gln Gln Gly Met Lys Asn Lys Ile Leu
930                 935                 940
Ile Phe Gly Leu Phe Glu Glu Thr Ala Leu Ala Ala Phe Leu Ser Tyr
945                 950                 955                 960
Cys Pro Gly Met Asp Val Ala Leu Arg Met Tyr Pro Leu Lys Pro Ser
                965                 970                 975
Trp Trp Phe Cys Ala Phe Pro Tyr Ser Phe Leu Ile Phe Val Tyr Asp
                980                 985                 990
```

Glu Ile Arg Lys Leu Ile Leu Arg Arg Asn Pro Gly Gly Trp Val Glu
        995                 1000                1005

Lys Glu Thr Tyr Tyr
    1010

<210> SEQ ID NO 4
<211> LENGTH: 1029
<212> TYPE: PRT
<213> ORGANISM: homo sapiens

<400> SEQUENCE: 4

Met Gly Leu Trp Gly Lys Lys Gly Thr Val Ala Pro His Asp Gln Ser
1               5                   10                  15

Pro Arg Arg Pro Lys Lys Gly Leu Ile Lys Lys Met Val Lys
            20                  25                  30

Arg Glu Lys Gln Lys Arg Asn Met Glu Glu Leu Lys Lys Glu Val Val
            35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80

Thr Arg Gly Gly Pro Asn Thr Val Thr Pro Pro Thr Thr Pro Glu
                85                  90                  95

Trp Val Lys Phe Cys Lys Gln Leu Phe Gly Gly Phe Ser Leu Leu Leu
            100                 105                 110

Trp Thr Gly Ala Ile Leu Cys Phe Val Ala Tyr Ser Ile Gln Ile Tyr
            115                 120                 125

Phe Asn Glu Glu Pro Thr Lys Asp Asn Leu Tyr Leu Ser Ile Val Leu
    130                 135                 140

Ser Val Val Val Ile Val Thr Gly Cys Phe Ser Tyr Tyr Gln Glu Ala
145                 150                 155                 160

Lys Ser Ser Lys Ile Met Glu Ser Phe Lys Asn Met Val Pro Gln Gln
                165                 170                 175

Ala Leu Val Ile Arg Gly Gly Glu Lys Met Gln Ile Asn Val Gln Glu
            180                 185                 190

Val Val Leu Gly Asp Leu Val Glu Ile Lys Gly Gly Asp Arg Val Pro
            195                 200                 205

Ala Asp Leu Arg Leu Ile Ser Ala Gln Gly Cys Lys Val Asp Asn Ser
    210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
                245                 250                 255

Cys Val Glu Gly Thr Ala Arg Gly Ile Val Ile Ala Thr Gly Asp Ser
            260                 265                 270

Thr Val Met Gly Arg Ile Ala Ser Leu Thr Ser Gly Leu Ala Val Gly
            275                 280                 285

Gln Thr Pro Ile Ala Ala Glu Ile Glu His Phe Ile His Leu Ile Thr
    290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
                325                 330                 335

Val Ala Asn Val Pro Glu Gly Leu Leu Ala Thr Val Thr Val Cys Leu

-continued

```
                340                 345                 350
Thr Leu Thr Ala Lys Arg Met Ala Arg Lys Asn Cys Leu Val Lys Asn
            355                 360                 365
Leu Glu Ala Val Glu Thr Leu Gly Ser Thr Ser Thr Ile Cys Ser Asp
370                 375                 380
Lys Thr Gly Thr Leu Thr Gln Asn Arg Met Thr Val Ala His Met Trp
385                 390                 395                 400
Phe Asp Met Thr Val Tyr Glu Ala Asp Thr Thr Glu Glu Gln Thr Gly
                405                 410                 415
Lys Thr Phe Thr Lys Ser Ser Asp Thr Trp Phe Met Leu Ala Arg Ile
            420                 425                 430
Ala Gly Leu Cys Asn Arg Ala Asp Phe Lys Ala Asn Gln Glu Ile Leu
            435                 440                 445
Pro Ile Ala Lys Arg Ala Thr Thr Gly Asp Ala Ser Glu Ser Ala Leu
            450                 455                 460
Leu Lys Phe Ile Glu Gln Ser Tyr Ser Ser Val Ala Glu Met Arg Glu
465                 470                 475                 480
Lys Asn Pro Lys Val Ala Glu Ile Pro Phe Asn Ser Thr Asn Lys Tyr
                485                 490                 495
Gln Met Ser Ile His Leu Arg Glu Asp Ser Ser Gln Thr His Val Leu
            500                 505                 510
Met Met Lys Gly Ala Pro Glu Arg Ile Leu Glu Phe Cys Ser Thr Phe
            515                 520                 525
Leu Leu Asn Gly Gln Glu Tyr Ser Met Asn Asp Glu Met Lys Glu Ala
            530                 535                 540
Phe Gln Asn Ala Tyr Leu Glu Leu Gly Gly Leu Gly Glu Arg Val Leu
545                 550                 555                 560
Gly Phe Cys Phe Leu Asn Leu Pro Ser Ser Phe Ser Lys Gly Phe Pro
                565                 570                 575
Phe Asn Thr Asp Glu Ile Asn Phe Pro Met Asp Asn Leu Cys Phe Val
                580                 585                 590
Gly Leu Ile Ser Met Ile Asp Pro Pro Arg Ala Ala Val Pro Asp Ala
            595                 600                 605
Val Ser Lys Cys Arg Ser Ala Gly Ile Lys Val Ile Met Val Thr Gly
            610                 615                 620
Asp His Pro Ile Thr Ala Lys Ala Ile Ala Lys Gly Val Gly Ile Ile
625                 630                 635                 640
Ser Glu Gly Thr Glu Thr Ala Glu Glu Val Ala Ala Arg Leu Lys Ile
                645                 650                 655
Pro Ile Ser Lys Val Asp Ala Ser Ala Ala Lys Ala Ile Val Val His
            660                 665                 670
Gly Ala Glu Leu Lys Asp Ile Gln Ser Lys Gln Leu Asp Gln Ile Leu
            675                 680                 685
Gln Asn His Pro Glu Ile Val Phe Ala Arg Thr Ser Pro Gln Gln Lys
            690                 695                 700
Leu Ile Ile Val Glu Gly Cys Gln Arg Leu Gly Ala Val Val Ala Val
705                 710                 715                 720
Thr Gly Asp Gly Val Asn Asp Ser Pro Ala Leu Lys Lys Ala Asp Ile
                725                 730                 735
Gly Ile Ala Met Gly Ile Ser Gly Ser Asp Val Ser Lys Gln Ala Ala
            740                 745                 750
Asp Met Ile Leu Leu Asp Asp Asn Phe Ala Ser Ile Val Thr Gly Val
            755                 760                 765
```

Glu Gly Arg Leu Ile Phe Asp Asn Leu Lys Lys Ser Ile Met Tyr
    770             775                 780

Thr Leu Thr Ser Asn Ile Pro Glu Ile Thr Pro Phe Leu Met Phe Ile
785             790                 795                 800

Ile Leu Gly Ile Pro Leu Pro Leu Gly Thr Ile Thr Ile Leu Cys Ile
                805                 810                 815

Asp Leu Gly Thr Asp Met Val Pro Ala Ile Ser Leu Ala Tyr Glu Ser
                820                 825                 830

Ala Glu Ser Asp Ile Met Lys Arg Leu Pro Arg Asn Pro Lys Thr Asp
                835                 840                 845

Asn Leu Val Asn His Arg Leu Ile Gly Met Ala Tyr Gly Gln Ile Gly
    850                 855                 860

Met Ile Gln Ala Leu Ala Gly Phe Phe Thr Tyr Phe Val Ile Leu Ala
865             870                 875                 880

Glu Asn Gly Phe Arg Pro Val Asp Leu Leu Gly Ile Arg Leu His Trp
                885                 890                 895

Glu Asp Lys Tyr Leu Asn Asp Leu Glu Asp Ser Tyr Gly Gln Gln Trp
                900                 905                 910

Thr Tyr Glu Gln Arg Lys Val Val Glu Phe Thr Cys Gln Thr Ala Phe
                915                 920                 925

Phe Val Thr Ile Val Val Gln Trp Ala Asp Leu Ile Ile Ser Lys
    930                 935                 940

Thr Arg Arg Asn Ser Leu Phe Gln Gln Gly Met Arg Asn Lys Val Leu
945             950                 955                 960

Ile Phe Gly Ile Leu Glu Glu Thr Leu Leu Ala Ala Phe Leu Ser Tyr
                965                 970                 975

Thr Pro Gly Met Asp Val Ala Leu Arg Met Tyr Pro Leu Lys Ile Thr
                980                 985                 990

Trp Trp Leu Cys Ala Ile Pro Tyr Ser Ile Leu Ile Phe Val Tyr Asp
                995                 1000                1005

Glu Ile Arg Lys Leu Leu Ile Arg Gln His Pro Asp Gly Trp Val
    1010                1015                1020

Glu Arg Glu Thr Tyr Tyr
    1025

<210> SEQ ID NO 5
<211> LENGTH: 303
<212> TYPE: PRT
<213> ORGANISM: homo sapiens

<400> SEQUENCE: 5

Met Ala Arg Gly Lys Ala Lys Glu Glu Gly Ser Trp Lys Lys Phe Ile
1               5                   10                  15

Trp Asn Ser Glu Lys Lys Glu Phe Leu Gly Arg Thr Gly Gly Ser Trp
                20                  25                  30

Phe Lys Ile Leu Leu Phe Tyr Val Ile Phe Tyr Gly Cys Leu Ala Gly
            35                  40                  45

Ile Phe Ile Gly Thr Ile Gln Val Met Leu Leu Thr Ile Ser Glu Phe
        50                  55                  60

Lys Pro Thr Tyr Gln Asp Arg Val Ala Pro Pro Gly Leu Thr Gln Ile
65              70                  75                  80

Pro Gln Ile Gln Lys Thr Glu Ile Ser Phe Arg Pro Asn Asp Pro Lys
                85                  90                  95

Ser Tyr Glu Ala Tyr Val Leu Asn Ile Val Arg Phe Leu Glu Lys Tyr

```
              100                 105                 110
Lys Asp Ser Ala Gln Arg Asp Asp Met Ile Phe Glu Asp Cys Gly Asp
            115                 120                 125

Val Pro Ser Glu Pro Lys Glu Arg Gly Asp Phe Asn His Glu Arg Gly
    130                 135                 140

Glu Arg Lys Val Cys Arg Phe Lys Leu Glu Trp Leu Gly Asn Cys Ser
145                 150                 155                 160

Gly Leu Asn Asp Glu Thr Tyr Gly Tyr Lys Glu Gly Lys Pro Cys Ile
                165                 170                 175

Ile Ile Lys Leu Asn Arg Val Leu Gly Phe Lys Pro Lys Pro Pro Lys
            180                 185                 190

Asn Glu Ser Leu Glu Thr Tyr Pro Val Met Lys Tyr Asn Pro Asn Val
        195                 200                 205

Leu Pro Val Gln Cys Thr Gly Lys Arg Asp Glu Asp Lys Asp Lys Val
    210                 215                 220

Gly Asn Val Glu Tyr Phe Gly Leu Gly Asn Ser Pro Gly Phe Pro Leu
225                 230                 235                 240

Gln Tyr Tyr Pro Tyr Tyr Gly Lys Leu Leu Gln Pro Lys Tyr Leu Gln
                245                 250                 255

Pro Leu Leu Ala Val Gln Phe Thr Asn Leu Thr Met Asp Thr Glu Ile
            260                 265                 270

Arg Ile Glu Cys Lys Ala Tyr Gly Glu Asn Ile Gly Tyr Ser Glu Lys
        275                 280                 285

Asp Arg Phe Gln Gly Arg Phe Asp Val Lys Ile Glu Val Lys Ser
    290                 295                 300

<210> SEQ ID NO 6
<211> LENGTH: 319
<212> TYPE: PRT
<213> ORGANISM: Artificial sequence
<220> FEATURE:
<223> OTHER INFORMATION: Amino Acid sequence encoding His10-ATP1B1

<400> SEQUENCE: 6

Met Ala Arg Ser His His His His His His His His His Pro Arg
1               5                   10                  15

Arg Ser Arg Gly Lys Ala Lys Glu Glu Gly Ser Trp Lys Lys Phe Ile
            20                  25                  30

Trp Asn Ser Glu Lys Lys Glu Phe Leu Gly Arg Thr Gly Gly Ser Trp
        35                  40                  45

Phe Lys Ile Leu Leu Phe Tyr Val Ile Phe Tyr Gly Cys Leu Ala Gly
    50                  55                  60

Ile Phe Ile Gly Thr Ile Gln Val Met Leu Leu Thr Ile Ser Glu Phe
65                  70                  75                  80

Lys Pro Thr Tyr Gln Asp Arg Val Ala Pro Pro Gly Leu Thr Gln Ile
                85                  90                  95

Pro Gln Ile Gln Lys Thr Glu Ile Ser Phe Arg Pro Asn Asp Pro Lys
            100                 105                 110

Ser Tyr Glu Ala Tyr Val Leu Asn Ile Val Arg Phe Leu Glu Lys Tyr
        115                 120                 125

Lys Asp Ser Ala Gln Arg Asp Asp Met Ile Phe Glu Asp Cys Gly Asp
    130                 135                 140

Val Pro Ser Glu Pro Lys Glu Arg Gly Asp Phe Asn His Glu Arg Gly
145                 150                 155                 160

Glu Arg Lys Val Cys Arg Phe Lys Leu Glu Trp Leu Gly Asn Cys Ser
```

```
            165                 170                 175
Gly Leu Asn Asp Glu Thr Tyr Gly Tyr Lys Glu Gly Lys Pro Cys Ile
            180                 185                 190

Ile Ile Lys Leu Asn Arg Val Leu Gly Phe Lys Pro Lys Pro Pro Lys
            195                 200                 205

Asn Glu Ser Leu Glu Thr Tyr Pro Val Met Lys Tyr Asn Pro Asn Val
            210                 215                 220

Leu Pro Val Gln Cys Thr Gly Lys Arg Asp Glu Asp Lys Asp Lys Val
225                 230                 235                 240

Gly Asn Val Glu Tyr Phe Gly Leu Gly Asn Ser Pro Gly Phe Pro Leu
            245                 250                 255

Gln Tyr Tyr Pro Tyr Tyr Gly Lys Leu Leu Gln Pro Lys Tyr Leu Gln
            260                 265                 270

Pro Leu Leu Ala Val Gln Phe Thr Asn Leu Thr Met Asp Thr Glu Ile
            275                 280                 285

Arg Ile Glu Cys Lys Ala Tyr Gly Glu Asn Ile Gly Tyr Ser Glu Lys
            290                 295                 300

Asp Arg Phe Gln Gly Arg Phe Asp Val Lys Ile Glu Val Lys Ser
305                 310                 315

<210> SEQ ID NO 7
<211> LENGTH: 290
<212> TYPE: PRT
<213> ORGANISM: homo sapiens

<400> SEQUENCE: 7

Met Val Ile Gln Lys Glu Lys Lys Ser Cys Gly Gln Val Val Glu Glu
1               5                   10                  15

Trp Lys Glu Phe Val Trp Asn Pro Arg Thr His Gln Phe Met Gly Arg
            20                  25                  30

Thr Gly Thr Ser Trp Ala Phe Ile Leu Leu Phe Tyr Leu Val Phe Tyr
            35                  40                  45

Gly Phe Leu Thr Ala Met Phe Thr Leu Thr Met Trp Val Met Leu Gln
50                  55                  60

Thr Val Ser Asp His Thr Pro Lys Tyr Gln Asp Arg Leu Ala Thr Pro
65                  70                  75                  80

Gly Leu Met Ile Arg Pro Lys Thr Glu Asn Leu Asp Val Ile Val Asn
            85                  90                  95

Val Ser Asp Thr Glu Ser Trp Asp Gln His Val Gln Lys Leu Asn Lys
            100                 105                 110

Phe Leu Glu Pro Tyr Asn Asp Ser Ile Gln Ala Gln Lys Asn Asp Val
            115                 120                 125

Cys Arg Pro Gly Arg Tyr Tyr Glu Gln Pro Asp Asn Gly Val Leu Asn
130                 135                 140

Tyr Pro Lys Arg Ala Cys Gln Phe Asn Arg Thr Gln Leu Gly Asn Cys
145                 150                 155                 160

Ser Gly Ile Gly Asp Ser Thr His Tyr Gly Tyr Ser Thr Gly Gln Pro
            165                 170                 175

Cys Val Phe Ile Lys Met Asn Arg Val Ile Asn Phe Tyr Ala Gly Ala
            180                 185                 190

Asn Gln Ser Met Asn Val Thr Cys Ala Gly Lys Arg Asp Glu Asp Ala
            195                 200                 205

Glu Asn Leu Gly Asn Phe Val Met Phe Pro Ala Asn Gly Asn Ile Asp
            210                 215                 220
```

Leu Met Tyr Phe Pro Tyr Tyr Gly Lys Lys Phe His Val Asn Tyr Thr
225                 230                 235                 240

Gln Pro Leu Val Ala Val Lys Phe Leu Asn Val Thr Pro Asn Val Glu
                245                 250                 255

Val Asn Val Glu Cys Arg Ile Asn Ala Ala Asn Ile Ala Thr Asp Asp
                260                 265                 270

Glu Arg Asp Lys Phe Ala Gly Arg Val Ala Phe Lys Leu Arg Ile Asn
                275                 280                 285

Lys Thr
    290

<210> SEQ ID NO 8
<211> LENGTH: 306
<212> TYPE: PRT
<213> ORGANISM: Artificial sequence
<220> FEATURE:
<223> OTHER INFORMATION: Amino Acid sequence encoding His10-ATP1B2

<400> SEQUENCE: 8

Met Ala Arg Ser His His His His His His His His Pro Arg
1               5                   10                  15

Arg Ser Arg Gly Lys Glu Lys Ser Cys Gly Gln Val Val Glu Glu
                20                  25                  30

Trp Lys Glu Phe Val Trp Asn Pro Arg Thr His Gln Phe Met Gly Arg
        35                  40                  45

Thr Gly Thr Ser Trp Ala Phe Ile Leu Leu Phe Tyr Leu Val Phe Tyr
    50                  55                  60

Gly Phe Leu Thr Ala Met Phe Thr Leu Thr Met Trp Val Met Leu Gln
65                  70                  75                  80

Thr Val Ser Asp His Thr Pro Lys Tyr Gln Asp Arg Leu Ala Thr Pro
                85                  90                  95

Gly Leu Met Ile Arg Pro Lys Thr Glu Asn Leu Asp Val Ile Val Asn
                100                 105                 110

Val Ser Asp Thr Glu Ser Trp Asp Gln His Val Gln Lys Leu Asn Lys
                115                 120                 125

Phe Leu Glu Pro Tyr Asn Asp Ser Ile Gln Ala Gln Lys Asn Asp Val
    130                 135                 140

Cys Arg Pro Gly Arg Tyr Tyr Glu Gln Pro Asp Asn Gly Val Leu Asn
145                 150                 155                 160

Tyr Pro Lys Arg Ala Cys Gln Phe Asn Arg Thr Gln Leu Gly Asn Cys
                165                 170                 175

Ser Gly Ile Gly Asp Ser Thr His Tyr Gly Tyr Ser Thr Gly Gln Pro
                180                 185                 190

Cys Val Phe Ile Lys Met Asn Arg Val Ile Asn Phe Tyr Ala Gly Ala
                195                 200                 205

Asn Gln Ser Met Asn Val Thr Cys Ala Gly Lys Arg Asp Glu Asp Ala
    210                 215                 220

Glu Asn Leu Gly Asn Phe Val Met Phe Pro Ala Asn Gly Asn Ile Asp
225                 230                 235                 240

Leu Met Tyr Phe Pro Tyr Tyr Gly Lys Lys Phe His Val Asn Tyr Thr
                245                 250                 255

Gln Pro Leu Val Ala Val Lys Phe Leu Asn Val Thr Pro Asn Val Glu
                260                 265                 270

Val Asn Val Glu Cys Arg Ile Asn Ala Ala Asn Ile Ala Thr Asp Asp
                275                 280                 285

Glu Arg Asp Lys Phe Ala Gly Arg Val Ala Phe Lys Leu Arg Ile Asn
290                 295                 300

Lys Thr
305

<210> SEQ ID NO 9
<211> LENGTH: 279
<212> TYPE: PRT
<213> ORGANISM: homo sapiens

<400> SEQUENCE: 9

Met Thr Lys Asn Glu Lys Lys Ser Leu Asn Gln Ser Leu Ala Glu Trp
1               5                   10                  15

Lys Leu Phe Ile Tyr Asn Pro Thr Thr Gly Glu Phe Leu Gly Arg Thr
            20                  25                  30

Ala Lys Ser Trp Gly Leu Ile Leu Leu Phe Tyr Leu Val Phe Tyr Gly
        35                  40                  45

Phe Leu Ala Ala Leu Phe Ser Phe Thr Met Trp Val Met Leu Gln Thr
    50                  55                  60

Leu Asn Asp Glu Val Pro Lys Tyr Arg Asp Gln Ile Pro Ser Pro Gly
65                  70                  75                  80

Leu Met Val Phe Pro Lys Pro Val Thr Ala Leu Glu Tyr Thr Phe Ser
                85                  90                  95

Arg Ser Asp Pro Thr Ser Tyr Ala Gly Tyr Ile Glu Asp Leu Lys Lys
            100                 105                 110

Phe Leu Lys Pro Tyr Thr Leu Glu Glu Gln Lys Asn Leu Thr Val Cys
        115                 120                 125

Pro Asp Gly Ala Leu Phe Glu Gln Lys Gly Pro Val Tyr Val Ala Cys
    130                 135                 140

Gln Phe Pro Ile Ser Leu Leu Gln Ala Cys Ser Gly Met Asn Asp Pro
145                 150                 155                 160

Asp Phe Gly Tyr Ser Gln Gly Asn Pro Cys Ile Leu Val Lys Met Asn
                165                 170                 175

Arg Ile Ile Gly Leu Lys Pro Glu Gly Val Pro Arg Ile Asp Cys Val
            180                 185                 190

Ser Lys Asn Glu Asp Ile Pro Asn Val Ala Val Tyr Pro His Asn Gly
        195                 200                 205

Met Ile Asp Leu Lys Tyr Phe Pro Tyr Tyr Gly Lys Lys Leu His Val
    210                 215                 220

Gly Tyr Leu Gln Pro Leu Val Ala Val Gln Val Ser Phe Ala Pro Asn
225                 230                 235                 240

Asn Thr Gly Lys Glu Val Thr Val Glu Cys Lys Ile Asp Gly Ser Ala
                245                 250                 255

Asn Leu Lys Ser Gln Asp Asp Arg Asp Lys Phe Leu Gly Arg Val Met
            260                 265                 270

Phe Lys Ile Thr Ala Arg Ala
        275

<210> SEQ ID NO 10
<211> LENGTH: 296
<212> TYPE: PRT
<213> ORGANISM: Artificial sequence
<220> FEATURE:
<223> OTHER INFORMATION: Amino Acid sequence encoding His10-ATP1B3

<400> SEQUENCE: 10

Met Ala Arg Ser His His His His His His His His His His Pro Arg

```
                1               5                  10                 15
            Arg Ser Arg Gly Asn Glu Lys Lys Ser Leu Asn Gln Ser Leu Ala Glu
                            20                  25                 30

Trp Lys Leu Phe Ile Tyr Asn Pro Thr Thr Gly Glu Phe Leu Gly Arg
                            35                  40                 45

Thr Ala Lys Ser Trp Gly Leu Ile Leu Leu Phe Tyr Leu Val Phe Tyr
                            50                  55                 60

Gly Phe Leu Ala Ala Leu Phe Ser Phe Thr Met Trp Val Met Leu Gln
             65                  70                  75                 80

Thr Leu Asn Asp Glu Val Pro Lys Tyr Arg Asp Gln Ile Pro Ser Pro
                            85                  90                 95

Gly Leu Met Val Phe Pro Lys Pro Val Thr Ala Leu Glu Tyr Thr Phe
                           100                 105                110

Ser Arg Ser Asp Pro Thr Ser Tyr Ala Gly Tyr Ile Glu Asp Leu Lys
                           115                 120                125

Lys Phe Leu Lys Pro Tyr Thr Leu Glu Glu Gln Lys Asn Leu Thr Val
                           130                 135                140

Cys Pro Asp Gly Ala Leu Phe Glu Gln Lys Gly Pro Val Tyr Val Ala
            145                 150                 155                160

Cys Gln Phe Pro Ile Ser Leu Leu Gln Ala Cys Ser Gly Met Asn Asp
                           165                 170                175

Pro Asp Phe Gly Tyr Ser Gln Gly Asn Pro Cys Ile Leu Val Lys Met
                           180                 185                190

Asn Arg Ile Ile Gly Leu Lys Pro Glu Gly Val Pro Arg Ile Asp Cys
                           195                 200                205

Val Ser Lys Asn Glu Asp Ile Pro Asn Val Ala Val Tyr Pro His Asn
                           210                 215                220

Gly Met Ile Asp Leu Lys Tyr Phe Pro Tyr Tyr Gly Lys Lys Leu His
            225                 230                 235                240

Val Gly Tyr Leu Gln Pro Leu Val Ala Val Gln Val Ser Phe Ala Pro
                           245                 250                255

Asn Asn Thr Gly Lys Glu Val Thr Val Glu Cys Lys Ile Asp Gly Ser
                           260                 265                270

Ala Asn Leu Lys Ser Gln Asp Asp Arg Asp Lys Phe Leu Gly Arg Val
                           275                 280                285

Met Phe Lys Ile Thr Ala Arg Ala
                           290                 295

<210> SEQ ID NO 11
<211> LENGTH: 3072
<212> TYPE: DNA
<213> ORGANISM: homo sapiens

<400> SEQUENCE: 11
atggggaagg gggttggacg tgataagtat gagcctgcag ctgtttcaga acaaggtgat      60
aaaaagggca aaaagggcaa aaaagacagg gacatggatg aactgaagaa agaagtttct     120
atggatgatc ataaacttag ccttgatgaa cttcatcgta aatatggaac agacttgagc     180
cggggattaa catctgctcg tgcagctgag atcctggcgc gagatggtcc caacgccctc     240
actccccctc ccactactcc tgaatggatc aagttttgtc ggcagctctt tgggggttc      300 tcaatgttac tgtggattgg agcgattctt tgtttcttgg cttatagcat ccaagctgct     360
acagaagagg aacctcaaaa cgataatctg tacctgggtg tggtgctatc agccgttgta     420
atcataactg gttgcttctc ctactatcaa gaagctaaaa gttcaaagat catggaatcc     480
```

```
ttcaaaaaca tggtccctca gcaagcccct tgtgattcgaa atggtgagaa aatgagcata    540
aatgcggagg aagttgtggt tggggatctg gtggaagtaa aaggaggaga ccgaattcct    600
gctgacctca gaatcatatc tgcaaatggc tgcaaggtgg ataactcctc gctcactggt    660
gaatcagaac cccagactag gtctccagat ttcacaaatg aaaacccct ggagacgagg    720 aacattgcct tcttttcaac aaattgtgtt gaaggcaccg cacgtggtat tgttgtctac    780 actgggatc gcactgtgat gggaagaatt gccacacttg cttctgggct ggaaggaggc    840
cagaccccca ttgctgcaga aattgaacat tttatccaca tcatcacggg tgtggctgtg    900
ttcctgggtg tgtcttttctt catcctttct ctcatccttg agtacacctg gcttgaggct    960
gtcatcttcc tcatcggtat catcgtagcc aatgtgccgg aaggtttgct ggccactgtc   1020
acggtctgtc tgacacttac tgccaaacgc atggcaagga aaaactgctt agtgaagaac   1080
ttagaagctg tggagacctt ggggtccacg tccaccatct gctctgataa aactggaact   1140
ctgactcaga accggatgac agtggcccac atgtggttg acaatcaaat ccatgaagct   1200
gatacgacag agaatcagag tggtgtctct tttgacaaga cttcagctac ctggcttgct   1260
ctgtccagaa ttgcaggtct ttgtaacagg gcagtgttc aggctaacca ggaaaaccta   1320
cctattctta agcgggcagt tgcaggagat gcctctgagt cagcactctt aaagtgcata   1380
gagctgtgct gtggttccgt gaaggagatg agagaaagat acgccaaaat cgtcagagata   1440 cccttcaact ccaccaacaa gtaccagttg tctattcata agaaccccaa cacatcggag   1500
ccccaacacc tgttggtgat gaaggggccc ccagaaagga tcctagaccg ttgcagctct   1560
atcctcctcc acggcaagga gcagcccctg gatgaggagc tgaaagacgc ctttcagaac   1620
gcctatttgg agctggggggg cctcggagaa cgagtcctag gtttctgcca cctctttctg   1680
ccagatgaac agtttcctga agggttccag tttgacactg acgatgtgaa tttccctatc   1740
gataatctgt gctttgttgg gctcatctcc atgattgacc ctccacgggc ggccgttcct   1800
gatgccgtgg gcaaatgtcg aagtgctgga attaaggtca tcatggtcac aggagaccat   1860
ccaatcacag ctaaagctat tgccaaaggt gtgggcatca tctcagaagg caatgagacc   1920
gtggaagaca ttgctgcccg cctcaacatc ccagtcagcc aggtgaaccc cagggatgcc   1980
aaggcctgcg tagtacacgg cagtgatcta aaggacatga cctccgagca gctggatgac   2040
attttgaagt accacactga gatagtgttt gccaggacct cccctcagca gaagctcatc   2100
attgtggaag gctgccaaag acagggtgct atcgtggctg tgactggtga cggtgtgaat   2160
gactctccag ctttgaagaa agcagacatt ggggttgcta tggggattgc tggctcagat   2220
gtgtccaagc aagctgctga catgattctt ctggatgaca actttgcctc aattgtgact   2280
ggagtagagg aaggtcgtct gatctttgat aacttgaaga aatccattgc ttataccttta   2340 accagtaaca ttcccgagat cacccccgttc ctgatattta ttattgcaaa cattccacta   2400
ccactgggga ctgtcaccat cctctgcatt gacttgggca ctgacatggt tcctgccatc   2460
tccctggctt atgagcaggc tgagagtgac atcatgaaga gacagcccag aaatcccaaa   2520
acagacaaac ttgtgaatga gcggctgatc agcatggcct atgggcagat tggaatgatc   2580
caggccctgg gaggcttctt tacttacttt gtgattctgg ctgagaacgg cttcctccca   2640
attcacctgt gggcctccg agtggactgg gatgaccgct ggatcaacga tgtggaagac   2700
agctacgggc agcagtggac ctatgagcag aggaaaatcg tggagttcac ctgccacaca   2760
gccttcttcg tcagtatcgt ggtggtgcag tgggccgact tggtcatctg taagaccagg   2820
```

```
aggaattcgg tcttccagca ggggatgaag aacaagatct tgatatttgg cctctttgaa      2880
gagacagccc tggctgcttt cctttcctac tgccctggaa tgggtgttgc tcttaggatg      2940
tatcccctca aacctacctg gtggttctgt gccttcccct actctcttct catcttcgta      3000
tatgacgaag tcagaaaact catcatcagg cgacgccctg cggctgggt ggagaaggaa       3060 acctactatt ag                                                          3072
```

<210> SEQ ID NO 12
<211> LENGTH: 3063
<212> TYPE: DNA
<213> ORGANISM: homo sapiens

<400> SEQUENCE: 12

```
atgggccgtg gggctggccg tgagtactca cctgccgcca ccacggcaga gaatggggc        60 ggcaagaaga acagaagga gaaggaactg gatgagctga agaaggaggt ggcaatggat       120
gaccacaagc tgtccttgga tgagctgggc cgcaaatacc aagtggacct gtccaagggc      180
ctcaccaacc agcgggctca ggacgttctg gctcgagatg gcccaacgc ctcacacca       240 cctcccacaa cccctgagtg ggtcaagttc tgccgtcagc ttttcggggg gttctccatc      300
ctgctgtgga ttggggctat cctctgcttc ctggcctacg catccaggc tgccatggag       360 gatgaaccat ccaacgacaa tctatatctg ggtgtggtgc tggcagctgt ggtcattgtc      420
actggctgct ctcctactac caggaggcc aagagctcca agatcatgga ttccttcaag       480
aacatggtac tcagcaagc ccttgtgatc cgggagggag agaagatgca gatcaacgca       540
gaggaagtgg tggtgggaga cctggtggag gtgaagggtg agaccgcgt ccctgctgac       600 ctccggatca tctcttctca tggctgtaag gtggataact catccttaac aggagagtcg      660
gagccccaga cccgctcccc cgagttcacc atgagaaacc cctggagac cgcaatatc       720 tgtttcttct ccaccaactg tgttgaaggc actgccaggg gcattgtgat tgccacagga      780
gaccggacgg tgatgggccg catagctact ctcgcctcag gctgaggt tgggcggaca       840 cccatagcaa tggagattga acacttcatc agctgatca caggggtcgc tgtattcctg      900
ggggtctcct tcttcgtgct ctccctcatc tgggctaca gctggctgga gcagtcatc       960 ttcctcatcg gcatcatagt ggccaacgtg cctgagggc ttctggccac tgtcactgtg     1020
tgcctgaccc tgcagccaa cgcatggca cggaagaact gcctggtgaa gaacctggag       1080
gcggtggaga cgctgggctc cacgtccacc atctgctcgg acaagacggg caccctcacc      1140
cagaaccgca tgaccgtcgc ccacatgtgg ttcgacaacc aaatccatga ggctgacacc      1200
accgaagatc agtctggggc cacttttgac aaacgatccc ctacgtggac ggccctgtct      1260
cgaattgctg gtctctgcaa ccgcgccgtc ttcaaggcag acaggagaa catctccgtg      1320 tctaagcggg acacagctgg tgatgcctct gagtcagctc tgctcaagtg cattgagctc      1380
tcctgtggct cagtgaggaa aatgagagac agaaacccca aggtggcaga gattcctttc      1440
aactctacca caagtacca gctgtctatc cacgagcgag aagacagccc ccagagccac      1500
gtgctggtga tgaaggggc cccagagcgc attctggacc ggtgctccac catcctggtg      1560
cagggcaagg agatcccgct cgacaaggag atgcaagatg cctttcaaaa tgcctacatg      1620
gagctggggg gacttgggga gcgtgtgctg ggattctgtc aactgaatct gccatctgga      1680
aagtttcctc ggggcttcaa attcgacacg gatgagctga ctttcccac ggagaagctt      1740 tgctttgtgg ggctcatgtc tatgattgac cctccccggg ctgctgtgcc agatgctgtg      1800
ggcaagtgcc gaagcgcagg catcaaggtg atcatggtaa ccgggatcga ccctatcaca      1860
```

```
gccaaggcca ttgccaaagg cgtgggcatc atatcagagg gtaacgagac tgtggaggac    1920
attgcagccc ggctcaacat tcccatgagt caagtcaacc ccagagaagc caaggcatgc    1980
gtggtgcacg gctctgacct gaaggacatg acatcggagc agctcgatga gatcctcaag    2040
aaccacacag agatcgtctt tgctcgaacg tctcccagc agaagctcat cattgtggag     2100
ggatgtcaga ggcagggagc cattgtggcc gtgacgggtg acggggtgaa cgactcccct    2160
gcattgaaga aggctgacat tggcattgcc atgggcatct ctggctctga cgtctctaag    2220
caggcagccg acatgatcct gctggatgac aactttgcct ccatcgtcac gggggtggag    2280
gagggccgcc tgatctttga caacttgaag aaatccatcg cctacaccct gaccagcaac    2340
atccccgaga tcacccccct cctgctgttc atcattgcca acatccccct acctctgggc    2400
actgtgacca tcctttgcat tgacctgggc acagatatgg tccctgccat ctccttggcc    2460
tatgaggcag ctgagagtga tatcatgaag cggcagccac gaaactccca gacggacaag    2520
ctggtgaatg agaggctcat cagcatggcc tacggacaga tcgggatgat ccaggcactg    2580
ggtggcttct tcacctactt tgtgatcctg gcagagaacg gtttcctgcc atcacggcta    2640
ctgggaatcc gcctcgactg ggatgaccgg accatgaatg atctggagga cagctatgga    2700
caggagtgga cctatgagca gcggaaggtg gtggagttca cgtgccacac ggcattcttt    2760
gccagcatcg tggtggtgca gtgggctgac ctcatcatct gcaagacccg ccgcaactca    2820
gtcttccagc agggcatgaa gaacaagatc ctgattttg ggctcctgga ggagacggcg    2880
ttggctgcct ttctctctta ctgcccaggc atgggtgtag ccctccgcat gtacccgctc    2940
aaagtcacct ggtggttctg cgccttcccc tacagcctcc tcatcttcat ctatgatgag    3000
gtccgaaagc tcatcctgcg gcggtatcct ggtggctggg tggagaagga gacatactac    3060
tga                                                                 3063
```

<210> SEQ ID NO 13
<211> LENGTH: 3042
<212> TYPE: DNA
<213> ORGANISM: homo sapiens

<400> SEQUENCE: 13

```
atgggggaca agaaagatga caaggactca cccaagaaga acaagggcaa ggagcgccgg    60
gacctggatg acctcaagaa ggaggtggct atgacagagc acaagatgtc agtgaagag    120 gtctgccgga aatacaacac agactgtgtg cagggtttga cccacagcaa agcccaggag    180
atcctggccc gggatgggcc taacgcactc acgccaccgc ctaccacccc agagtgggtc    240
aagttttgcc ggcagctctt cgggggcttc tccatcctgc tgtggatcgg ggctatcctc    300
tgcttcctgg cctacggtat ccaggcgggc accgaggacg accctctgg tgacaacctg    360 tacctgggca tcgtgctggc ggccgtggtg atcatcactg ctgcttctc ctactaccag    420 gaggccaaga gctccaagat catggagtcc ttcaagaaca tggtgcccca gcaagccctg    480
gtgatccggg aaggtgagaa gatgcaggtg aacgctgagg aggtggtggt cggggacctg    540
gtggagatca agggtggaga ccgagtgcca gctgacctgc ggatcatctc agcccacggc    600
tgcaaggtgg acaactcctc cctgactggc gaatccgagc cccagactcg ctctcccgac    660
tgcacgcacg acaacccctt ggagactcgg aacatcacct tcttttccac caactgtgtg    720
gaaggcacgc tcgggggcgt ggtggtgcc acgggcgacc gcactgtcat gggccgtatc    780
gccaccctgg catcagggct ggaggtgggc aagacgccca tcgccatcga gattgagcac    840
```

```
ttcatccagc tcatcaccgg cgtggctgtc ttcctgggtg tctccttctt catcctctcc    900
ctcattctcg gatacacctg gcttgaggct gtcatcttcc tcatcggcat catcgtggcc    960
aatgtcccag agggtctgct ggccactgtc actgtgtgtc tgacgctgac cgccaagcgc   1020
atggcccgga gaactgcct ggtgaagaac ctggaggctg tagaaaccct gggctccacg   1080
tccaccatct gctcagataa gacagggacc ctcactcaga accgcatgac agtcgcccac   1140
atgtggtttg acaaccagat ccacgaggct gacaccactg aggaccagtc agggacctca   1200
tttgacaaga gttcgcacac ctgggtggcc ctgtctcaca tcgctgggct ctgcaatcgc   1260
gctgtcttca agggtggtca ggacaacatc cctgtgctca gagggatgt ggctggggat   1320
gcgtctgagt ctgccctgct caagtgcatc gagctgtcct ctggctccgt gaagctgatg   1380
cgtgaacgca acaagaaagt ggctgagatt cccttcaatt ccaccaacaa ataccagctc   1440
tccatccatg agaccgagga ccccaacgac aaccgatacc tgctggtgat gaagggtgcc   1500
cccgagcgca tcctggaccg ctgctccacc atcctgctac agggcaagga gcagcctctg   1560
gacgaggaaa tgaaggaggc cttccagaat gcctaccttg agctcggtgg cctgggcgag   1620
cgcgtgcttg gtttctgcca ttattacctg cccgaggagc agttccccaa gggctttgcc   1680
ttcgactgtg atgacgtgaa cttcaccacg gacaacctct gctttgtggg cctcatgtcc   1740
atgatcgacc caccccgggc agccgtccct gacgcggtgg gcaagtgtcg cagcgcaggc   1800
atcaaggtca tcatggtcac cggcgatcac cccatcacgg ccaaggccat tgccaagggt   1860
gtgggcatca tctctgaggg caacgagact gtggaggaca tcgccgcccg gctcaacatt   1920
cccgtcagcc aggttaaccc ccgggatgcc aaggcctgcg tgatccacgg caccgacctc   1980
aaggacttca cctccgagca aatcgacgag atcctgcaga atcacaccga gatcgtcttc   2040
gcccgcacat ccccccagca gaagctcatc attgtggagg gctgtcagag acagggtgca   2100
attgtggctg tgaccgggga tggtgtgaac gactccccg ctctgaagaa ggccgacatt   2160
gggggtggcca tgggcatcgc tggctctgac gtctccaagc aggcagctga catgatcctg   2220
ctggacgaca actttgcctc catcgtcaca ggggtggagg agggccgcct gatcttcgac   2280
aacctaaaga gtccattgc ctacaccctg accagcaata tcccggagat cacgcccttc   2340
ctgctgttca tcatggccaa catcccgctg cccctgggca ccatcaccat cctctgcatc   2400
gatctgggca ctgacatggt ccctgccatc tcactggcgt acgaggctgc cgaaagcgac   2460
atcatgaaga gacagcccag gaacccgcgg acggacaaat tggtcaatga gagactcatc   2520
agcatggcct acgggcagat tggaatgatc caggctctcg gtggcttctt ctcttacttt   2580
gtgatcctgg cagaaaatgg cttcttgccc ggcaacctgg tgggcatccg gctgaactgg   2640
gatgaccgca ccgtcaatga cctggaagac agttacgggc agcagtggac atacgagcag   2700
aggaaggtgg tggagttcac ctgccacacg gccttctttg tgagcatcgt tgtcgtccag   2760
tgggccgatc tgatcatctg caagacccgg aggaactcgg tcttccagca gggcatgaag   2820
aacaagatcc tgatcttcgg gctgtttgag gagacggccc tggctgcctt cctgtcctac   2880
tgccccggca tggacgtggc cctgcgcatg taccctctca gcccagctg gtggttctgt   2940
gccttccccct acagtttcct catcttcgtc tacgacgaaa tccgcaaact catcctgcgc   3000
aggaacccag ggggttgggt ggagaaggaa acctactact ga                    3042
```

<210> SEQ ID NO 14
<211> LENGTH: 3090
<212> TYPE: DNA
<213> ORGANISM: homo sapiens

<400> SEQUENCE: 14

```
atgggcttt ggggaagaa agggacagtg gctccccatg accagagtcc aagacgaaga      60
cctaaaaaag ggcttatcaa gaaaaaaatg gtgaagaggg aaaaacagaa gcgcaatatg    120
gaggaactga agaaggaagt ggtcatggat gatcacaaat taaccttgga agagctgagc    180
accaagtact ccgtggacct gacaagggc catagccacc aaagggcaaa ggaaatcctg     240
actcgaggtg gacccaatac tgttacccca ccccccacca ctccagaatg ggtcaaattc    300
tgtaagcaac tgttcggagg cttctccctc ctactatgga ctggggccat tctctgcttt    360
gtggcctaca gcatccagat atatttcaat gaggagccta ccaaagacaa cctctacctg    420
agcatcgtac tgtccgtcgt ggtcatcgtc actggctgct tctcctatta tcaggaggcc    480
aagagctcca agatcatgga gtcttttaag aacatggtgc ctcagcaagc tctggtaatt    540
cgaggaggag agaagatgca aattaatgta caagaggtgg tgttgggaga cctggtggaa    600
atcaagggtg agaccgagt ccctgctgac ctccggctta tctctgcaca aggatgtaag     660
gtggacaact catccttgac tggggagtca gaaccccaga gccgctcccc tgacttcacc    720
catgagaacc ctctggagac ccgaaacatc tgcttctttt ccaccaactg tgtgaagga    780
accgcccggg gtattgtgat tgctacggga gactccacag tgatgggcag aattgcctcc    840
ctgacgtcag gctggcggt tggccagaca cctatcgctg ctgagatcga acacttcatc    900
catctgatca ctgtggtggc cgtcttcctt ggtgtcactt tttttgcgct ctcacttctc    960
ttgggctatg gttggctgga ggctatcatt tttctcattg gcatcattgt ggccaatgtg   1020
cctgaggggc tgttggctac agtcactgtg tgcctgaccc tcacagccaa gcgcatggca   1080
cggaagaact gcctggtgaa gaacctggag gcggtggaga cgctgggctc cacgtccacc   1140
atctgctcag acaagacggg caccctcacc cagaaccgca tgaccgtcgc ccacatgtgg   1200
tttgatatga ccgtgtatga ggccgacacc actgaagaac agactggaaa acatttacc    1260
aagagctctg atacctggtt tatgctggcc cgaatcgctg gcctctgcaa ccgggctgac   1320
tttaaggcta atcaggagat cctgcccatt gctaagaggg ccacaacagg tgatgcttcc   1380
gagtcagccc tcctcaagtt catcgagcag tcttacagct ctgtggcgga gatgagagag   1440
aaaaacccca aggtggcaga gattcccttt aattctacca acaagtacca gatgtccatc   1500
caccttcggg aggacagctc ccagacccac gtactgatga tgaagggtgc tccggagagg   1560
atcttggagt tttgttctac cttcttctg aatgggcagg agtactcaat gaacgatgaa   1620
atgaaggaag ccttccaaaa tgcctattta gaactgggag gtctggggga acgtgtgcta   1680
ggcttctgct tcttgaatct gcctagcagc ttctccaagg gattcccatt taatacagat   1740
gaaataaatt tccccatgga caaccttgt tttgtgggcc tcatatccat gattgaccct   1800
ccccgagctg cagtgcctga tgctgtgagc aagtgtcgca gtgcaggaat taaggtgatc   1860
atggtaacag agatcatcc cattacagct aaggccattg ccaagggtgt gggcatcatc   1920
tcagaaggca ctgagacggc agaggaagtc gctgcccggc ttaagatccc tatcagcaag   1980
gtcgatgcca gtgctgccaa agccattgtg gtgcatggtg cagaactgaa ggacatacag   2040
tccaagcagc ttgatcagat cctccagaac caccctgaga tcgtgtttgc tcggacctcc   2100
cctcagcaga agctcatcat tgtcgaggga tgtcagaggc tgggagccgt tgtggccgtg   2160
acaggtgacg gggtgaacga ctcccctgcg ctgaagaagg ctgacattgg cattgccatg   2220
ggcatctctg gctctgacgt ctctaagcag gcagccgaca tgatcctgct ggatgacaac   2280
```

-continued

| | |
|---|---|
| tttgcctcca tcgtcacggg ggtggaggag ggccgcctga tctttgacaa cctgaagaaa | 2340 |
| tccatcatgt acaccctgac cagcaacatc cccgagatca cgcccttcct gatgttcatc | 2400 |
| atcctcggta taccctgcc tctgggaacc ataaccatcc tctgcattga tctcggcact | 2460 |
| gacatggtcc ctgccatctc cttggcttat gagtcagctg aaagcgacat catgaagagg | 2520 |
| cttccaagga acccaaagac ggataatctg gtgaaccacc gtctcattgg catggcctat | 2580 |
| ggacagattg ggatgatcca ggctctggct ggattcttta cctactttgt aatcctggct | 2640 |
| gagaatggtt ttaggcctgt tgatctgctg ggcatccgcc tccactggga agataaatac | 2700 |
| ttgaatgacc tggaggacag ctacggacag cagtggacct atgagcaacg aaaagttgtg | 2760 |
| gagttcacat gccaaacggc cttttttgtc accatcgtgg ttgtgcagtg ggcggatctc | 2820 |
| atcatctcca agactcgccg caactcactt ttccagcagg gcatgagaaa caaagtctta | 2880 |
| atatttggga tcctggagga gacactcttg gctgcatttc tgtcctacac tccaggcatg | 2940 |
| gacgtggccc tgcgaatgta cccactcaag ataacctggt ggctctgtgc cattccctac | 3000 |
| agtattctca tcttcgtcta tgatgaaatc agaaaactcc tcatccgtca gcacccggat | 3060 |
| ggctgggtgg aaagggagac gtactactaa | 3090 |

<210> SEQ ID NO 15
<211> LENGTH: 963
<212> TYPE: DNA
<213> ORGANISM: Artificial sequence
<220> FEATURE:
<223> OTHER INFORMATION: Nucleic Acid sequence encoding His10-ATP1B1

<400> SEQUENCE: 15

| | |
|---|---|
| atggccagat cacatcatca ccatcaccac catcaccatc atcctaggag atctgcccgc | 60 |
| gggaaagcca aggaggaggg cagctggaag aaattcatct ggaactcaga gaagaaggag | 120 |
| tttctgggca ggaccggtgg cagttggttt aagatccttc tattctacgt aatatttat | 180 |
| ggctgcctgg ctggcatctt catcggaacc atccaagtga tgctgctcac catcagtgaa | 240 |
| tttaagccca catatcagga ccgagtggcc ccgccaggat taacacagat tcctcagatc | 300 |
| cagaagactg aaatttcctt tcgtcctaat gatcccaaga gctatgaggc atatgtactg | 360 |
| aacatagtta ggttcctgga aaagtacaaa gattcagccc agagggatga catgattttt | 420 |
| gaagattgtg gcgatgtgcc cagtgaaccg aaagaacgag agactttaa tcatgaacga | 480 |
| ggagagcgaa aggtctgcag attcaagctt gaatggctgg gaaattgctc tggattaaat | 540 |
| gatgaaactt atggctacaa agagggcaaa ccgtgcatta ttataaagct caaccgagtt | 600 |
| ctaggcttca aacctaagcc tcccaagaat gagtccttgg agacttaccc agtgatgaag | 660 |
| tataacccaa atgtccttcc cgttcagtgc actggcaagc gagatgaaga taaggataaa | 720 |
| gttggaaatg tggagtattt tggactgggc aactcccctg ttttcctct gcagtattat | 780 |
| ccgtactatg gcaaactcct gcagcccaaa tacctgcagc ccctgctggc cgtacagttc | 840 |
| accaatctta ccatggacac tgaaattcgc atagagtgta aggcgtacgg tgagaacatt | 900 |
| gggtacagtg agaaagaccg tttcaggga cgttttgatg taaaaattga agttaagagc | 960 |
| tga | 963 |

<210> SEQ ID NO 16
<211> LENGTH: 924
<212> TYPE: DNA
<213> ORGANISM: Artificial sequence
<220> FEATURE:
<223> OTHER INFORMATION: Nucleic Acid sequence encoding His10-ATP1B2

<400> SEQUENCE: 16

```
atggccagat cacatcatca ccatcaccac catcaccatc atcctaggag atctgtcatc    60
cagaaagaga agaagagctg cgggcaggtg gttgaggagt ggaaggagtt cgtgtggaac   120
ccgaggacgc accagtttat gggccgcacc gggaccagct gggcctttat cctcctcttc   180
tacctcgttt tttatgggtt ccccaccgcc atgttcaccc tcaccatgtg ggtgatgctg   240
cagactgtct ccgaccatac ccccaagtac caggaccgac tggccacacc gggcttgatg   300
attcgcccca agactgagaa ccttgatgtc attgtcaatg tcagtgacac tgaaagctgg   360
gaccagcatg ttcagaagct caacaagttc ttggagcctt acaacgactc tatgcaagcc   420
caaaagaatg atgtctgccg ccctgggcgc tattacgaac agccagataa tggagtcctc   480
aactacccca actggcctg ccaattcaac cggacccagc tgggcaactg ctccggcatt   540
ggggactcca cccactatgg ttacagcact gggcagccct gtgtcttcat caagatgaac   600
cgggtcatca acttctatgc aggagcaaac cagagcatga atgttacctg tgctgggaag   660
cgagatgaag atgctgagaa tctcggcaac ttcgtcatgt tccccgccaa cggcaacatc   720
gacctcatgt acttccccta ctatggcaaa aagttccacg tgaactacac acagcccctg   780
gtggctgtga gttcctgaa tgtgaccccc aacgtggagg tgaatgtaga atgtcgcatc   840
aacgccgcca acatcgccac agacgatgag cgagacaagt cgccggccg cgtggccttc   900
aaactccgca tcaacaaaac ctga                                          924
```

<210> SEQ ID NO 17
<211> LENGTH: 891
<212> TYPE: DNA
<213> ORGANISM: Artificial sequence
<220> FEATURE:
<223> OTHER INFORMATION: Nucleic Acid sequence encoding His10-ATP1B3

<400> SEQUENCE: 17

```
atggccagat cacatcatca ccatcaccac catcaccatc atcctaggag atctacgaag    60
aacgagaaga agtccctcaa ccagagcctg gccgagtgga agctcttcat ctacaacccg   120
accaccggag aattcctggg gcgcaccgcc aagagctggg gtttgatctt gctcttctac   180
ctagttttt atgggttcct ggctgcactc ttctcattca cgatgtgggt tatgcttcag   240
actctcaacg atgaggttcc aaaataccgt gaccagattc ctagcccagg actcatggtt   300
tttccaaaac cagtgaccgc attggaatat acattcagta ggtctgatcc aacttcgtat   360
gcagggtaca ttgaagacct taagaagttt ctaaaaccat atactttaga agaacagaag   420
aacctcacag tctgtcctga tggagcactt tttgaacaga agggtccagt ttatgttgca   480
tgtcagtttc ctatttcatt acttcaagca tgcagtggta tgaatgatcc tgattttggc   540
tattctcaag gaaacccttg tattcttgtg aaaatgaaca gaataattgg attaaagcct   600
gaaggagtgc caaggataga ttgtgtttca agaatgaag atataccaaa tgtagcagtt   660
tatcctcata tggaatgat agacttaaaa tatttcccat attatgggaa aaaactgcat   720
gttgggtatc tacagccatt ggttgctgtt caggtcagct tgctcctaa caacactggg   780
aaagaagtaa cagttgagtg caagattgat ggatcagcca acctaaaaag tcaggatgat   840
cgtgacaagt ttttgggacg agttatgttc aaaatcacag cacgtgcata g            891
```

<210> SEQ ID NO 18
<211> LENGTH: 288
<212> TYPE: DNA

```
<213> ORGANISM: Artificial sequence
<220> FEATURE:
<223> OTHER INFORMATION: Nucleic Acid sequence encoding Human His6-FXYD1

<400> SEQUENCE: 18
atgggcagca gccatcatca tcatcatcac tccgcgggtg aaaacctgta cttccagggt      60
accaaggcag aaagtccaaa ggaacacgac ccgttcactt acgactacca gtccctgcag     120
atcggaggcc tcgtcatcgc cgggatcctc ttcatcctgg gcatcctcat cgtgctgagc     180
agaagatgcc ggtgcaagtt caaccagcag cagaggactg gggaacccga tgaagaggag     240
ggaactttcc gcagctccat ccgccgtctg tccacccgca ggcggtag                  288

<210> SEQ ID NO 19
<211> LENGTH: 95
<212> TYPE: PRT
<213> ORGANISM: Artificial sequence
<220> FEATURE:
<223> OTHER INFORMATION: Amino Acid sequence encoding Human His6-FXYD1

<400> SEQUENCE: 19

Met Gly Ser Ser His His His His His His Ser Ala Gly Glu Asn Leu
1               5                   10                  15

Tyr Phe Gln Gly Thr Lys Ala Glu Ser Pro Lys Glu His Asp Pro Phe
            20                  25                  30

Thr Tyr Asp Tyr Gln Ser Leu Gln Ile Gly Gly Leu Val Ile Ala Gly
        35                  40                  45

Ile Leu Phe Ile Leu Gly Ile Leu Ile Val Leu Ser Arg Arg Cys Arg
    50                  55                  60

Cys Lys Phe Asn Gln Gln Gln Arg Thr Gly Glu Pro Asp Glu Glu Glu
65                  70                  75                  80

Gly Thr Phe Arg Ser Ser Ile Arg Arg Leu Ser Thr Arg Arg Arg
                85                  90                  95
```

SELECTIVE INHIBITORS OF ALPHA2-CONTAINING ISOFORMS OF NA,K-ATPASE AND USE THEREOF FOR REDUCTION OF INTRAOCULAR PRESSURE

RELATED APPLICATIONS

This application is a National Phase of PCT Patent Application No. PCT/IL2016/050785 having International filing date of Jul. 19, 2016, which claims the benefit of priority under 35 USC § 119(e) of U.S. Provisional Patent Application No. 62/302,226, filed on Mar. 2, 2016. PCT Patent Application No. PCT/IL2016/050785 is also a Continuation-in-Part (CIP) of PCT Patent Application No. PCT/IL2015/050741, having international filing date of Jul. 19, 2015. The contents of the above applications are all incorporated by reference as if fully set forth herein in their entirety.

SEQUENCE LISTING STATEMENT

The ASCII file, entitled 72096SequenceListing.txt, created on Jan. 17, 2018, comprising 73,501 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to pharmaceutical agents and, more particularly, but not exclusively, to digoxin and digitoxin derivatives exhibiting selective inhibition of α2-containing isoforms of Na,K-ATPase, and uses thereof to reduce intraocular pressure (IOP), and/or as cardiotonic agents in a subject in need thereof.

Glaucoma is a disease leading to irreversible blindness. Control of intraocular pressure (IOP) is the mainstay of current therapy of glaucoma, and is achieved by various drugs, such as β-blockers, prostaglandin analogues, α2 adrenergic receptor agonists, cholinergic agonists and carbonic anhydrase inhibitors given topically or systemically. The topical route is preferable, provided the drug effectively permeates the cornea, because this minimizes systemic side-effects. Despite the selection of drugs available, uncontrolled IOP in many patients eventually makes surgical intervention necessary. Thus, fresh approaches to drug treatment of glaucoma are highly desirable.

The Na,K-ATPase is the motor for production of the aqueous humour (bodily fluid) in the ciliary body epithelium and, in principle, inhibition of the Na,K-ATPase can suppress the production of aqueous humour, and control IOP. Control of: IOP is the mainstay of glaucoma therapy; however, the available drugs suffer from a variety of shortcomings, particularly due to systemic adverse effects and low therapeutic index. Previously, intra-venous digoxin, a classical inhibitor of the Na,K-pump, typically used primarily to treat congestive heart failure, was considered for this role but was discarded due to systemic toxicity.

Isoforins of the Na,K-ATPase ion pump consists of α and β subunits (α/β) and accessory FXYD regulatory subunits. There are four isoforms of the α1 subunit (α1-4) and three isoforms of the β subunit (β1-3) expressed in a tissue-specific fashion. The α1 isoform is the common isoform that maintains Na and gradients in all tissues, α2 is expressed mainly in muscle and astrocytes, and α3 is expressed mainly in nerve cells. For example, human heart expresses al (about 70%) and both α2 and α3 isoforms (about 30%) and β1.

The ciliary epithelium in the eye is a functional syncytium consisting of apical pigmented cells (PE) oriented towards the blood and baso-lateral non-pigmented (NPE) cells oriented towards the anterior chamber of the eye. It is known that the primary Na,K-ATPase isoform of the PE is α1β1 while that of the NPE is αβ3. The Na,K-ATPase in the NPE powers the production of the aqueous humor and controls intraocular pressure.

Thus, in principle, topically applied α2-selective cardiac glycosides that penetrate the intact eye and reach the ciliary epithelium could effectively reduce IOP. A potential advantage of topical application could be that systemic toxic effects typical of cardiac glycosides should be minimal.

Another possible application of an α2-selective cardiac glycoside could be as an effective cardiotonic drug, with reduced cardiotoxicity, compared to known drugs such as digoxin. Digitalis drugs such as digoxin have been used to treat heart failure for over two hundred years but are dangerous drugs with multiple side effects. There is now good evidence that selective inhibition of α2 is especially effective in enhancing cardiac excitation-contraction coupling and mediating cardiac glycoside-mediated positive inotropy. Inhibition of α2, which is a minor isoform and is located largely in T-tubules, may mediate the positive cardiotonic effects, but α2-selective cardiac glycosides should only minimally inhibit α1, located primarily in the outer sarcolemma membrane, and thus avoid cellular Ca overload, the hallmark of cardiac toxicity.

The isoform selectivity of a large number of known cardiac glycosides has been previously studied, using the yeast *P. pastoris* expressing Na,K-ATPase isofoinis (α1β1, α2β1, α3β1), and purified detergent-soluble isoform complexes of Na,K-ATPase [Cohen E. et al., 2005, *J Biol Chem*, 280(17), pp. 16610-16618; Flaviv H, et al., 2007, *Biochemistry*, 46(44), pp. 12855-12867; Lifshitz Y, et al, 2007, *Biochemistry*, 46(51), pp. 14937-14950; Mishra N K, et al., 2011, *J Biol Chem*, 286(11), pp. 9699-9712; and Kapri-Pardes E, et al., 2011, *J Biol Chem*, 286(50), pp. 42888-42899].

Dissociation constants, $K_D$, for digitalis glycosides, digoxin and digitoxin, measured by $^3$H-ouabain displacement assays in membranes, showed moderate selectivity (3-4-fold) for α2/α3 over α1. By contrast to the digitalis glycosides, the $K_D$ of ouabain showed some preference for α1 over α2 and similar Ki values for all three isoforms. In assays of inhibition of Na,K-ATPase activity, measured with the purified isoform protein complexes, digoxin and digitoxin showed 3-4-fold lower Ki (inhibition) values for α2 compared to α1, with α3 more similar to α1. No aglycones of any cardiac glycosides tested showed isoform selectivity. For digoxin derivatives, with one to four digitoxose moieties the maximal α2/α1 selectivity was found for digoxin itself, with three digitoxose sugars [Katz, A. et al., *J Biol Chem*, 2010, 285(25), pp. 19582-19592].

Based on recent studies [Laursen, M. et al., *Prot Nati Acad Sci USA*, 2015, 112(6):1755-60], it was inferred that the sugar moiety of digoxin likely determines isoform selectivity, which is generally consistent with recent structures of Na,K-ATPase with bound ouabain, bufalin or digoxin. The unsaturated lactone ring and steroid portion of ouabain are bound between trans-membrane segments M1, M4, M5 of the α subunit, in which there are no amino-acid differences between isoforms. Assuming that the aglycones of all cardiac glycosides bind similarly, the implication is that isoforms cannot discriminate between any of the aglycones, as found experimentally. By contrast, the sugar is bound near extracellular loops, where there are a number of amino-acid differences between the isoforms. These residues might interact with the sugars of bound digoxin in an isoform-selective way.

Additional background art include WO 2015/029035, WO 2007/079128, WO 2010/053771, U.S. Patent Application No. 2005/0032138 and U.S. Pat. Nos. 7,888,059 and 7,851,145; these documents are hereby incorporated by reference.

SUMMARY OF THE INVENTION

According to an aspect of some embodiments of the present invention there is provided a compound represented by general Formula I:

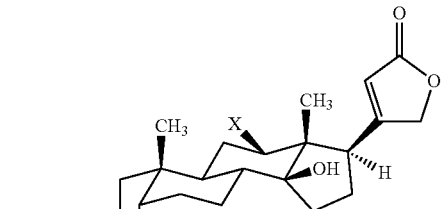

Formula I including any pharmaceutically acceptable salt, prodrug, hydrate, solvate, enantiomer and diastereomer thereof, and any mixtures thereof,
wherein:
X is H or OH;
R is represented by general Formula II;

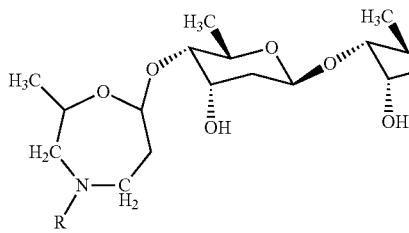

Formula II

A is a spacer moiety or a covalent bond; and
B is a cyclic moiety;
or
B is selected from the group consisting of an alkylsulfonyl, an arylsulfonyl and a sulfonamide;
or
B is —NR$_1$R$_2$, wherein R$_1$ and R$_2$ are each independently H or a C$_1$-C$_4$ alkyl provided that at least one of R$_1$ and R$_2$ is a C$_1$-C$_4$ alkyl.

According to some embodiments of the invention, A is selected from the group consisting of a covalent bond, an unsubstituted C$_1$-C$_6$ alkyl, a substituted C$_1$-C$_6$ alkyl, an unsubstituted C$_1$-C$_6$ alkyl interrupted by one or more heteroatom and a substituted C$_1$-C$_6$ alkyl interrupted by one or more heteroatom.

According to some embodiments of the invention, B is a cyclic moiety selected from the group consisting of an unsubstituted alicyclic moiety, a substituted alicyclic moiety, an unsubstituted heterocyclic moiety, a substituted heterocyclic moiety, an unsubstituted aryl moiety, a substituted aryl moiety, an unsubstituted heteroaryl moiety and a substituted heteroaryl moiety.

According to some embodiments of the invention, B is an unsubstituted alicyclic moiety.

According to some embodiments of the invention, the unsubstituted alicyclic moiety is selected from the group consisting of cyclopropyl, cyclobutyl, cyclopentyl, to cyclohexyl and cycloheptyl.

According to some embodiments of the invention, B is a substituted alicyclic moiety.

According to some embodiments of the invention, the substituted alicyclic moiety is selected from the group consisting of 2,3-dimethylcyclopropane-1-yl, 3,3-dimethylcyclobutane-1-yl, 3,4-dimethylcyclopentane-1-yl and 3,5-dimethylcyclohexane-1-yl.

According to some embodiments of the invention, B is an unsubstituted heterocyclic moiety.

According to some embodiments of the invention, the unsubstituted heterocyclic moiety is selected from the group consisting of oxiranyl, aziridinyl, oxetanyl, azetidinyl, thietanyl, tetrahydrofuranyl, pynrolidinyl, tetrahydropyranyl and piperidinyl.

According to some embodiments of the invention, B is an unsubstituted aryl moiety.

According to some embodiments of the invention, the unsubstituted aryl moiety is selected from the group consisting of cyclopentadienyl, phenyl and naphthyl.

According to some embodiments of the invention, B is an unsubstituted heteroaryl moiety.

According to some embodiments of the invention, the unsubstituted heteroaryl moiety is imidazolyl.

According to some embodiments of the invention, the alkylsulfonyl is selected from the group consisting of methylsufonyl, ethylsulfonyl and is isopropylsulfonyl.

According to some embodiments of the invention, the arylsulforryl is selected from the group consisting of phenylsulfonyl, benzylsulfonyl and tosyl.

According to some embodiments of the invention, the sulfonamide is selected from the group consisting of methylsulfonamide, N-methylmethanesulfonamide and N,N-dimethylmethanesulfonamide.

According to some embodiments of the invention, B is —N(Et)$_2$.

According to some embodiments of the invention, X is H.

According to some embodiments of the invention, A is a covalent bond and B is cyclobutyl.

According to some embodiments of the invention, A is —CH$_2$— and B is cyclopropyl.

According to some embodiments of the invention, X is OH.

According to some embodiments of the invention, A is a covalent bond and B is selected from the group consisting of cyclopropyl, cyclobutyl, cyclopentyl, cyclohexyl.

According to some embodiments of the invention, A is —CH$_2$— and B is selected from the group consisting of cyclopropyl, 3,3-dimethylcyclobutane-1-yl and phenyl.

According to some embodiments of the invention, A is —(CH$_2$)$_2$— and B is cyclopropyl.

According to some embodiments of the invention, R is selected from the group consisting of cyclopropyl, methylcyclopropane, ethylcyclopropane, propylcyclopropane, cyclobutyl, methylcyclobutane, methyl-3,3-dimethylcyclobutane, ethylcyclobutane, propylcyclobutane, cyclopentyl, methylcyclopentane, ethylcyclopentane, propylcyclopentane, cyclohexyl, azetidinyl, oxetanyl, thietanyl, histaminyl and benzyl.

According to some embodiments of the invention, R is selected from the group consisting of cyclopropyl, methylcyclopropane and cyclobutyl.

According to some of any of the embodiments of the invention, the compound is having an affinity to at least one isoform of Na,K-ATPase.

According to some embodiments of the invention, the isoform is selected from the group consisting of α1β1, α1β2, α1β3, α2β1, α2β2, α2β3, α3β1, α3β2, α3β3, α4β1, α4β2 and α4β3.

According to some embodiments of the invention, the affinity of the compound to any one of α2β1, α2β2 and α2β3 is higher than the affinity to α1β1, α1β2, α1β3, α3β1, α3β2, α3β3, α4β1, α4β2 and α4β3 by at least 100%.

According to some embodiments of the invention, the affinity of the compound to any one of α2β1, α2β2 and α2β3 is higher than the affinity to α1β1 by at least 300% (4-fold).

According to some embodiments of the invention, the affinity of the compound to α2β3 is higher than the affinity to α1β1 by at least 500 (6-fold).

According to some embodiments of the invention, the compound is having a α2β3 inhibition constant (Ki) lower than 10 nM.

According to an aspect of some embodiments of the present invention there is provided a pharmaceutical composition that includes as an active ingredient a compound according to any of the embodiments of the invention and a pharmaceutically acceptable carrier.

According to some embodiments of the invention, the pharmaceutical composition is packaged in a packaging material and identified in print, or on the packaging material, for use in reducing intraocular pressure (IOP).

According to some embodiments of the invention, the pharmaceutical composition is packaged in a packaging material and identified in print, or on the packaging material, for use in a treatment of a heart condition.

According to an aspect of some embodiments of the present invention there is provided a method of reducing intraocular pressure (IOP) in a subject in need thereof, which includes administering to the subject a therapeutically effective amount of a compound according to any of the embodiments of the invention, or a pharmaceutical composition to according to some of the embodiments of the invention.

According to an aspect of some embodiments of the present invention there is provided a method of treating a heart condition in a subject in need thereof, that includes administering to the subject a therapeutically effective amount of a compound according to any of the embodiments of the invention, or a pharmaceutical composition according to some of the embodiments of the invention.

According to an aspect of some embodiments of the present invention there is provided a use of a compound according to any of the embodiments of the invention, or a pharmaceutical composition according to some of the embodiments of the invention, for the manufacture of a medicament for reducing intraocular pressure (IOP).

According to an aspect of some embodiments of the present invention there is provided a use of a compound according to any of the embodiments of the invention, or a pharmaceutical composition according to some of the embodiments of the invention, for the manufacture of a medicament for treating a heart condition.

According to some embodiments of the invention, the heart condition is selected from the group consisting of atrial fibrillation, atrial flutter, mitral stenosis, chronic heart failure and congestive heart failure.

According to an aspect of some embodiments of the present invention there is provided a pharmaceutical composition that includes as active ingredients:

at least one ingredient selected from the group consisting of a prostaglandin analog, a β-blocker, an adrenergic agent, an α2-adrenergic receptor agonist, a miotic agent, a carbonic anhydrase inhibitor and a cholinergic agonist; and a compound represented by Formula III:

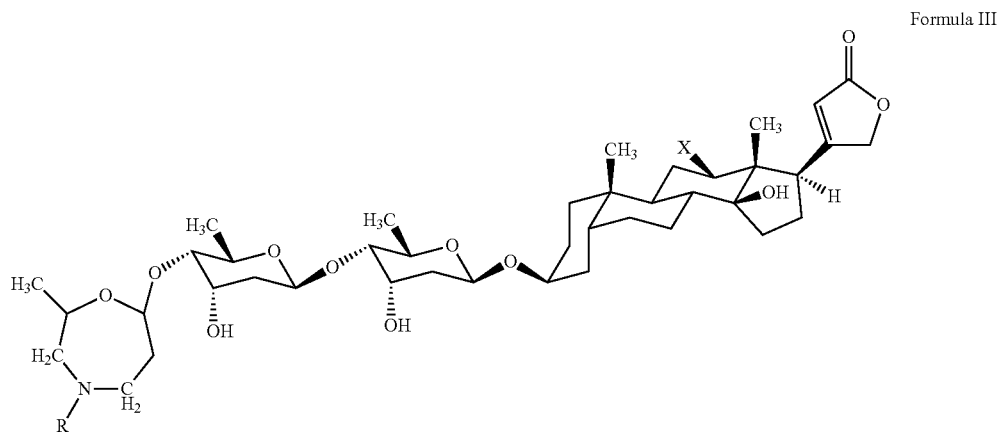

Formula III including any pharmaceutically acceptable salt, prodrug, hydrate, solvate, enantiomer and diastereomer thereof, and any mixtures thereof, and a pharmaceutically acceptable carrier, wherein:

X is H or OH;

R' is selected from the group consisting of OH, $C_1$-$C_6$ alkyl, $C_1$-$C_6$ haloalkyl ($C_1$-$C_6$ alkyl substituted with at least one halo), —$(CR^bR^c)nSi(R^a)_3$, —$(CR^bR^c)n$-C(=Y)—$NR_1R_2$, —$(CR^bR^c)n$-C(=Y)—NHOH, —$(CR^dR^e)n$-C(=Y)—$COOR_3$, —NHC(=Y)$NR_1R_2$ and —$(CR^bR^c)n$-$NH_2$;

Y is O or S;

R1, R2 and R3 are each independently H or a $C_1$-$C_4$ alkyl;

Ra is a $C_1$-$C_4$ alkyl;

Rb, Rc and Rd are each independently selected from H, a $C_1$-$C_4$ alkyl and a $C_1$-$C_4$ hydroxyalkyl;

Re is selected from a $C_1$-$C_4$ alkyl and a $C_1$-$C_4$ hydroxyalkyl; and n is 0, 1 or 2;

or R' is represented by general Formula II:

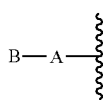

Formula II

A is a spacer moiety or a covalent bond; and

B is a cyclic moiety, or B is selected from the group consisting of an alkylsulfonyl, an arylsulfonyl and a sulfonamide, or B is —$NR_1R_2$, wherein $R_1$ and R2 are each independently H or a $C_1$-$C_4$ alkyl provided that at least one of $R_1$ and $R_2$ is a $C_1$-$C_4$ alkyl, and a pharmaceutically acceptable carrier.

According to some embodiments of the invention, the pharmaceutical composition is packaged in a packaging material and identified in print, or on the packaging material, for use in reducing intraocular pressure (IOP).

According to an aspect of some embodiments of the present invention there is provided a use of an agent selected from the group consisting of a prostaglandin analog, a β-blocker, an adrenergic agent, an α2-adrenergic receptor agonist, a miotic agent, a carbonic anhydrase inhibitor and a cholinergic agonist, and a compound represented by Formula III.

including any pharmaceutically acceptable salt, prodrug, hydrate, solvate, enantiomer and diastereomer thereof, and any mixtures thereof, wherein:

X is H or OH;

R' is selected from the group consisting of OH, $C_1$-$C_6$ alkyl, $C_1$-$C_6$ haloalkyl ($C_1$-$C_6$ alkyl substituted with at least one halo), —$(CR^bR^c)nSi(R^a)_3$, —$(CR^bR^c)n$-C(=Y)—$NR_1R_2$, —$(CR^bR^c)n$-C(=Y)—NHOH, —$(CR^dR^e)n$-C(=Y)—$COOR_3$, —NHC(=Y)$NR_1R_2$ and —$(CR^bR^c)n$-$NH_2$;

Y is O or S;

R1, R2 and R3 are each independently H or a $C_1$-$C_4$ alkyl;

Ra is a C1-C4 alkyl;

Rb, Re and Rd are each independently selected from H, a $C_1$-$C_4$ alkyl and a $C_1$-$C_4$ hydroxyalkyl;

Re is selected from a $C_1$-$C_4$ alkyl and a $C_1$-$C_4$ hydroxyalkyl; and n is 0, 1 or 2;

or R' is represented by general Formula II:

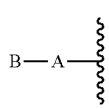

Formula II

A is a spacer moiety or a covalent, bond; and

B is a cyclic moiety, or B is selected from the group consisting of an alkylsulfonyl, an arylsulfonyl and a sulfonamide, or B is —$NR_1R_2$, wherein $R_1$ and $R_2$ are each independent r a $C_1$-$C_4$ alkyl provided that at least one of $R_1$ and $R_2$ is a $C_1$-$C_4$ alkyl, for the manufacture of a medicament for reducing intraocular pressure (IOP).

According to an aspect of some embodiments of the present invention there is provided a method of reducing intraocular pressure (IOP) in a subject in need thereof, which includes co-administering to the subject a therapeutically effective amount of:

an agent selected from the group consisting of a prostaglandin analog, a (β-blocker, an adrenergic agent, an α2-adrenergic receptor agonist, a miotic agent, a carbonic anhydrase inhibitor and a cholinergic agonist; and

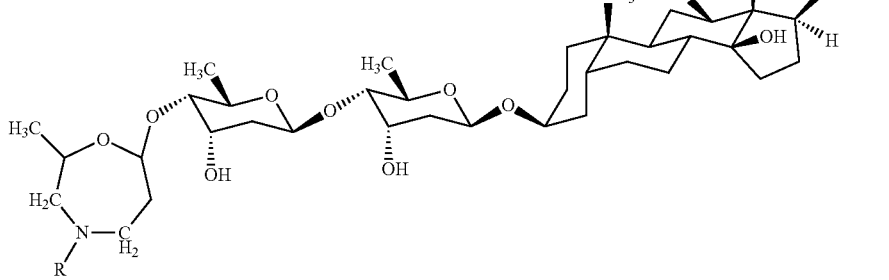

Formula III a compound represented by Formula III:

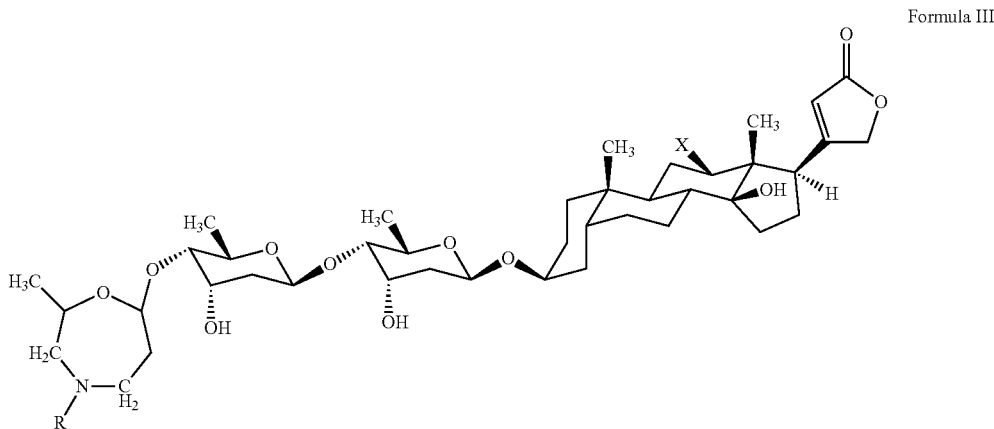

Formula III including any pharmaceutically acceptable salt, prodrug, hydrate, solvate, enantiomer and diastereomer thereof, and any mixtures thereof, wherein:

X is H or OH;

R' is selected from the group consisting of OH, $C_1$-$C_6$ alkyl, $C_1$-$C_6$ haloalkyl ($C_1$-$C_6$ alkyl substituted with at least one halo), —$(CR^bR^c)nSi(R^a)_3$, —$(CR^bR^c)n$-C(=Y)—$NR_1R_2$, —$CR^bR^c)n$-C(=Y)—NHOH, —$(CR^dR^c)n$-C(=Y)—$COOR_3$, —NHC(=Y)$NR_1R_2$ and —$(CR^bR^c)n$-$NH_2$;

Y is O or S;

$R_1$, $R_2$ and $R_3$ are each independently H or a $C_1$-$C_4$ alkyl;

Ra is a $C_1$-$C_4$ alkyl;

Rb, Rc and Rd are each independently selected from H, a $C_1$-$C_4$ alkyl and a $C_1$-$C_4$ hydroxyalkyl;

Re is selected from a $C_1$-$C_4$ alkyl and a $C_1$-$C_4$ hydroxyalkyl; and n is 0, 1 or 2;

or R' is represented by general Formula II:

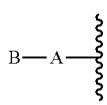

Formula II

A is a spacer moiety or a covalent bond; and

B is a cyclic moiety, or B is selected from the group consisting of an alkylsulfonyl, an arylsulfonyl and a sulfonamide, or B is —$NR_1R_2$, wherein $R_1$ and $R_2$ are each independently H or a $C_1$-$C_4$ alkyl provided that at least one of $R_1$ and $R_2$ is a $C_1$-$C_4$ alkyl.

According to some embodiments of the invention, the mode of administration is effected topically, extraocularly, intraocularly and/or intravitreally.

According to some embodiments of the invention, the composition according to some embodiments of the invention is formulated as an ophthalmic composition suitable for topical, extraocular, intraocular and/or intravitreal administration to the eye of the subject.

According to some embodiments of the invention, the composition according to some embodiments of the invention is in the form selected from the group consisting of an eye-drop solution, a spray, an eye wash solution, an ointment, a suspension, a gel, a cream and an injectable solution.

According to some embodiments of the invention, the intraocular pressure (IOP) is associated with glaucoma, low-tension glaucoma and normal-tension glaucoma.

According to an aspect of some embodiments of the present invention there is provided a method of treating a heart condition in a subject in need thereof, that includes co-administering to the subject a therapeutically effective amount of:

an agent selected from the group consisting of a β-blocker, an anticoagulation agent, an angiotensin-converting-enzyme inhibitor and an angiotensin II receptor antagonist; and a compound represented by Formula III:

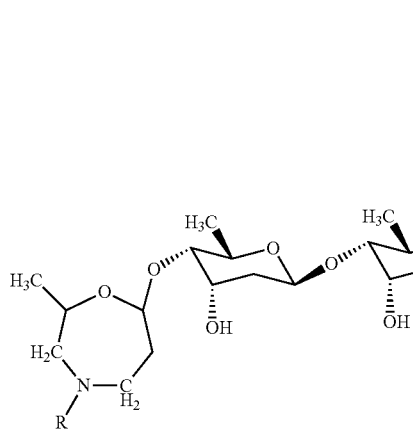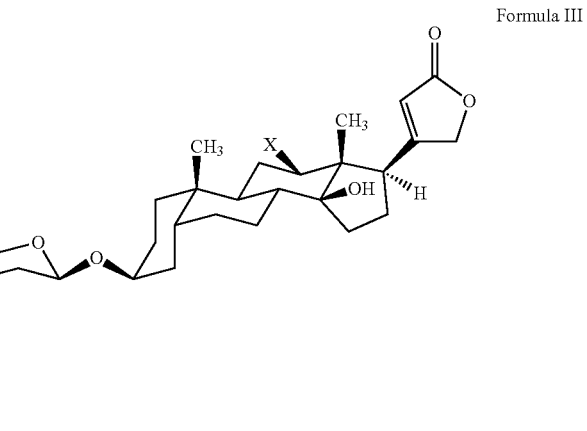

Formula III including any pharmaceutically acceptable salt, prodrug, hydrate, solvate, enantiomer and diastereomer thereof, and any mixtures thereof, wherein:

X is H or OH;

R' is selected from the group consisting of OH, $C_1$-$C_6$ alkyl, $C_1$-$C_6$ haloalkyl ($C_1$-$C_6$ alkyl substituted with at least one halo), —$(CR^bR^c)nSi(R^a)_3$, —$(CR^bR^c)n$-$C(=Y)$—$NR_1R_2$, —$(CR^bR^c)n$-$C(=Y)$—$NHOH$, —$(CR^dR^e)n$-$C(=Y)$—$COOR_3$, —$NHC(=Y)NR_1R_2$ and —$(CR^bR^c)n$-$NH_2$;

Y is O or S;

$R_1$, $R_2$ and $R_3$ are each independently H or a $C_1$-$C_4$ alkyl;

Ra is a $C_1$-$C_4$ alkyl;

Rb, Rc and Rd are each independently selected from H, a $C_1$-$C_4$ alkyl and a $C_1$-$C_4$ hydroxyalkyl;

Re is selected from a $C_1$-$C_4$ alkyl and a $C_1$-$C_4$ hydroxyalkyl; and n is 0, 1 or 2;

or R' is represented by general Formula II:

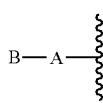

Formula II

A is a spacer moiety or a covalent bond; and

B is a cyclic moiety, or B is selected from the group consisting of an alkylsulfonyl, an arylsulfonyl and a sulfonamide, or B is —$NR_1R_2$, wherein $R_1$ and $R_2$ are each independently H or a $C_1$-$C_4$ alkyl provided that at least one of $R_1$ and $R_2$ is a $C_1$-$C_4$ alkyl.

According to an aspect of some embodiments of the present invention there is provided a process of preparing a compound according any of the embodiments of the invention, the process includes:

converting the third digitoxose moiety of digoxin or digitoxin into a dialdehyde; and reacting the dialdehyde with a reagent represented by general formula IV:

B-A-$NH_2$    Formula IV

A is a spacer moiety or a covalent bond; and

B is a cyclic moiety, or B is selected from the group consisting of an alkylsulfonyl, an arylsulfonyl and a sulfonamide, or B is —$NR_1R_2$, wherein $R_1$ and $R_2$ are each independently H or a $C_1$-$C_4$ alkyl provided that at least one of $R_1$ and $R_2$ is a $C_1$-$C_4$ alkyl.

According to some embodiments of the invention, converting the third digitoxose moiety of digoxin or digitoxin into a dialdehyde is effected by sodium periodate ($NaIO_4$).

According to some embodiments of the invention, reacting the dialdehyde with a reagent represented by general formula IV is effected in the presence of $NaCNBH_3$.

According to an aspect of some embodiments of the present invention there is provided a method of determining an affinity of a compound, according to any embodiment of the invention, to at least one isoform of Na,K-ATPase, the method includes contacting the isoform of Na,K-ATPase with the compound in an affinity measurement setup and determining the affinity.

According to an aspect of some embodiments of the present invention there is provided a method of isolating an isoform of Na,K-ATPase of a mammal, that includes:

transforming yeast cells with a clone that that includes an a chain sequence and a β chain sequence of the Na,K-ATPase;

expressing the clone in the yeast cells; and isolating the isoform, wherein:

the α chain sequence is selected from e group consisting of α1, α2, α3 and α4; and the β chain sequence is selected from the group consisting of β1, β2 and β3.

According to some embodiments of the invention, the isoform is selected from the group consisting of α1β1, α1β2, α1β3, α2β1, α2β2, α2β3, α3β1, α3β2, α3β3, α4β1, α4β2 and α4β3.

According to some embodiments of the invention, the isoform is α2β2.

According to some embodiments of the invention, the isoform is a α2β3.

According to an aspect of some embodiments of the present invention there is provided an isolated isoform of Na,K-ATPase of a mammal having at least 70% purity, wherein the isoform is α2β2.

According to an aspect of some embodiments of the present invention there is provided an isolated isoform of Na,K-ATPase of a mammal having at least 70% purity, wherein the isoform is α2β3.

According to an aspect of some embodiments of the present invention there is provided an isolated isoform of Na,K-ATPase of a mammal having a yeast-characterizing glycosylation pattern, wherein the isoform is α2β2.

According to an aspect of some embodiments of the present invention there is provided an isolated isoform of Na,K-ATPase of a mammal having a yeast-characterizing glycosylation pattern, wherein the isoform is α2β3.

According to some embodiments of the invention, the isolated isoform, according to any embodiment of the invention, is human.

According to some embodiments of the invention a prodrug of the compound is represented by Formula V:

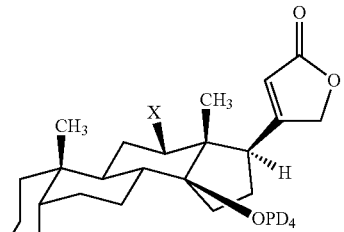
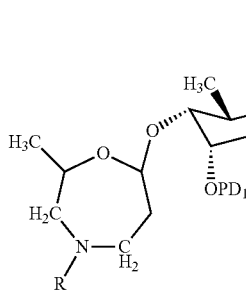

Formula V wherein X is H or $PD_3$, and each of $PD_1$-$PD_4$ is H or independently selected from the group consisting of a methoxymethyl ether, a tetrahydropyranyl ether, a t-butyl ether, an allyl ether, a benzyl ether, a t-butyldimethylsilyl ether, a t-butyldiphenylsilyl ether, an acetic acid ester (Ac), ethyl, propyl, butyl, t-butyl or pivalic acid ester and a benzoic acid ester, provided that at least one of $PD_1$-$PD_4$ is not H.

According to some embodiments, each of $PD_1$-$PD_4$ is an acetic acid ester (Ac).

According to some embodiments, each of $PD_1$ and $PD_2$ is an acetic acid ester (Ac).

According to some embodiments, each of $PD_1$-$PD_3$ is an acetic acid ester (Ac).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A, 1B, 1C and 1D present comparative plots of IOP as a function of time, showing the dose response of α2-inhibitor compounds, according to some embodiments of the present invention, in lowering IOP in live rabbits, wherein FIG. 1A shows the results obtained for DiB, FIG. 1B shows the duration of the effect of DiB while 4AP is added every 2 hours so as to maintain the raised IOP, FIG. 1C shows the results obtained for DMcP, and FIG. 1D shows the results obtained for DcB;

FIGS. 2A, 2B, 2C and 2D present comparative plots of IOP as a function of time, demonstrating the capacity of the α2-inhibitor compounds, according to some embodiments of the present invention, to lower IOP below basal levels compared to a buffer control when administered topically to one eye of a rabbit, while the other eye received PBS as a control, wherein FIG. 2A shows the lack of effect of digoxin, FIG. 2B shows the lack of effect of DiB (a non-cyclic moiety inhibitor), FIG. 2C shows the notable effect of DMcP, and FIG. 2D shows the notable effect of DcB;

FIGS. 3A, 3B and 3C present comparative plots of IOP as a function of time, demonstrating the effect of α2-inhibitor compounds, according to some embodiments of the present invention, to potentiate the drug Latanoprost in lowering IOP below basal levels, wherein FIG. 3A shows the effect of DcB alone, FIG. 3B shows the effect of Latanoprost alone, and FIG. 3C shows the effect of co-administering DcB with Latanoprost.

DESCRIPTION OF SPECIFIC EMBODIMENTS OF THE INVENTION

Figures 3A, 3B, 3C:
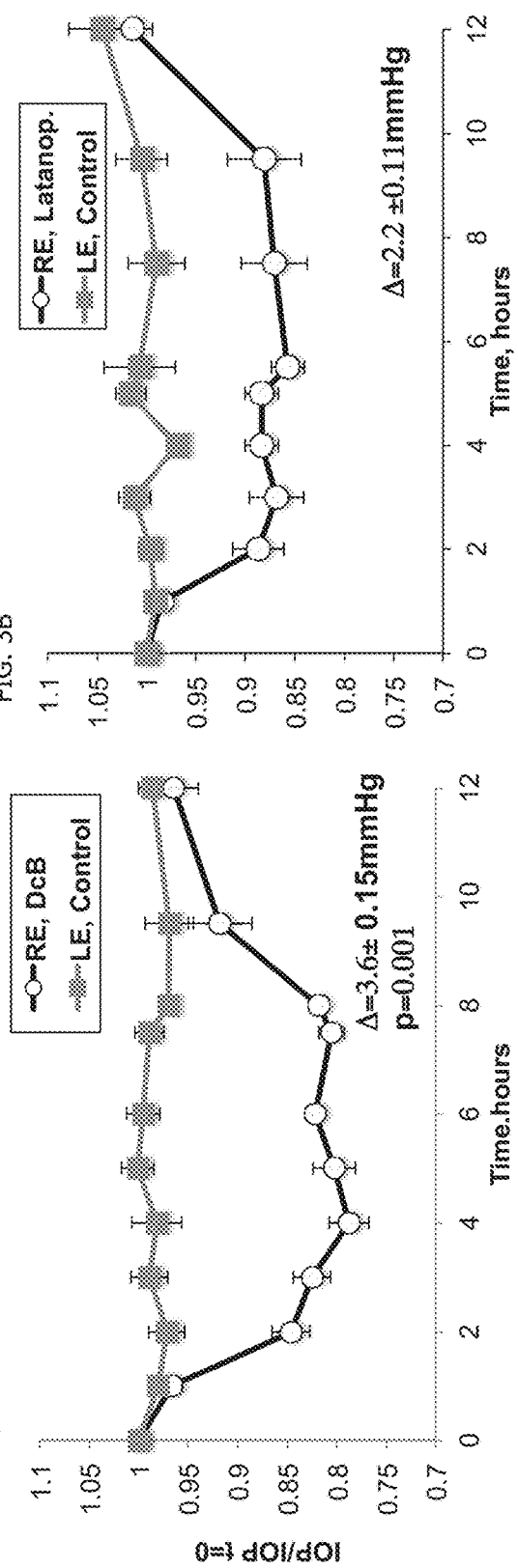

The present invention, in some embodiments thereof, relates to a pharmaceutical agents and, more particularly, but not exclusively, to digoxin and digitoxin derivatives exhibiting selective inhibition of α2-containing isoforms of Na,K-

ATPase, and uses thereof to reduce intraocular pressure (IOP), and/or as cardiotonic agents in a subject in need thereof.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of to description and should not be regarded as limiting.

As discussed hereinabove, Na,K-ATPase inhibitors that exhibit selectivity towards tissue-specific isoforms of the protein, present pharmaceutical advantages such as broader therapeutic window and wider scope of modes of administration. For example, Na,K-ATPase inhibitors exhibiting selectivity towards protein isoforms containing the α2 sub-unit offer this advantages over unselective inhibitors in treating medical conditions wherein lowering the intraocular pressure is called for.

While searching for α2-selective inhibitors, the present inventors have surprisingly found that certain derivatives of digoxin and digitoxin, wherein the perhydro-1-4-oxazepine moiety thereof is N-substituted with a cyclic moiety, exhibit a notable selectivity towards α2-containing isoform of Na,K-ATPase.

Compounds:

According to an aspect of some embodiments of the present invention there is provided a compound represented by general Formula I:

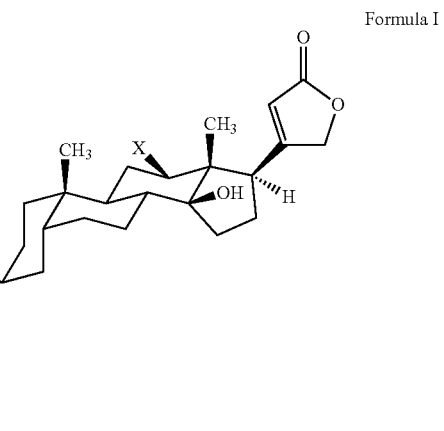

Formula I wherein:

X is H or OH, whereas derivatives having X=H are referred to as digitoxin derivatives, and derivatives having X=—OH are referred to as digoxin derivatives;

R is represented by general Formula II:

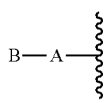

Formula II the wiggled line represents the N-link to the compound;
A is a spacer moiety or a covalent bond; and
B is a cyclic moiety;
or
R is represented by general Formula II:

Formula II the wiggled line represents the N-link to the compound;
A is a spacer moiety or a covalent bond; and
B is selected from the group consisting of an alkylsulfonyl, an arylsulfonyl and a sulfonamide;
or
R is represented by general Formula II:

Formula II the wiggled line represents the N-link to the compound;
A is a spacer moiety or a covalent, bond; and
B is —NR$_1$R$_2$, wherein R$_1$ and R$_2$ are each independently H or a C$_1$-C$_4$ alkyl provided that at least one of R$_1$ and R$_2$ is a C$_1$-C$_4$ alkyl, namely B is a secondary amine or tertiary amine.

As used herein, the term "cyclic moiety" refers to a group of atoms that are covalently attached to one another so as to form at least one ring of atoms. Non-limiting examples of cyclic moieties include unsubstituted alicyclic moieties, substituted alicyclic moieties, unsubstituted heterocyclic moieties, substituted heterocyclic moieties, unsubstituted aryl moieties, substituted aryl moieties, unsubstituted heteroaryl moiety and substituted heteroaryl moieties.

A substituted cyclic moiety has one or more chemical group or atom attached to one of the atoms in the ring of atoms. Examples of such chemical groups or atoms include, without limitation, C$_1$-C$_6$ alkyl, hydroxyl, amine, halo, alkoxy, carboxyl, amide and the like, or a second cyclic moiety attached by a covalent bond(s) to one or two of the ring atoms of the cyclic moiety.

The terms "hydroxyl" or "hydroxy", as used herein, refer to an —OH group.

As used herein, the term "amine" describes a —NR$^1$R$^2$ group where each of R$^1$ and R$^2$ is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low (or lower) alkyl, having 1-4 carbon atoms (namely, methyl, ethyl, propyl and butyl).

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms.

A $C_1$-$C_6$ alkyl group refers to any one of the moieties methyl, ethyl, n-propyl, i-propyl, n-butyl, s-butyl, i-butyl, t-butyl, n-pentyl, t-pentyl, neopentyl, i-pentyl, s-pentyl, 3-pentyl, n-hexyl, 2-methylpentyl, 3-methylpentyl, 2,2-dimethylbutyl and 2,3-dimethylbutyl.

The term "halide", as used herein, refers to the anion of a halo atom, i.e. F$^-$, Cl$^-$, Br$^-$ and I$^-$.

The term "halo" refers to F, Cl, Br and I atoms as substituents.

The term "alkoxy" refers to an —OR$^1$ group, wherein R$^1$ is as defined herein, but other than hydrogen.

The term "amide" as used herein encompasses C-amide and N-amide.

The term "C-amide" describes a —C(=O)—NR$^1$R$^2$ group, where R$^1$ and R$^2$ are as defined herein.

The term "N-amide" describes a R$^1$C(=O)—NR$^2$— group, where R$^1$ and R$^2$ are as defined herein.

The term alkylsulfonyl and arylsulfonyl refers to an R$^1$—S(=O)$_2$— group, wherein R$^1$ is as defined herein, but other than hydrogen. Examples of arylsulfonyl groups include p-toluenesulfonyl (tosyl; Ts), p-bromobenzenesulfonyl (brosyl; Bs), 2- or 4-nitrobenzenesulfonyl (nosyl; Ns), methanesulfonyl (mesyl; Ms), trifluoromethanesulfonyl (triflyl; Tf), and 5-(dimethylamino)naphthalene-1-sulfonyl (Dansyl; Ds).

The term solnfonamide refers to an R$^3$—S(=O)$_2$— group, wherein R$^3$ is amine as defined herein.

The terms "Acyclic" and "cycloalkyl", refer to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. The cycloalkyl can be substituted or unsubstituted.

Examples of alicyclic moieties include, without limitation, cyclopropyl, cyclobutyl, cyclopentyl, cyclohexyl, cycloheptyl and cyclododecyl, Examples of substituted alicyclic is selected from the group consisting of 2,3-dimethylcyclopropane-1-yl, 3,3-dimethylcyclobutane-1-yl, 3,4-dimethylcyclopentane-1-yl and 3,5-dimethylcyclohexane-1-yl.

The terms "heterocyclic" or "heteroalicyclic", as used herein, describe a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Representative examples are morpholine, piperidine, piperazine, tetrahydrofurane, tetrahydropyrane and the like.

In some embodiments, the heterocyclic moiety is selected from the group consisting of oxiranyl, aziridinyl, oxetanyl, azetidinyl, tetrahydrofuranyl, pyrrolidinyl, tetrahydropyranyl and piperidinyl.

The term "aryl" describes an all-carbon monocyclic or fused-ring polycyclic (i.e., rings which share adjacent pairs of carbon atoms) groups having a completely conjugated pi-electron system, as in the example of phenyl. The aryl group may be unsubstituted or substituted by one or more substituents. Examples of aryls include cyclopentadienyl, phenyl and naphthyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl moieties include pyrrole, furane, thiophene, imidazole, oxazole, thiazole, pyrazole, pyridine, pyrimidine, quinoline, isoquinoline, purine, thiadiazole, indole and the like. The heteroaryl group may be unsubstituted or substituted by one or more substituents.

According to some embodiments, the spacer moiety A can be a covalent bond, an unsubstituted, $C_1$-$C_6$ alkyl, a substituted, $C_1$-$C_6$ alkyl, an unsubstituted $C_1$-$C_6$ alkyl interrupted by one or more heteroatom (e.g., O, N or S) and a substituted $C_1$-$C_6$ alkyl interrupted by one or more heteroatom. A spacer moiety may be substituted with one or more $C_1$-$C_6$ alkyl, hydroxyl, amine, halo, alkoxy, carboxyl, amide and the like.

In some embodiments, A is a covalent bond and B an alicyclic moiety such as, for example, cyclopropyl, cyclobutyl, cyclopentyl, cyclohexyl, and the corresponding R in Formula I is:

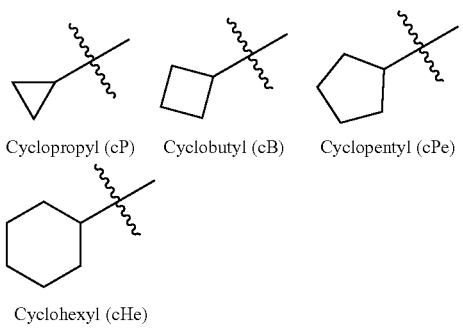

Cyclopropyl (cP)    Cyclobutyl (cB)    Cyclopentyl (cPe)

Cyclohexyl (cHe)

In some embodiments, A is a covalent bond and B a heteroalicyclic moiety such as, for example, cyclopropyl, cyclobutyl, cyclopentyl, cyclohexyl, and the corresponding R in Formula I is:

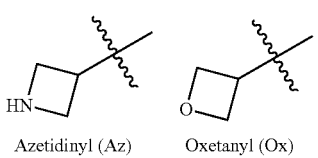

Azetidinyl (Az)    Oxetanyl (Ox)

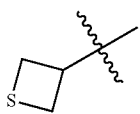

Thietanyl (Th)

In some embodiments, A is —CH₂— and B a cyclic moiety such as, for example, cyclopropyl, 3,3-dimethylcyclobutane-1-yl and phenyl, and the corresponding R in Formula I is:

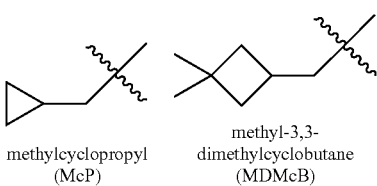

methylcyclopropyl (McP)    methyl-3,3-dimethylcyclobutane (MDMcB)

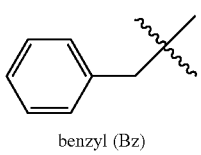

benzyl (Bz)

In some embodiments, A is —(CH₂)₂— and B a cyclic moiety such as, for example, cyclopropyl, and the corresponding R in Formula I is:

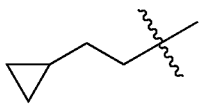

Ethylcyclopropane (EcP)

In some embodiments, A is —(CH₂)₂— and B a heteroaryl cyclic moiety such as, for example, imidazolyl, and the corresponding R in Formula I is:

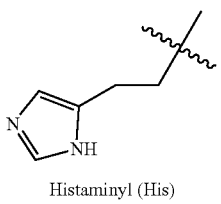 [SMILES: *CCc1cnc[nH]1]

Histaminyl (His)

In some embodiment, X is H, A is a covalent bond and B is cyclobutyl,

In some embodiment, X is H, A is —CH₂— and B is cyclopropyl.

In some embodiment, X is OH, A is a covalent bond and B is cyclopropyl, cyclobutyl, cyclopentyl or cyclohexyl.

In some embodiment, X is OH, A is —CH₂— and B is cyclopropyl, 3,3-dimethylcyclobutane-1-yl and phenyl.

In some embodiment, X is OH, A is —CH₂— and B is cyclopropyl.

In some embodiments, R of general Formula I is cyclopropyl, methylcyclopropane, ethylcyclopropane, propylcyclopropane, cyclobutyl, methylcyclobutane, methyl-3,3-dimethylcyclobutane, ethylcyclobutane, propylcyclobutane, cyclopentyl, methylcyclopentane, ethylcyclopentane, propylcyclopentane, cyclohexyl and benzyl. Alternatively, R is cyclopropyl, methylcyclopropane and cyclobutyl.

In some embodiments, A is —CH₂— and B an alkylsulfonyl such as, for example, methylsulfonyl, and the corresponding R in Formula I is:

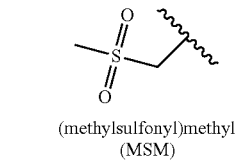

(methylsulfonyl)methyl (MSM)

In some embodiments, A is —(CH₂)₂— and B an alkylsulfonyl such as, for example, methylsulfonyl, or a solnfmamide, and the corresponding R in Formula I is:

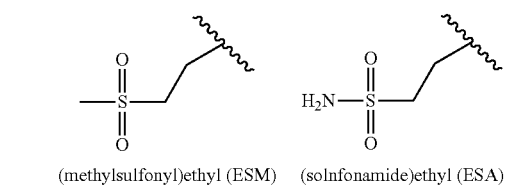

(methylsulfonyl)ethyl (ESM)    (solnfonamide)ethyl (ESA)

In some embodiments, A is —(CH₂)₂— and B a tertiary amine such as, for example, N,N-dimethylamine, and the corresponding R in Formula I is:

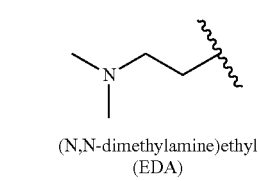 [SMILES: *CCN(C)C]

(N,N-dimethylamine)ethyl (EDA)

In some embodiments, the compound is any one of the structures presented below:

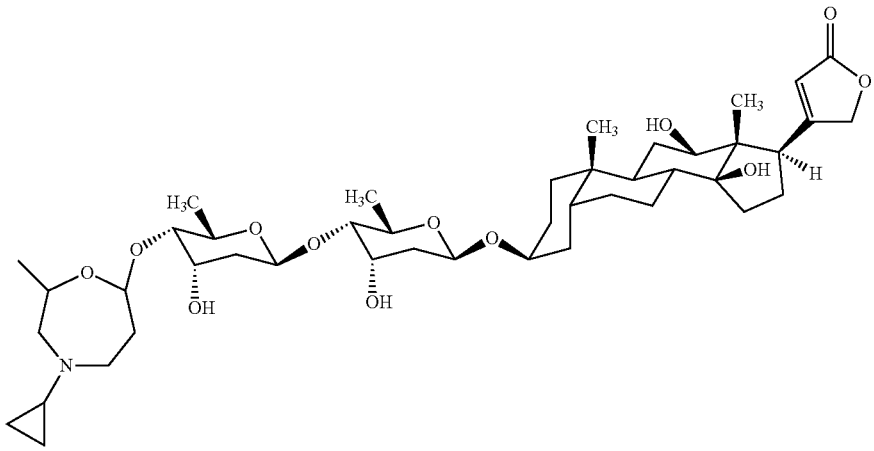

DcP or 4-((3S,5R,8R,9S,10S,12R,13S,14S,17R)-3-(((2R, 4S,5S,6R)-5-(((2S,4S,5S,6R)-5-((4-cyclopropyl-2-methyl-1, 4-oxazepan-7-yl)oxy)-4-hydroxy-6-methyltetrahydro-2H-pyran-2-yl)oxy)-4-hydroxy-6-methyltetrahydro-2H-pyran-2-yl)oxy)-12,14-dihydroxy-10,13-dimethythylhexadecahydro-1H-cyclopenta[a]phenanthren-17-yl)furan-2(5H)-one;

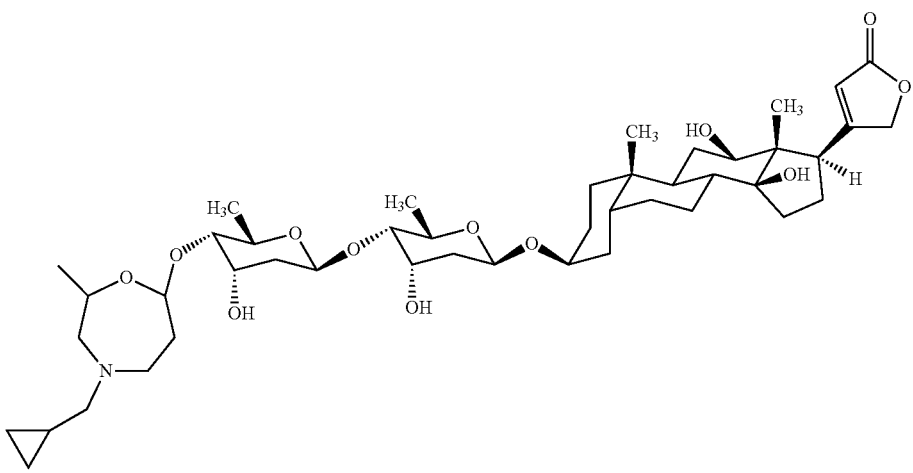

DMcP or 4-((3S,5R,8R,9S,10S,12R,13S,14S,17R)-3-(((2R,4S,5S,6R)-5-(((2S,4S,5S,6R)-5-((4-cyclopropylmethyl)-2-methyl-1,4-oxazepan-7-yl)oxy)-4-hydroxy-6-methyltetrahydro-2H-pyran-2-yl)oxy)-4-hydroxy-6-methyltetrahydro-2H-pyran-2-yl)oxy)-12,14-dihydroxy-10, 13-dimethylhexadecahydro-1H-cyclopenta[a]phenanthren-17-yl)furan-2(5H)-one;

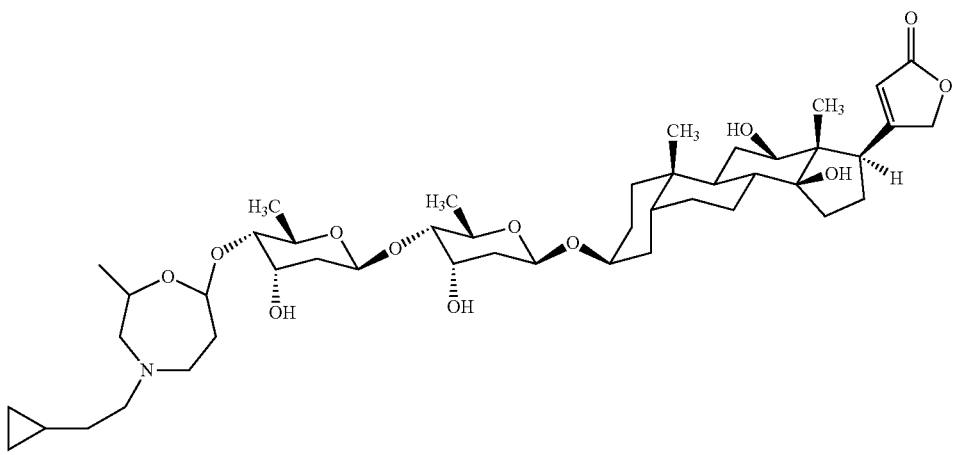

DEcP or 4((3S,5R,8R,9S,10S,12R,13S,14S,17R)-3-(((2S,4S,5R,6R)-5-(((2S,4S,5S,6R)-5-(2-cyclopropylethyl)-2-methyl-1,4-oxazepan-7-yl)oxy)-4-hydroxy-6-methyltetrahydro-2H-pyran-2-yl)oxy)-4-hydroxy-6-methyltetrahydro-2H-pyran-2-yl)oxy)-12,14-dihydroxy-10,13-dimethylhexadecahydro-1H-cyclopenta[a]phenanthren-17-yl)furan-2(5H)-one;

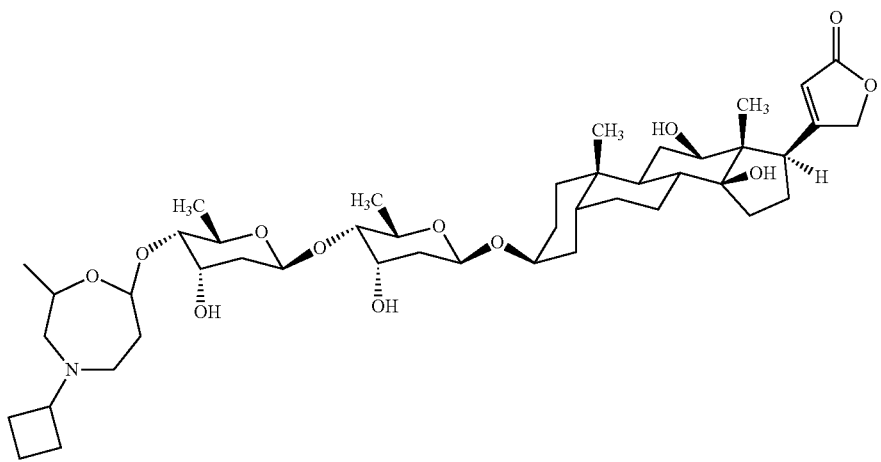

DcB or 4((3S,5R,8R,9S,10S,12R,13S,14S,17R)-3-(((2R,4S,5S,6R)-5-4(2S,4S,5S,6R)-5-((4-cyclobutyl-2-methyl-1,4-oxazepan-7-yl)oxy)-4-hydroxy-6-methyltetrahydro-2H-pyran-2-yl)oxy)-4-hydroxy-6-methyltetrahydro-2H-pyran-2-yl)oxy)-12,14-dihydroxy-10,13-dimethythexadecahydro-1H-cyclopenta[a]phenanthren-17-yl)furan-2(5H)-one;

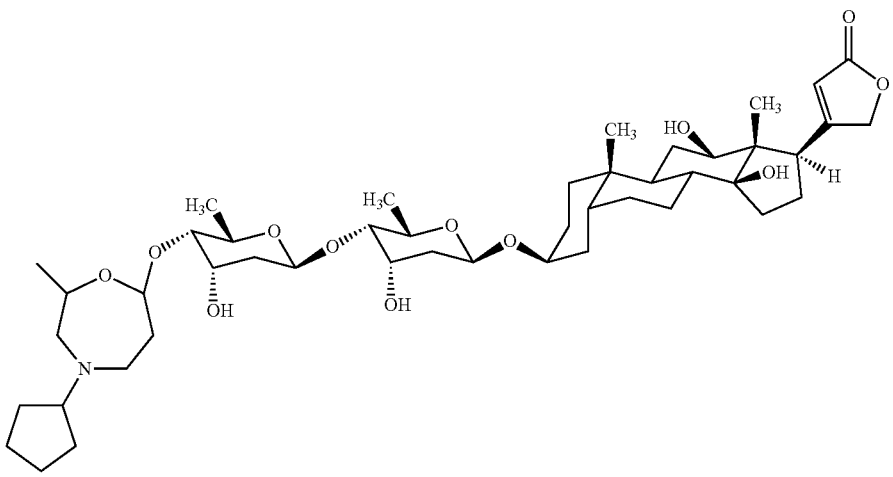

DcPe or 4-((3S,5R,8R,9S,10S,12R,13S,14S,17R)-3-(((2S,4S,5R,6R)-5-(((2S,4S,5S,6R)-5-((4-cyclopentyl-2-methyl-1,4-oxazepan-7-yl)oxy)-4-hydroxy-6-methyltetrahydro-2H-pyran-2-yl)oxy)-4-h ydroxy-6-methyltetrahydro-2H-pyran-2-yl)oxy)-12,14-dihydroxy-10,13-dimethylhexadecahydro-1H-cyclopenta[a]phenanthren-17-yl)furan-2(5H)-one;

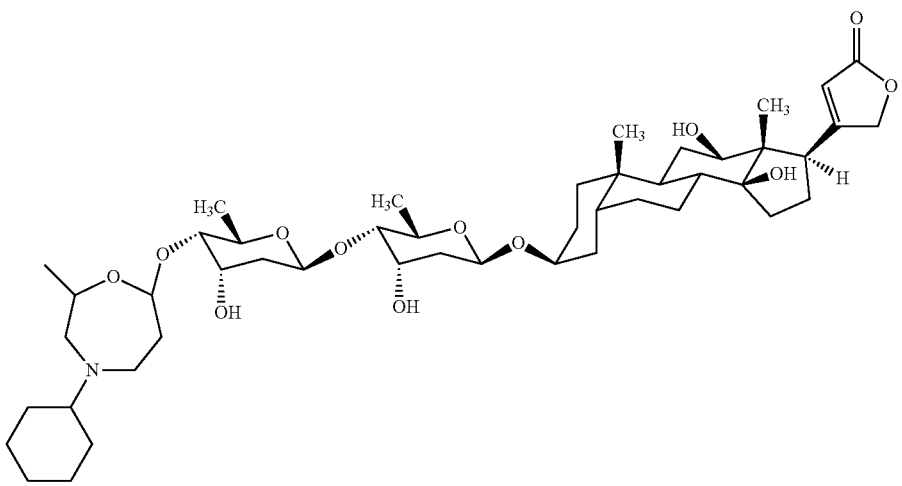

DcHe or 4-((3S,5R,8R,9S,10S,12R,13S,14S,17R)-3-(((2S,4S,5R,6R)-5-(((2S,4S,5S,6R)-5((4-cyclohexyl-2-methyl-1,4-oxazepan-7-yl)oxy)-4-h ydroxy-6-methyltetrahydro-2H-pyran-2-yl)oxy)-4-hydroxy-6-methyltetrahydro-2H-pyran-2-yl)oxy)-12,14-dihydroxy-10,13-dimethylhexadecahydro-1H-cyclopenta[a]phenanthren-17-yl)furan-2(5H)-one;

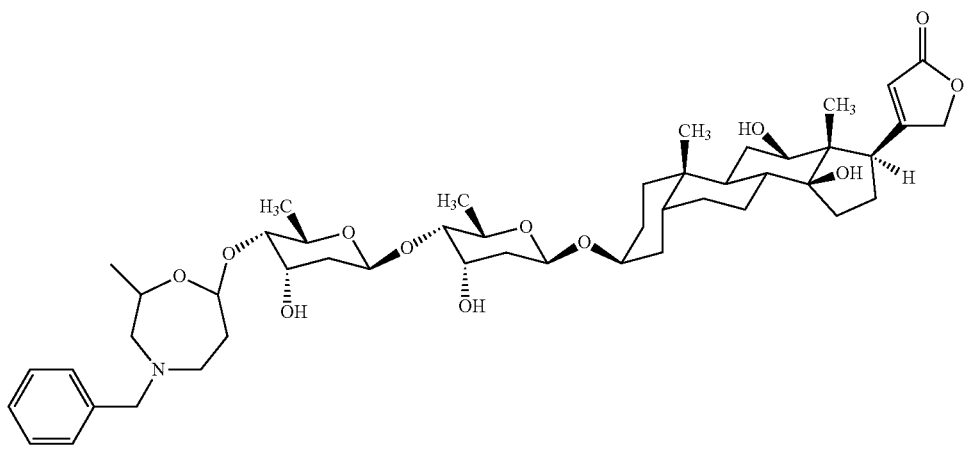

DBz or 4-(3S,5R,8R,9S,10S,12R,13S,14S,17R)-3-(((2S,4S,5R,6R)-5-(((2S,4S,5S,6R)-5 ((4-benzyl-2-methyl-1,4-oxazepan-7-yl)oxy)-4-hydroxy-6-methyltetrahydro-2H-pyran-2-ypoxy)-4-hydroxy-6-methyltetrahy dro-2H-pyran-2-yl)oxy)-12,14-dihydroxy-10,13-dimethythexadecahydro-1H-cyclopenta[a]phenanthren-17-yl)furan-2(5H)-one;

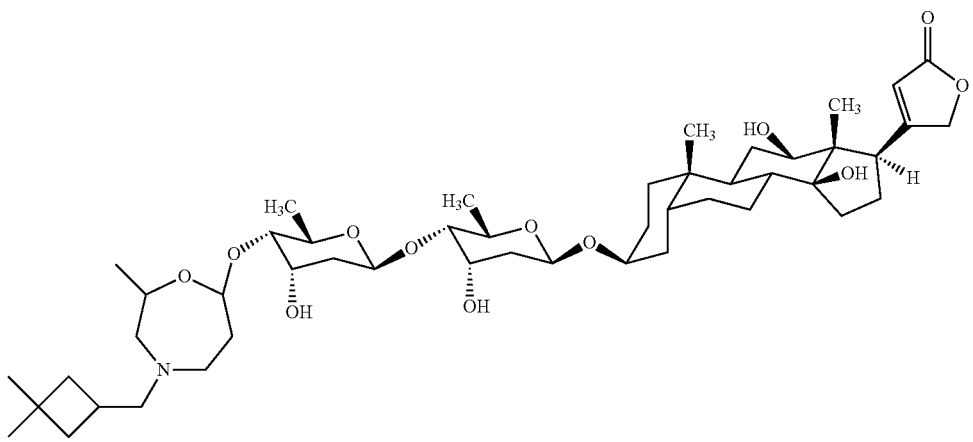

DMDMcB or 4-((3S,5R,8R,9S10S,12R,13S,14S,17R)-3-(((2S,4S,5R,6R)-5-(((2S,4S,5S,6R)-5-((4-((3,3-dimethylcyclobutyl)methyl)-2-methyl-1,4-oxazepan-7-yl)oxy)-4-hydroxy-6-methyltetrahydro-2H-pyran-2-yl)oxy)-4-hydroxy-6-methyltetrahydro-2H-pyran-2-yl)oxy)-12,14-dihydroxy-10,13-dimethylhexadecahydro-1H-cyclopenta[a]phenanthren-17-yl)furan-2(5H)-one;

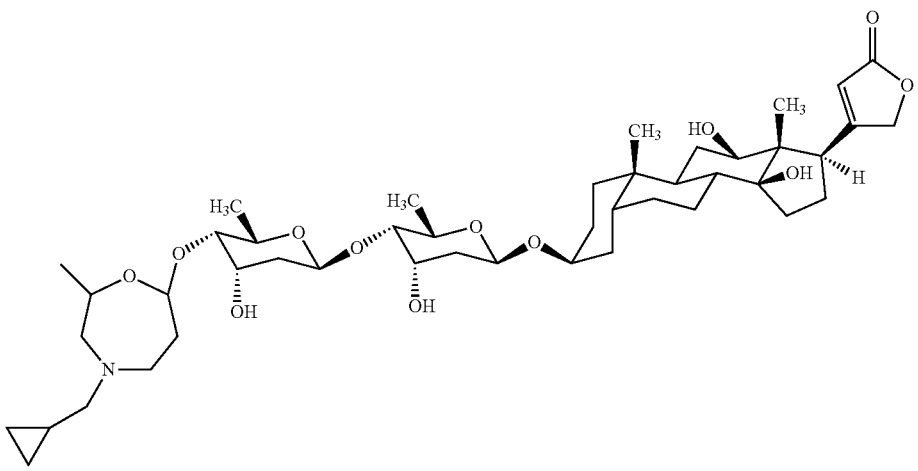

DtxMcP or 4-((3S,5R,8R,9S,10S,13R,14S,17R)-3-(((2S,4S,5R,6R)-5-(((2S,4S,5S,6R)-5-((4-(cyclopropylmethyl)-2-methyl-1,4-oxazepan-7-ypoxy)-4-h ydroxy-6-methyltetrahydro-2H-pyran-2-yl)oxy)-4-hydroxy-6-methyltetrahydro-2H-pyran-2-yl)oxy)-14-hydroxy-10,13-dimethylhexadecahydro-1H-cyclopenta[a]phenanthren-17-yl)furan-2(5H)-one;

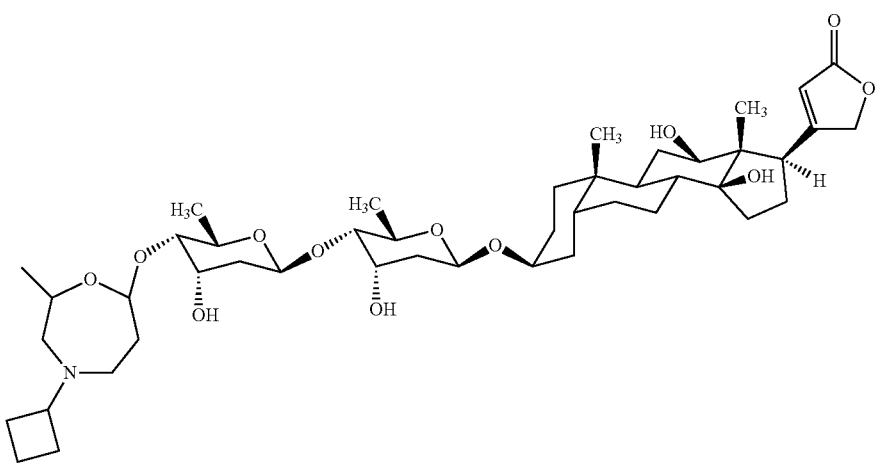

DtxcB or 4-((3S,5R,8R,9S,10S,13R,14S,17R)-3-(((2S,4S,5R,6R)-5-(((2S,5S,6R)-5-((4-cyclobutyl-2-methyl-1,4-oxazepart-7-yl)oxy)-4-hydroxy-6-methyltetrahydro-2H-pyran-2-yl)oxy)-4-hydroxy-6-methyltetrahydro-2H-pyran-2-yl)oxy)-14-hydroxy-10,13-dimethylhexadecahydro-1H-cyclopenta[a]phenanthren-17-yl)furan-2(5H)-one;

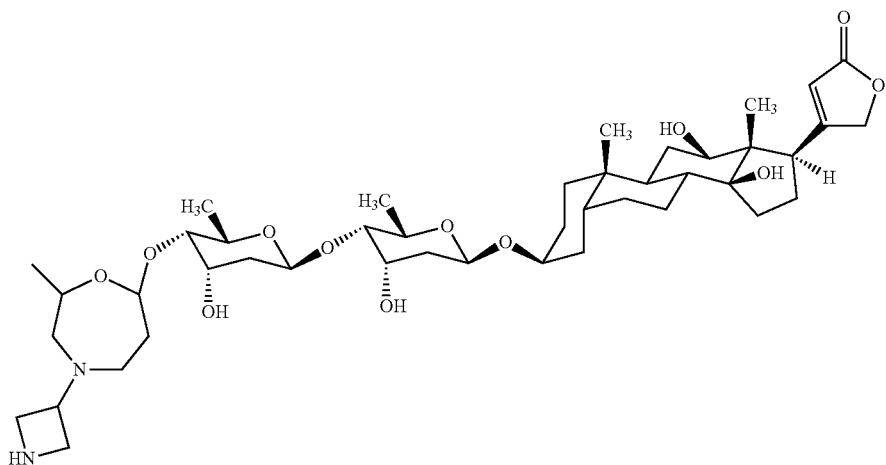

DAz or 4-((3S,5R,8R,9S,10S,12R,13S,14S,17R)-3-(((2R4S,5S,6R)-5-(((2S,4S,5S,6R)-5-((4-(azetidin-3-yl)-2-methyl-1,4-oxazepan-7-yl)oxy)-4-hydroxy-6-methyltetrahydro-2H-pyran_-2-yl)oxy)-4-hydroxy-6-methyltetrahydro-2H-pyran-2-yl)oxy)-12,14-dihydroxy-10,13-dimethylhexadeathydro-1H-cyclopenta[a]phenanthren-17-yl)furan-2(5H)-one;

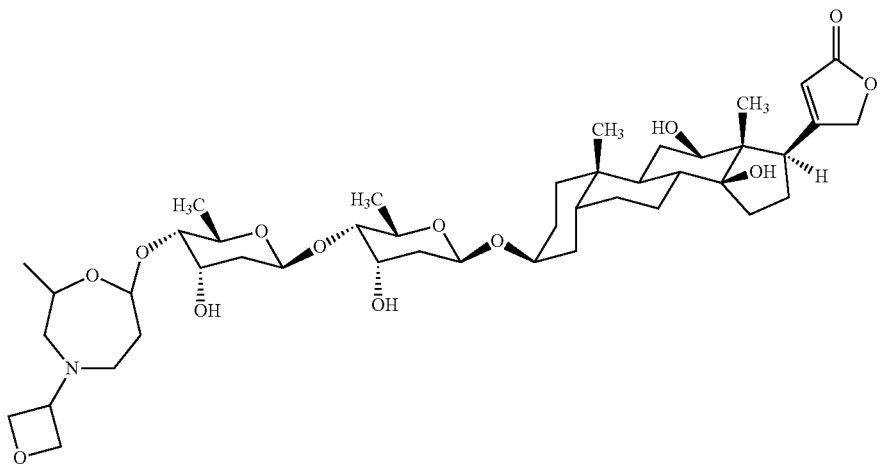

DOx or 4-((3S,5R,8R,9S,10S,12R,13S,14S,17R)-12,14-dihydroxy-3-(((2R,4S,5S,6R)-4-hydroxy-5-(((2S,4S,5S,6R)-4-hydroxy-6-methyl-54((2-methyl-4-(oxetan-3-yl)-1,4-oxazepan-7-yl)oxy)tetrahydro-2H-pyran-2-yl)oxy)-6-methyltetrahydro-2H-pyran-2-yl)oxy)-10,13-dimethylhexadecahydro-1H-cyclopenta[a]phenanthren-17-yl)furan-2(5H)-one;

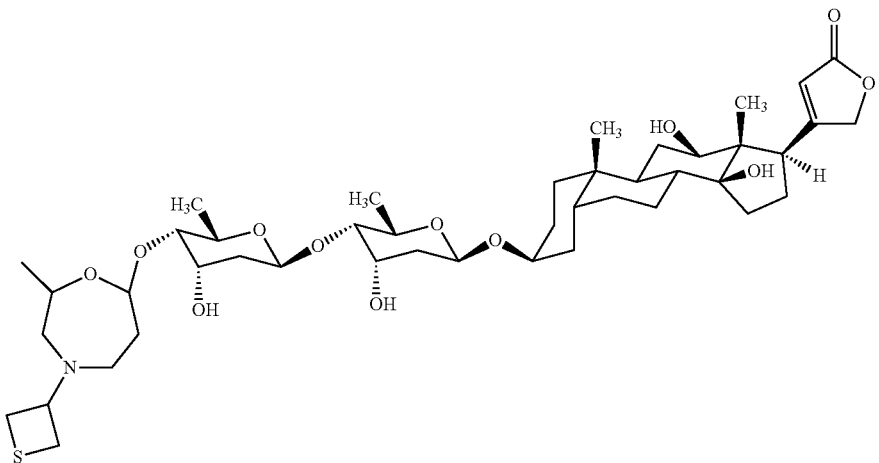

DTh or 4-((3S,5R,8R,9S,10S,12R,13S,14S,17R)-12,14-dihydroxy-3-(((2R,4S,5S,6R)-4-hydroxy-5-4(((2S,4S,5S,6R)-4-hydroxy-6-methyl-5-((2-methyl-4-(thietan-3-yl)-1,4-oxazepan-7-yl)oxy)tetrahydro-2H-pyran-2-yl)oxy)-6-methyltetrahydro-2H-pyran-2-yl)oxy)-10,13-dimethylhexadecahydro-1H-cyclopentatallphenanthren-17-yl)furan-2(5H)-one; and

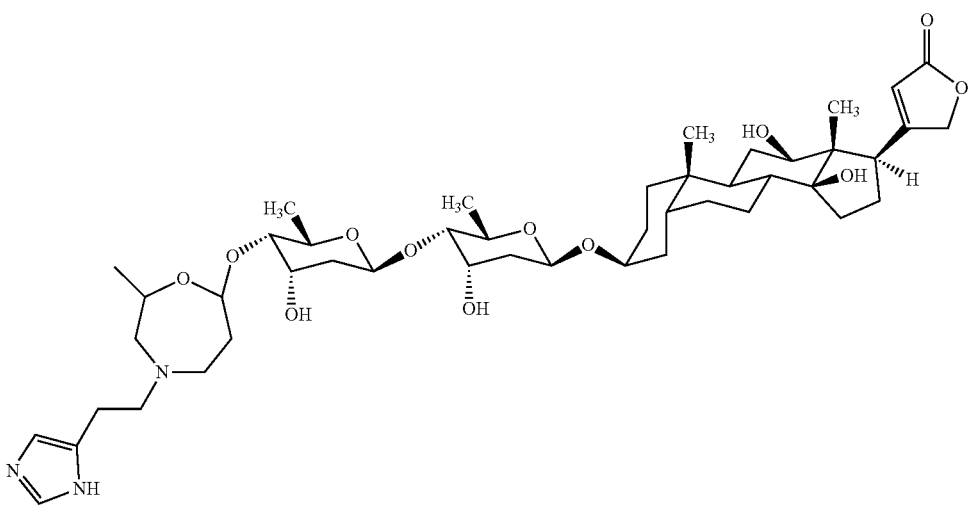

DHis or 4-((3S,5R,8R,9S,10S,12R,13S,14S,17R)-3-(2R,4S,5S,6R)-5-(((2S,4S,5S,6R)-5-((4-(2-(1H-imidazol-5-yl)ethyl)-2-methyl-1,4-oxazepan-7-yl)oxy)-4-hydroxy-6-methyltetrahydro-2H-pyran-2-yl)oxy)-4-hydroxy-6-methyltetrahydro-2H-pyran-2-yl)oxy)-12,14-dihydroxy-10,13-dimethylhexadecahydro-1H-cyclopenta[a]phenanthren-17-yl)furan-2(5H)-one.

In some embodiments, the compound is any one of the structures presented below:

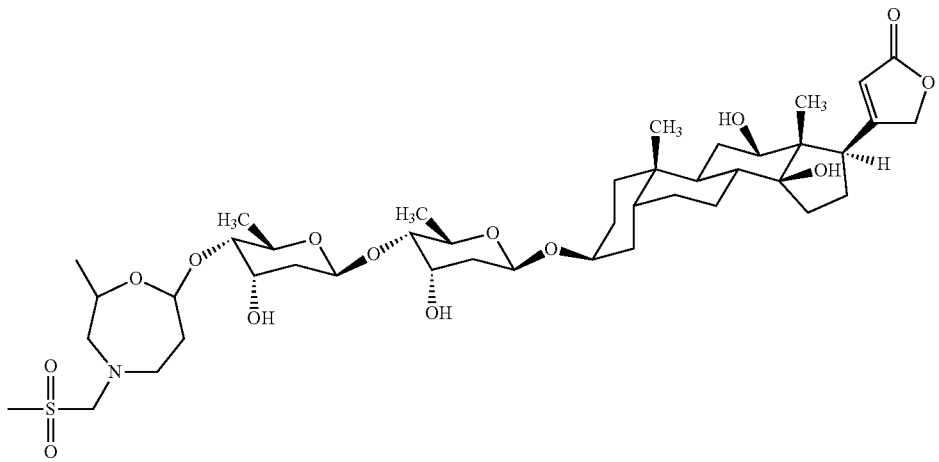

DMSM or 4-((3S,5R,8R,9S,10S,12R,13S,14S,17R)-12,14-dihydroxy-3-(((2S,4S,5R,6R)-4-hydroxy-5-(((2S,4S,5S,6R)-4-hydroxy-6-methyl-5-((2-methyl-4-((methylsulfonyl)methyl)-1,4-oxazepan-7-yl)oxy)tetrahydro-2H-pyran-2-yl)oxy)-6-methyltetrahydro-2H-pyran-2-yl)oxy)-10,13-dimethylhexadecahydro-1H-cyclopenta[a]phenanthren-17-yl)furan-2(5H)-one;

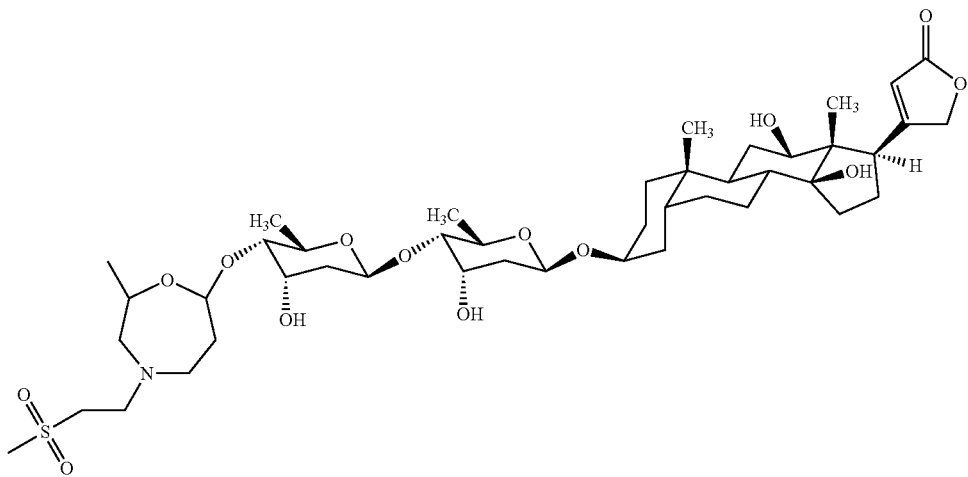

DESM or 4-((3S,5R,8R,9S,10S,12R,13S,14S,17R)-12,14-dihydroxy-3-(((2S,4S,5R,6R)-4-hydroxy-5-(((2S,4S,5S,6R)-4-hydroxy-6-methyl-5-((2-methyl-4-(2-(methylsulfonyl)ethyl)-1,4-oxazepan-7-yl)oxy)tetrahydro-2H-pyran-2-yl)oxy)-6-methyltetrahydro-2H-pyran-2-yl)oxy)-10,13-dimethylhexadecahydro-1H-cyclopenta[a]phenanthren-17-yl)furan-2(5H)-one; and

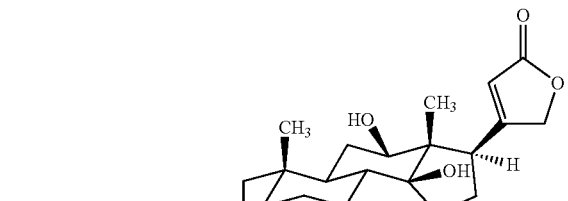

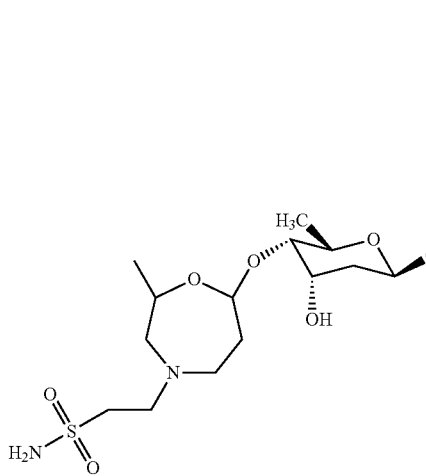

DESA or 2-(7-(((2R,3S,4S,6S)-6-(((2R,3R,4S,6S)-6-(((3S,5R,8R,9S,10S,12R,13S,14S,17R)-12,14-dihydroxy-10,13-dimethyl-17-(5-oxo-2,5-dihydrofuran-3-yl)hexadeca-hydro-1H-cyclopenta[a]phenanthren-3-yl)oxy)-4-hydroxy-2-methyltetrahydro-2H-pyran-3-yl)oxy)-4-hydroxy-2-methyltetrahydro-2H-pyran-3-yl)oxy)-2-methyl-1,4-oxazepan-4-yl)ethanesulfonamide.

In some embodiments, the compound is any one of the structures presented below:

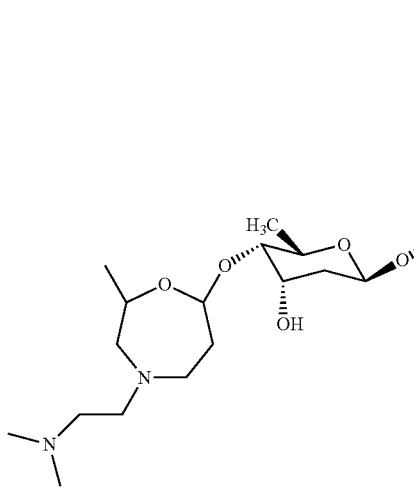

DEDA or 4-((3S,5R,8R,9S,10S,12R13S,14S,17R)-3-(((2R,4S,5S,6K)-5-(((2S,4S,5S,6R)-5-((4-(2-(dimethyl-amino)ethyl)-2-methyl-1,4-oxazepan-7-yl)oxy)-4-hydroxy-6-methyltetrahydro-2H-pyran-2-yl)oxy)-4-hydroxy-6-methyitetrahydro-2H-pyran-2-yl)oxy)-12,14-dihydroxy-10,13-dimethylhexadecahydro-1H-cyclopenta[a]phenanthren-17-yl)furan-2(5H)-one.

The present embodiments further encompass any enantiorners, diastereorners, optical isomers, prodrugs, solvates, hydrates, polymorphs, geometrical isomers and/or pharmaceutically acceptable salts of the compounds described herein.

Any one or more of the compounds presented herein may be present as a salt. The term "salt" encompasses both basic and acid addition salts, and include salts formed with organic and inorganic anions and cations. The term "organic or inorganic cation" refers to counter-ions for an acid. The counter-ions can be chosen from the alkali and to alkaline earth metals, (such as lithium, sodium, potassium, barium, aluminum and calcium), ammonium and the like. Furthermore, the term includes salts that form by standard acid-base reactions of basic groups and organic or inorganic acids. Such acids include hydrochloric, hydrofluoric, hydrobromic, trifluoroacetic, sulfuric, phosphoric, acetic, succinic, citric, lactic, maleic, fumaric, cholic, pamoic, mucic, D-camphoric, phthalic, tartaric, salicylic, methanesulfonic, benzenesulfonic, p-toluenesulfonic, sorbic, picric, benzoic, cinnamic, and like acids.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., amine and/or guanidine) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one to molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

All stereoisomers, optical and geometrical isomers of the compounds of the present invention are contemplated, either in admixture or in pure or substantially pure form. The compounds of the present invention can have asymmetric centers at one or more of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR spectra, melting point, and the like.

According to some aspects of some embodiments of the present invention, the compound is represented by general Formula III:

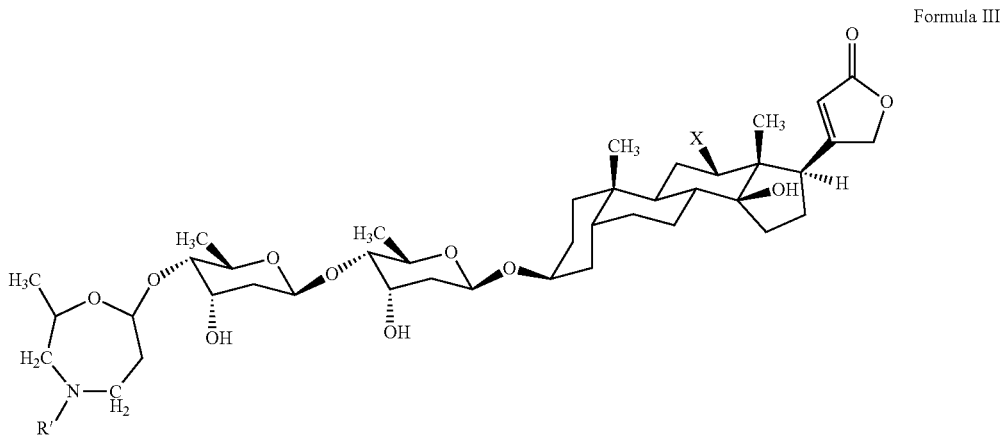

wherein:

X is H or OH;

R' is selected from the group consisting of OH, $C_1$-$C_6$ alkyl, $C_1$-$C_6$ haloalkyl ($C_1$-$C_6$ alkyl substituted with at least one halo), —$(CR^bR^c)nSi(R^a)_3$, —$(CR^bR^c)n$-C(=Y)—$NR_1R_2$, —$(CR^bR^c)n$-C(=Y)—NHOH, —$(CR^dR^c)n$-C(=Y)—$COOR_3$, —NHC(=Y)$NR_1R_2$ and —$(CR^bR^c)n$-$NH_2$;

Y is O or S;

$R_1$, $R_2$ and $R_3$ are each independently H or a $C_1$-$C_4$ alkyl;

Ra is a $C_1$-$C_4$ alkyl;

$R^b$, $R^c$, $R^d$ and $R^e$ are each independently selected from H, a $C_1$-$C_4$ alkyl and a $C_1$-$C_4$ hydroxyalkyl; and n is 0, 1 or 2;

or

R' is represented by general Formula

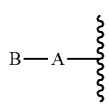

Formula II the wiggled line represents the N-link to the compound;

A is a spacer moiety or a covalent bond; and

B is a cyclic moiety;

or

R' is represented by general Formula

Formula II the wiggled line represents the N-link to the compound;

A is a spacer moiety or a covalent bond; and

B is selected from the group consisting of an alkylsulfonyl, art arylsulfonyl and a sulfonamide;

or

R' is represented by general Formula II:

Formula II the wiggled line represents the N-link to the compound;

A is a spacer moiety or a covalent bond; and

B is —$NR_1R_2$), wherein $R_1$ and $R_2$ are each independently H or a $C_1$-$C_4$ alkyl provided that at least one of $R_1$ and $R_2$ is a $C_1$-$C_4$ alkyl, including any pharmaceutically acceptable salt, prodrug, hydrate, solvate, enantiomer and diastereomer thereof, and any mixtures thereof, and a pharmaceutically acceptable carrier.

Additional alternative structures of R' are described in WO2015/029035, which is hereby specifically incorporated by reference as if fully set forth herein, thereby describing each and all such additional alternative structures.

Process of Preparing the Compounds:

According to an aspect of some embodiments of the present invention, there is provided a process for preparing the compounds represented by general Formula I, the process includes:

converting the third digitoxose moiety of digoxin or digitoxin into a dialdehyde; and reacting said dialdehyde with a reagent represented by general formula, IV:

B-A-$NH_2$     Formula IV

A is a spacer moiety or a covalent bond as described hereinabove; and

B is selected form the group consisting of a cyclic moiety, an alkylsulfonyl, arylsulfonyl, a sulfonamide, a secondary amine and a tertiary amine, as described hereinabove.

Scheme 1

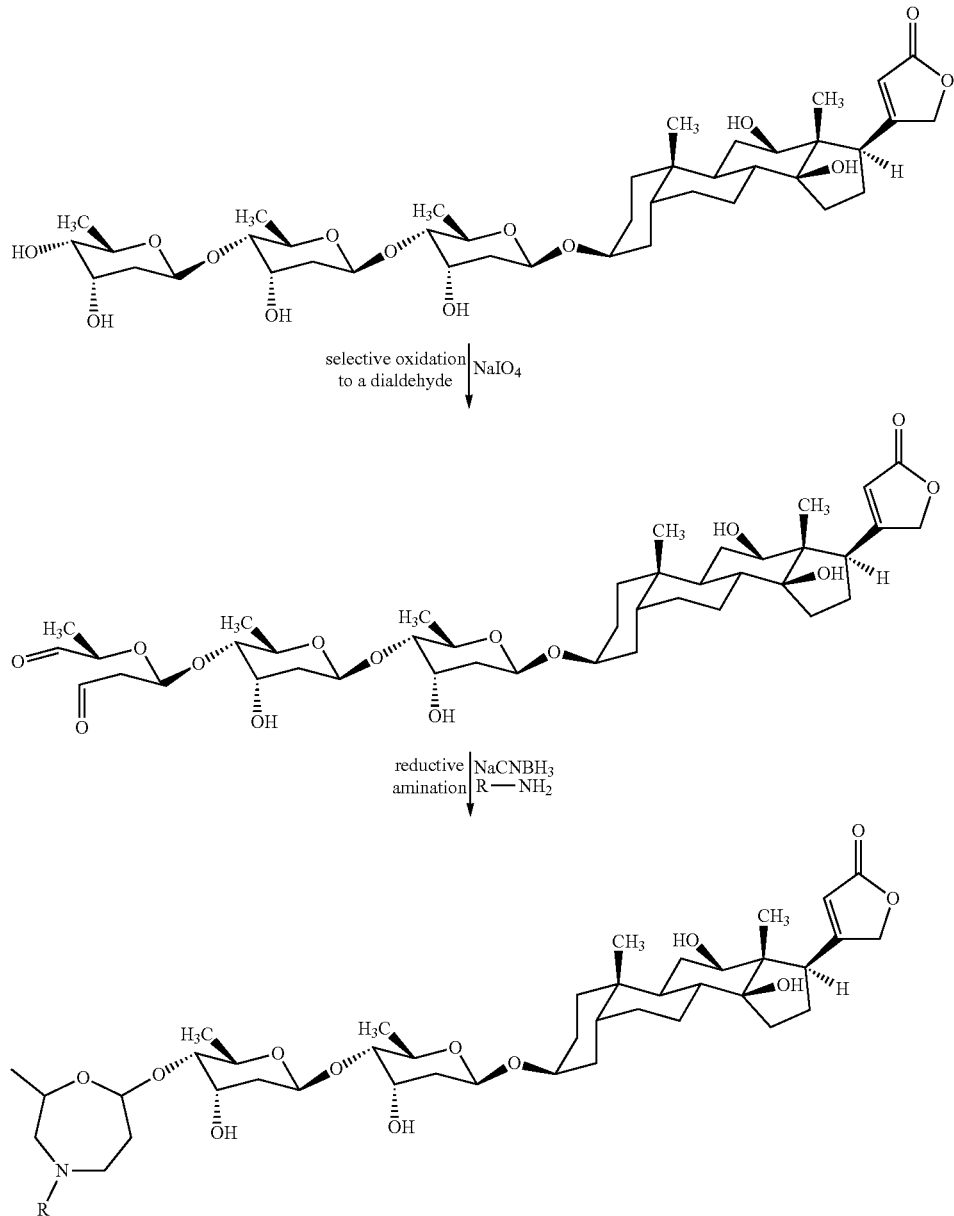

As can be seen in Scheme 1, the conversion of the third digitoxose moiety of digoxin or digitoxin is typically effected by selective oxidation thereof into a dialdehyde by reacting digoxin or digitoxin with a reagent that breaks apart 1,2-diols (vicinal dials) to afford aldehydes and/or ketones, such as sodium periodate (NaIO$_4$);

The reaction of the dialdehyde is effected by reductive amination of the dialdehyde using a free amine of R (R—NH$_2$) in the presence of, e.g., NaCNBH$_3$.

Selective Affinity and Inhibition:

The results presents in the Examples section below (see, e.g., Table 2) show clearly that compounds encompassed by general Formula I, according to embodiments of the present invention, exhibit high selectivity for α2β3 over α1β1 compared to digoxin and digitoxin. The results obtained for cyclic R-substituents (R comprising a cyclic moiety), some with 4 carbon atoms, provide a clear indication for selective structural interactions of the modified sugar of digoxin with the β3 subunit. This effect may also be combined with an enhanced interaction with the α2 subunit. The detailed enzymological study, presented hereinbelow, has been obtained with the purified detergent-soluble human Na,K-ATPase isolated isoform complexes, as well as with 1.5 intact bovine ciliary NPE cells, i.e., selective inhibition of human Na,KATPase isolated isoform complexes provided corroborating indication of inhibition by the compounds provided herein also of isoform mixture (α1β1 plus α2β3) as these are expressed in native NPE cell membranes.

According to some embodiments, the compounds presented herein, such as a compound represented by general Formula I or by general Formula III, exhibit an affinity to at least one isoform of Na,K-ATPase.

In the context of embodiments of the present invention, isoforms of Na,K-ATPase include any combination of α1, α2, α3 and α4 complexed with β1, β2 and β3; hence, isoforms of Na,K-ATPase include α1β1, α1β2, α1β3, α2α1, α2β2, α2β3, α3β1, α3β2, α3β3, α4β1, α4β2 and α4β3.

According to some embodiments of the present invention, a compound represented by general Formula I or by general Formula III, has a higher affinity to isoforms containing an α2 subunit, compared to its affinity to isoforms containing of the a subunits, such as α1, as demonstrated in the Examples section that follows below. The phrase "higher affinity to", as used herein, is a relative term that means that a given ligand molecule (compound, inhibitor, drug, etc.) is attracted and can bind to and (form a) complex with a target entity (protein, enzyme, drug-target) more strongly compared to its binding to another target entity. Affinity can be measured directly and indirectly by a number of methodologies. In some embodiments of the present invention, the affinity is referred to in terms of Ki (inhibition constant) or $K_D$ (dissociation constant), as these terms are known in the art. For example, a small value for Ki means that an inhibitor has a higher effective affinity to the enzyme relative to an affinity of the same inhibitor to another enzyme or another inhibitor to the same enzyme.

According to some embodiments of the present invention, a compound represented by general Formula I or by general Formula III, is a selective inhibitor of α2-containing isoforms of Na,K-ATPase, compared to α1-containing isoforms of Na,K-ATPase, as demonstrated in the Examples section that follows below.

The terms "selective inhibitor of α2-containing isoforms of Na,K-ATPase" or "selective inhibitor of the α2 isoform of Na,K-ATPase" or "α2-selective inhibitor", as used herein interchangeably, refer to a compound that inhibits α2-containing isoforms of Na,K-ATPase to a greater degree than the compound inhibits other isoforms of Na,K-ATPase, such as those containing α1. In some embodiments, the compounds described herein are selective for the α2β1, α2β2 and/or α2β3 isoforms of Na,K-ATPase over the α1β1 isoform thereof. In some embodiments, the selectivity of the compound for the α2-containing isoform of Na,K-ATPase (e.g., α2β1, α2β2 and/or α2β3 isoform) is at least about 4-fold (300% more selective) over other isoforms, or at least 5-fold (400%), at least 6-fold (500%), at least 8-fold (700%), at least 10-fold, at least 16-fold, at least 20-fold, at least 30-fold, or at least 50-fold greater inhibition of the α2-containing isoform of Na,K-ATPase over other isoforms of Na,K-ATPase.

Uses of α2-Selective Inhibitors:

The experimental work presented in the Examples section below demonstrates a clear correlation between increased α2β3-selectivity of the compounds presented herein and potency and duration in reducing IOP of either pharmacologically raised or basal (normal) IOP. Thus the results support a central role of α2β3 in production of aqueous humour. The mechanism of the IOP reduction has been shown to involve inhibition of active Na and K fluxes via NPE cells and reduction of inflow of aqueous humour after topical administration of compound(s) and permeation thereof via the cornea.

Without being bound by any particular theory, it is assumed that the low Ki values for inhibition of α2β3 (Ki of about 4 nM) and hydrophobic properties of the compounds according to some embodiments of the present invention, suggest that both traits contribute to the potency and long duration of action exhibited by the compounds provided herein. The finding that the compounds provided herein are effective in reducing basal (normal) IOP as low as 25-30% (see, e.g., FIGS. 2A-D and FIGS. 3A-C), as well as the reduction of acute 4AP-induced raised IOP (see, e.g., FIGS. 1A-D), provides an insight into the mechanism of action of the compounds.

The compounds presented herein are useful as topical opthalmological agents for treatment of glaucoma, since they exhibit at least one of efficacy and low levels of side-effects. In relations to alternative drugs, the compounds presented herein are useful as topical opthalmological agents for treatment of glaucoma, since they have been shown to exhibit at least one of improved efficacy, extended duration of desired effects and reduced side-effects, compared to currently available drugs, exemplified in the Examples section that follows below by the first-line drug latanoprost, and iopidine, used in short-term adjunctive therapy of chronic glaucoma. In general, currently available drugs include β-adrenergic antagonists and carbonic anhydrase inhibitors, that reduce the rate of aqueous humor production, or prostaglandin analogs, cholinergic agonists and sympathomimetics, that increase the rate of outflow through the trabecular meshwork and uveoscleral pathway. In this respect, the experimental results presented hereinbelow, show 25-30% higher reduction in basal IOP effected by the compounds presented herein in the rabbits, compared to Latanoprost, the current first-line drug for treatment of glaucoma.

In principle, the ability of the compounds presented herein, according to some embodiments, to reduce the basal IOP, could be relevant not only to optical hypertension and primary open angle glaucoma but also to normotensive glaucoma for which reduction of IOP below the basal level is required.

Regarding local toxicity, the rationale for making α2β3-selective inhibitors included not only the expectation of high potency but also of minimal local side-effects. In the Examples section below it is shown that corneal swelling, used to assess such adverse effect, is not observed at least over several days of topical administration of the compounds presented herein (see, e.g., Table 4). Similar evidence for safety was observed by inspection of local redness and irritation.

Concerning possible systemic toxicity of the α2β33-selective compounds presented herein, it is expected that cardiotoxicity, such as is associated with clinical use of digoxin, would be minimal, because the α2-selective compounds are likely to be intrinsically non-cardiotoxic, compared to a non-selective cardiac glycoside, and also because the pharmacokinetic concentration is likely to be low (see, e.g., inhibition results in Table 2).

The results presented hereinbelow indicate that after repeated administration to over several weeks of the compounds according to embodiments of the present invention, no signed of adverse effects have been observed, indicating that compounds represented by general Formula, I or III are not toxic and exhibit essentially no adverse effects.

Thus, the α2-selective inhibitors presented herein (compounds represented by general Formula I or by general Formula III) can be used to reduce intraocular pressure in a subject in need thereof, while taking advantage of the selective affinity these inhibitors exhibit towards α2-containing isoforms of Na,K-ATPase, which minimize adverse effects associated with unselective inhibition of the other isoforms.

According to an aspect of some embodiments of the present invention, there is provided a pharmaceutical composition which includes as an active ingredient any one of the compounds represented by general Formula I and a pharmaceutically acceptable carrier.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically to acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected topically, extraocularly, intraocularly and/or intravitreally. In some embodiments, the pharmaceutical composition is formulated as an ophthalmic composition suitable for topical, extraocular, intraocular and/or intravitreal administration to the eye of the subject. According to some embodiments, the pharmaceutical composition of the invention is an ophthalmic composition which is administered topically onto the eye of a subject for facilitating effective intraocular levels of the compound and for preventing unnecessary and unintentional levels of the compound in other tissues and/or organs. Such a non-systemic, site-specific administration reduces the side effects associated with the compounds.

In the context of some embodiments of the present invention, topical and/or extraocular administration is effected by applying the compound(s), or compositions and medicaments comprising the compound(s) to the eye or a bodily surface near the eye. According to some embodiments, the composition may take the form of an eye-drop solution, a spray, an eye wash solution, an ointment, a lotion, a suspension, a gel or a cream. The topical pharmaceutical compositions may be in the form of eye-drops to be applied by instillation into the eye or may be in the form of a viscous ointment, gel or cream to be applied by an ointment onto the ocular surface and may contain control release means for facilitating sustained release over a prolonged period of time.

In the context of some embodiments of the present invention, intraocular and/or intravitreal administration is effected by injecting the compound(s), or compositions and medicaments comprising the compound(s) into the eye or into a bodily tissue near the eye. According to some embodiments, the composition may take the form of an injectable solution.

According to some embodiments, oral or otherwise systemic administration in a dosage effective for reducing the intraocular pressure is also possible. For example, the composition may be administered by a dermal patch for extended release.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglicoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds presented herein to allow for the preparation of highly concentrated solutions.

Alternatively, the compounds presented herein may be in powder form for to constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

In accordance with other embodiments, the compounds presented herein may be loaded into a drug-delivery device to be inserted or implanted into the eye of the subject for allowing releasing of the compound in a controlled and continuous rate, by dissolving, diffusion or leaching, thus maintaining effective therapeutic concentration over a prolonged period of time. The drug-delivery device may be for example a biocompatible thin film loaded with the active agent, inserted for example beneath the lower eyelid. In some embodiments, the drug-delivery device is a contact lens or any other ophthalmic device, as these are known in the art.

In some embodiments, the pharmaceutical composition is packaged in a packaging material and identified in print, or on the packaging material, for use in reducing intraocular pressure (IOP).

According to an aspect of some embodiments of the present invention, there is provided a use of the compounds represented by general Formula I, or a pharmaceutical composition comprising the same, for the manufacture of a medicament for reducing intraocular pressure (IOP).

According to an aspect of some embodiments of the present invention, there is provided a method of reducing intraocular pressure (IOP) in a subject, the method includes administering to a subject in need thereof a therapeutically effective amount of a compound represented by general Formula I, or a pharmaceutical composition comprising the same.

According to some embodiments of the present invention, intraocular pressure (IOP) is associated with glaucoma, low-tension glaucoma and normal-tension glaucoma. Hence, the compounds, compositions and medicaments presented herein are useful in treating, without limitation, glaucoma, low-tension glaucoma and normal-tension glaucoma.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

In some embodiments, the concentration of the compounds presented herein in the pharmaceutical compositions or medicaments presented herein, is in the range of about 1 to about 5,000 μg/ml of composition, preferably from about 80 to about 800 μg/ml and the formulation is preferably applied in one to four doses per day wherein each dose contains about 1 to 125 μg of the compound, or from about 2 to about 20 μg of the compound.

Co-Administration with Other IOP Reducing Agents:

In the experimental section presented below, it has been demonstrated that a combination of a compound according to some embodiments of the present invention and Latanoprost resulted in a notable increase in the duration of the effects for the combination compared to the individually administered agents.

In the context of some embodiments of the present invention, an active agent which is not a compound represented by general Formula I or general Formula III, is referred to herein as "another agent" or "other agent".

According to an aspect of some embodiments of the present invention, there is provided a pharmaceutical composition which includes as active ingredients at least one other agent (active ingredient) which is in use in reducing IOP and is not a compound represented by general Formula I or general Formula III, a compound represented by general Formula I or general Formula III, and a pharmaceutically acceptable carrier.

Non-limiting examples of active ingredients which are in use in reducing IOP and which are referred to herein other agents, include prostaglandin analogs, β-blockers, adrenergic agents, α2-adrenergic receptor agonists, miotic agents, carbonic anhydrase inhibitors and cholinergic agonists.

Non-limiting examples of prostaglandin analogs include Latanoprost (Xalatan), Bimatoprost (Lumigan) and Travoprost (Travatan).

Non-limiting examples of n-blockers include Timolol (Timoptic) and Betaxolol (Betoptic).

A non-limiting example of adrenergic agents is Brimonidine (Alphagan).

A non-limiting example of miotic agents is Pilocarpine (Isoptocarpine, Pilocar).

Non-limiting examples of carbonic anhydrase inhibitors include Dorzolamide (Trusopt), Brinzolamide (Azopt) and Acetazolamide (Diamox).

Non-limiting examples of cholinergic agonists include carbachol (Miostat), echothiophate (Phospholine) and pilocarpine (Isopto Carpine, Pilopine).

Administration of more than one active agent to a subject is generally known in the art as co-administration. The term "co-administration" as used herein, refers to a concomitant administration of more than one active agent (active ingredient) to a subject, whereas in the context of embodiments presented herein, the term "concomitant" means that the co-administered active agents are present in the subject (PK), or otherwise exert an effect (PD), at similar, identical, consecutive or partially overlapping periods of time.

In the context of co-administration of more than one active agent, the terms "substantially simultaneous" and "rapid succession" correspond to the term "concomitant" as used herein, namely meaning that the period of time between a first administration and a second administration of more than one active agent is sufficiently short to be regarded as a single administration event, and/or a number of administrations of different active agents takes place within 5-60 minutes or less. Optionally, each administration in such "rapid succession" delivers to the user a different amount or composition of one or more pharmaceutically active agents. Alternatively, two or more of the administrations provide the same composition and amount of the one or more pharmaceutically active agents. In some embodiments, the later administration of the second active agent is performed at such timing that the first active agent of a previous administration within the same rapid succession does not yet have a significant pharmacodynamic effect or before it can be measured (pharmacokinetically) by, e.g., blood concentration thereof the first active agent.

According to some embodiments of the present invention, the co-administration of at least one other agent which is in use in reducing IOP and is not a compound represented by general Formula I or general Formula III, and a compound represented by general Formula I or general Formula III, exhibits a potentiating effect, namely that the effect of the co-administered active ingredients is greater in at least one parameter, such as magnitude or duration, compared to the effects exhibited by each of the active ingredients when administered alone (separately).

Accordingly, there is provided a use of at least one other agent which is in use in reducing IOP, and a compound represented by general Formula I or general Formula III, for the manufacture of a medicament for reducing IOP.

According to an aspect of some embodiments of the present invention, there is provided a method of reducing IOP in a subject in need thereof, the method includes co-administering to the subject a therapeutically effective amount of at least one other agent which is in use in reducing IOP, and a therapeutically effective amount of a compound represented by general Formula I or general Formula III.

According to an aspect of some embodiments of the present invention, there is provided a method of reducing IOP in a subject in need thereof, the method includes co-administering to the subject a synergistically effective amount of at least one other agent which is in use in reducing IOP, and a synergistically effective amount of a compound represented by general Formula I or general Formula III. It is noted herein that a synergistically effective amount is also a therapeutically effective amount in the sense of providing the desired therapeutic effect, and is smaller than the therapeutically effective amount of a singly-administered active ingredient.

In the context of the herein provided uses and method of co-administration of other agents and the compounds presented herein, the other agent is a prostaglandin analog.

In the context of the herein provided uses and method of co-administration of other agents and the compounds presented herein, the other agent is a β-blocker.

In the context of the herein provided uses and method of co-administration of other agents and the compounds presented herein, the other agent is an adrenergic agent.

In the context of the herein provided uses and method of co-administration of other agents and the compounds presented herein, the other agent is an α2-adrenergic receptor agonist.

In the context of the herein provided uses and method of co-administration of other agents and the compounds presented herein, the other agent is a miotic agent.

In the context of the herein provided uses and method of co-administration of other agents and the compounds presented herein, the other agent is a carbonic anhydrase inhibitor.

In the context of the herein provided uses and method of co-administration of other agents and the compounds presented herein, the other agent is a cholinergic agonist.

Cardiotonic Agent:

According to some embodiments, the selectivity of the compounds presented herein can be utilized in the treatment of other medical conditions. For example, an α2-selective inhibitor, such as the compounds presented herein and represented by general Formula I, can be used as an effective cardiotonic agent, with reduced cardiotoxicity, compared to known agents such as digoxin.

According to an aspect of embodiments of the present invention, there is provided a method of treating a heart condition which is carried out by administering to a subject in need thereof a therapeutically effective amount of a compound represented by general Formula I.

According to an aspect of embodiments of the present invention, there is provided a pharmaceutical composition which includes as an active ingredient a compound represented by general Formula I and a pharmaceutically acceptable carrier, identified in print, or on a packaging material, for use in a treatment of a heart condition.

According to an aspect of embodiments of the present invention, there is provided a uses of a compound represented by general Formula I or a pharmaceutical composition comprising the same, for the manufacture of a medicament for treating a heart condition.

Examples of heart conditions which are relevant in the context of embodiments of the resent invention, include, without limitation, atrial fibrillation, atrial flutter, mitral stenosis, chronic heart failure and congestive heart failure.

In some embodiments, the present invention provides cardiotonic compositions comprising a therapeutically effective amount of the compounds represented by general Formula I, or a pharmaceutical composition comprising the same. In accordance with such embodiments, the compounds may be formulated for oral, buccal, topical, intravenous, parenteral or rectal administration.

A compound represented by general Formula I or a compound represented by general Formula III can be used according to embodiments the present invention to treat a heart condition in combination with one or more other drugs for treating a heart a condition, such as, but not limited to, selective and nonselective β-blocker agents, anticoagulation agents, angiotensin-converting-enzyme inhibitors (ACE inhibitors) and angiotensin II receptor antagonists.

According to an aspect of embodiments of the present invention, there is provided a method of treating a heart condition in a subject in need thereof, which includes co-administering to the subject a therapeutically effective amount of an agent selected from the group consisting of a β-blocker, an anticoagulation agent, an angiotensin-converting-enzyme inhibitor and an angiotensin II receptor antagonist; and a compound represented by Formula III, as these are described herein, and a pharmaceutically acceptable carrier.

According to an aspect of embodiments of the present invention, there is provided a pharmaceutical composition that includes, as active ingredients, at least one ingredient selected from the group consisting of a β-blocker, an anticoagulation agent, an angiotensin-converting-enzyme inhibitor and an angiotensin II receptor antagonist; and a compound represented by Formula III, as these are described herein.

According to an aspect of embodiments of the present invention, there is provided a use of an agent selected from the group consisting of a β-blocker, an anticoagulation agent, an angiotensin-converting-enzyme inhibitor and an angiotensin II receptor antagonist, and a compound represented by Formula III, as these are described herein, for the manufacture of a medicament for treating a heart condition.

Nonselective β-blocker agents include propranolol, bucindolol, carteolol, carvedilol, labetalol nadolol, oxprenolol, penbutolol, pindolol, sotalol, timolol, eucommia bark (herb); β1-selective agents include acebutolol, atenolol, betaxolol, bisoprolol, celiprolol, esmolol, metoprolol, nebivolol; β2-selective agents include butaxamine and ICI-118, 551; and β3-selective agents include SR 59230A.

Anticoagulation agents include heparin, dicumarol, coumadin (warfarin) and aspirin.

ACE inhibitors include captopril, zofenopril, enalapril (vasotec, renitec), ramipril (altace, prilace, ramace, ramiwin, triatec, tritace), quinapril (accupril), perindopril (coversyl, aceon, perindo), lisinopril (listril, lopril, novatec, prinivil, zestril), benazepril (lotensin), imidapril (tanatril), trandolapril (mavik, odrik, gopten), cilazapril (inhibace) and fosinopril (fositen, monopril).

Angiotensin II receptor antagonists include losartan, EXP 3174, candesartan, valsartan, irbesartan, telmisartan, eprosartan, olmesartan, azilsartan and fimasartan.

According to some embodiments, the compound represented by general Formula I or the compound represented by general Formula III, according to embodiments of the present invention, and any one of the other drugs for treating a heart a condition can be co-formulated in a single composition, or be formulated into individual compositions.

High-Risk Pharmacokinetics:

When plasma concentrations of active drug depend exclusively on a single metabolic pathway, any condition that inhibits that pathway (be it disease-related, genetic, or due to a drug interaction) can lead to dramatic changes in drug concentrations and marked variability in drug action. This problem of high-risk pharmacokinetics is especially pronounced in drug elimination that relies on a single pathway. In this case, inhibition of the elimination pathway leads to striking elevation of drug concentration. For drugs with a narrow therapeutic window, this leads to an increased likelihood of dose-related toxicity. An example is digoxin, whose elimination is dependent on P-glycoprotein; many drugs inhibit P-glycoprotein activity (amiodarone, quinidine, erythromycin, cyclosporine, itraconazole) and coadministration of these with digoxin reduces digoxin clearance, and increases toxicity unless maintenance doses are lowered. Drugs with a high risk of generating pharmacokinetic interactions with digoxin include antacids and bile acid sequestrants, which can cause reduced absorption; inhibitors of CYPs and of P-glycoprotein such as amiodarone, quinidine, amiodarone, verapamil, cyclosporine, itraconazole and erythromycin which can cause decreased clearance.

Since compounds encompassed under Formula III are in essence digoxin derivatives that exhibit lower digoxin toxicity, these compounds can be used with any of the drugs described above which exhibit adverse drug-drug interaction with digoxin.

According to an aspect of embodiments of the present invention, there is to provided use of the compounds represented by general Formula III for the treatment of a medical condition or a combination of medical conditions, with is treatable by digoxin and a drug having an adverse interaction with digoxin.

Prodrugs:

Prodrugs corresponding to the compounds presented herein are contemplated in the context of the resent invention in order to provide active agents that exhibit improved pharmacokinetic and/or pharmacodynamics profile, and/or a reduction in adverse effects. As known in the art, a prodrug is typically a chemical derivative of the corresponding drug, being chemically modified such that a naturally occurring metabolic pathway in the subject's system can convert it to the parent drug molecule during the time in which the prodrug/drug is still present in the system. For instance, drugs that exhibit poor absorption due to high hydrophobicity, can be modified to exhibit improved bioavailability by introducing chemical functionalities that increase the solubility of the prodrug compareted to the parent active compound. In other cases where the active compound exhibits adverse effects in the GI-tract, the prodrug is a modified parent active compound that is metabolized by enzymes back to the parent compound substantially at the target tissues, organs or cells.

In the context of some embodiments of the present invention, the prodrugs are metabolized to afford the corresponding (parent) compound by naturally occurring metabolic agents, such as enzymes. In some embodiments, the chemical group of the prodrug is bioliable or biodegradable, such as in the case of an ester, which can be hydrolyzed by esterases to afford a hydroxyl of the parent compound.

According to some embodiments, the compounds presented herein exhibit several structural positions that can offer potential locations for chemical modifications on route to becoming suitable prodrugs. For example, a digoxin skeleton exhibits four hydroxyl groups which can potentially be converted into, e.g., esters, under various conditions. Similarly, the digitoxin skeleton exhibits three hydroxyl moieties. Since each hydroxyl is located at a different chemical environment, is it chemically converted under varying conditions, thereby allowing the production of a single or a multiple hydroxyl-to-ester conversion. Thus, in the case of digoxin, a mono-, a bis-, a tris- or a tetra-modified parent compound can be afforded, offering a variety of prodrugs of the same patent compound, each exhibiting a different pharmacokinetic/pharmacodynamics profile.

In addition, R and R' substituents (see, Formula I and Formula III respectively) may exhibit a chemical position which is readily converted into another, bioliable (biodegradable) moiety, and thus can be used to afford prodrugs from the corresponding parent compound.

According to some embodiments, prodrugs of the compounds having the general Formula I or general Formula III, are represented by general Formula V:

Formula V wherein X is H or PD$_3$, and each of PD$_1$-PD$_4$ is H or independently represents a modified hydroxyl group turned into a bioliable functionality, provided that at least one of PD$_1$-PD$_4$ is not H.

In some embodiments, the compounds presented herein are converted into a prodrug by modifying any one of the hydroxyl groups on the digoxin or digitoxin moiety of the compounds into any one of a methoxymethyl ether, a tetrahydropyranyl ether, a t-butyl ether, an allyl ether, a benzyl ether, a t-butyldimethylsilyl ether, a t-butyldiphenylsilyl ether, an acetic acid ester (Ac), ethyl, propyl, butyl, t-butyl or pivalic acid ester and a benzoic acid ester, in any combination. Each of the converted hydroxyl functionalities may be metabolized (biodegraded) back to the parent hydroxyl by one or more metabolic and/or enzymatic systems.

According to some embodiments, any one of PD$_1$-PD$_4$ in general Formula V is selected from the group consisting of a methoxymethyl ether, a tetrahydropyranyl ether, a t-butyl ether, an allyl ether, a benzyl ether, a t-butyldimethylsilyl ether, a t-butyldiphenylsilyl ether, an acetic acid ester (Ac), ethyl, propyl, butyl, t-butyl or pivalic acid ester and a benzoic acid ester.

As can be seen in the Examples section that follows below, the exemplary digoxin-derived compound DcB according to some embodiments of the present invention, has been converted successfully into the corresponding bit-acetyl (BisAcDcB) prodrug and the tris-acetyl (TrisAcDcB) prodrug (see, Example 6).

Isolation and Use of Na,K-ATPase Isoforms:

According to an aspect of some embodiments of the present invention, there is provided a method of determining an apparent affinity of the compound represented by general Formula I to at least one isoform of Na,K-ATPase, the method includes contacting an isoform of Na,K-ATPase with the compound in an activity measurement setup and determining the apparent affinity of the compound to the isoform.

According to an aspect of some embodiments of the present invention, there is provided a method of isolating an isoform of Na,K-ATPase of a mammal, the method includes:
transforming yeast cells with a clone that comprises an a chain sequence and a β chain sequence of the Na,K-ATPase;
expressing the clone in the yeast cells; and
isolating the isoform,
wherein:
the α chain sequence is selected from the group consisting of α1, α2, α3 and α4; and
the β chain sequence is selected from the group consisting of β1, β2 and β3.

In some embodiments, the isolated isoform is α2β2.
In some embodiments, the isolated isoform is α2β3.

According to an aspect of some embodiments of the present invention, there is provided an isolated α2β2 isoform of Na,K-ATPase of a mammal having at least 70% purity.

According to an aspect of some embodiments of the present invention, there is provided an isolated α2β3 isoform of Na,K-ATPase of a mammal having at least 70% purity.

The yeast-expressed α/β subunits have distinct levels of glycosylation compared to those in the human-expressed subunits. The distinct yeast-expressed glycosylation pattern does not substantially affect the activity of the enzyme but may increase its stability.

According to an aspect of some embodiments of the present invention, there is provided an isolated α2β2 iso-form of Na,K-ATPase of a mammal having a yeast-characterizing glycosylation pattern.

According to an aspect of some embodiments of the present invention, there is provided an isolated α2β3 isoform of Na,K-ATPase of a mammal having a yeast-characterizing glycosylation pattern.

In some embodiments, the isolated isoforms presented herein have an amino acid sequence which identical, substantially similar or derived from any one of the isoform of human of Na,K-ATPase.

SEQ ID NOS.

Description SEQ ID No.
Amino acid sequence of α1 subunit of human Na,K-ATPase (P05023) 1
Amino acid sequence of α2 subunit of human Na,K-ATPase (P50993) 2
Amino acid sequence of α3 subunit of human Na,K-ATPase (P13637) 3
Amino acid sequence of α4 subunit of human Na,K-ATPase (Q13733) 4
Amino acid sequence of β1 subunit of human Na,K-ATPase (P05026) 5
Amino acid sequence of HIS tagged β1 subunit of human Na,K-ATPase (P05026) 6
Amino acid sequence of β2 subunit of human Na,K-ATPase (P14415) 7
Amino acid sequence of HIS tagged β1 subunit of human Na,K-ATPase (P14415) 8
Amino acid sequence of β3 subunit of human Na,K-ATPase (P54709) 9
Amino acid sequence of HIS tagged β3 subunit of human Na,K-ATPase (P54709) 10
Nucleotide sequence of α1 subunit of human NaX-ATPase (ATP1A1) 11
Nucleotide sequence of α2 subunit of human Na,K-ATPase (ATP1A2) 12
Nucleotide sequence of α3 subunit of human Na,K-ATPase (ATP1A3) 13
Nucleotide sequence of α4 subunit of human Na,K-ATPase (ATP1A4) 14
Nucleotide sequence of HIS tagged β1 subunit of human Na,K-ATPase (ATP1B1) 15
Nucleotide sequence of HIS tagged β2 subunit of human Na,K-ATPase (ATP1B2) 16
Nucleotide sequence of HIS tagged β3 subunit of human Na,K-ATPase (ATPIB3) 17
Nucleotide sequence of HIS tagged human FXYD1 18
Amino acid sequence of HIS tagged human FXYD1 19

As used herein the term "about" refers to 10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is expected that during the life of a patent maturing from this application many relevant inhibitors exhibiting selectivity towards α2-containing isoforms of Na,K-ATPase, as defined herein, will be uncovered and the scope of this term is intended to include all such new selective inhibitors a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Compound Synthesis

Compounds represented by general Formula I, according to embodiments of the present invention, were synthesized as a series of perhydro-1-4-oxazepine derivatives of the third digitoxose of digoxin or digitoxin following a general procedure described elsewhere [Adamczyk, M. et al., *Steroids*, 1995, 60(11), pp. 753-758] by selective oxidation with $NaIO_4$ and reductive amination with $NaCNBH_3$. The compounds were purified by HPLC and masses, $^1H$-NMR and $^{13}C$-NMR spectra were determined to verify both correctness of the structure and purity.

The structure and names based on of the amine substituents ($R-NH_2$), as well as their theoretical and measured masses, are presented in Table 1 below, which includes other digoxin derivatives with non-cyclic moieties (last eight compounds in Table 1).

TABLE 1

| R | Name | Theoretical mass | Measured mass (with Na+ ion) |
|---|---|---|---|
| cyclopropyl | DcP | 803.48 | 826.45 |
| methylcyclopropane | DMcP | 817.50 | 840.44 |
| ethylcyclopropane | DEcP | 831.51 | 854.58 |
| cyclobutyl | DcB | 817.50 | 840.43 |
| cyclopentyl | DcPe | 831.51 | 854.51 |
| cyclohexyl | DcHe | 845.53 | 868.65 |
| benzyl | DBz | 853.50 | 876.44 |
| methyl(3,3-dimethylcyclobutane) | DMDMcB | 859.54 | 882.59 |
| methylcyclopropane | DtxMcP | 801.50 | 824.48 |
| cyclobutyl | DtxcB | 801.50 | 824.44 |
| methyl | DMe | 777.47 | 800.57 |
| ethyl | DEt | 791.48 | 814.52 |
| 2,2,2-trifluoroethyl | $DCF_3$ | 845.45 | 868.14 |
| propyl | DP | 805.50 | 828.27 |
| iso-propyl | DiP | 805.50 | 828.41 |
| iso-butyl | DiB | 819.51 | 842.66 |
| tert-butyl | DtB | 819.51 | 842.41 |
| methyl(trimethylsilyl) | DTMS | 849.51 | 872.77 |
| (methylsulfonyl)methyl | DMSM | 855.44 | 878.49 |
| (methylsulfonyl)ethyl | DESM | 869.46 | 892.29 |
| (sulfonamide)ethyl | DESA | 870.45 | 893.47 |
| azetidinyl | DAz | 818.49 | 841.55 |
| oxetanyl | DOx | 819.48 | 842.41 |
| thietanyl | DTh | 835.45 | 858.37 |
| histaminyl | DHis | 857.50 | 880.45 |
| (N,N-dimethylamine)ethyl | DEDA | 834.52 | 857.62 |
| aminoethyl | DED | 806.49 | 829.55 |
| (methylsulfonyl)methyl | DMSM | 855.44 | 878.49 |

Names of compounds encompassed under Formula I wherein X=OH (digoxin derivatives) include Dcp, DMcP, DEcP, DcB, DcB, DcB, DcB and DMDMcB; names of compounds encompassed under Formula I wherein X=H (digitoxin derivatives include, DtxMcP and DtxcB.

Example 2

Expression, Purification and Characterization of Recombinant Human Na,K-ATPase Isolated Isoforms Plasmid construction for the expression of α1β1, α1β, α2β1, α2β2 and α2β3 Na,K-ATPase was conducted by generation of pHil-D2 expression vector containing cDNA of human $α_1$ and His10 tagged human $β_1$ was described previously [Lifshitz Y, et al., 2007, *Biochemistry*, 46(51), pp. 14937-14950]. cDNA of human $β_2$ and $β_3$ in pSD5 were a gift from K. Geering, University Lausanne, Switzerland. Open reading frames and flanking regions of human $β_2$ and human $β_3$ were amplified by PCR using primers containing BglII and SalI cleavage sites. The resulting fragments were subcloned into pHil-D2-hα$_2$/His10-pβ$_1$ to create pHil-D2-hα$_2$/His10-hβ$_2$ and pHil-D2-hα$_2$/His10-hβ$_3$, respectively. Correct integration and sequence was confirmed by sequencing.

Yeasts were grown in BMG (100 mM potassium phosphate pH 6, 1.34% yeast nitrogen base, 4×10$^{-5}$% biotin, 0.3% glycerol) to OD 6-8 and expression was induced in BMM (100 mM potassium phosphate pH 6, 1.34% yeast nitrogen base, 4×10$^{-5}$% biotin, 0.5% methanol added daily).

Pichia pastoris transformation, yeast growth, membrane preparation and His-tag purification of recombinant human α1β1, α2β1, αβ2 and α2β3 Na,K-ATPase were carried out essentially as described previously [Katz A, et al., 2010, J Biol Chem, 285(25), pp. 19582-19592; and Katz A, et al., 2014, J Biol Chem, 289(30), pp. 21153-21162].

Expression and purification of α1β1, α2β1, α2β2 and α2β3 complexes was conducted in small scale whole cell lysates that were prepared as describe in Loayza, D. et al., Mol. Cell. Biol., 1998, 18, p. 779-789. Yeast membrane production and expression of recombinant Na,K-ATPase as detergent soluble complexes was performed as described in Habeck, M. et al., J. Biol. Chem., 2015, 290, pp. 4829-4842, using modified lipid content (C12E8, 0.1 mg/ml; SOPS, 0.07 mg/ml; cholesterol, 0.01 mg/ml).

Na,K-ATPase $\alpha_1\beta_1$, $\alpha_2\beta_1$, $\alpha_2\beta_1$ and $\alpha_2\beta_3$ complexes were reconstituted with FXYD1 and purified in a mixture of 0.1 mg/mi. C12E8, 0.07 mg/ml SOPS and 0.01 mg/ml cholesterol.

The purified isoform complexes (0.3-0.5 mg/ml) were eluted from the BD-Talon beads in a solution containing Imidazole 170 mM, NaCl 100 mM; Tricine.HCl 20 mM pH 7.4; C12E8, 0.1 mg/ml; SOPS 0.07 mg/ml, cholesterol 0.01 mg/ml, glycerol 25%, by gravity-column. The proteins were stored at −80° C. Protein purity was determined by gel electrophoresis and protein concentration was determined with BCA (B9643 Sigma).

The specific Na,K-ATPase activity was highest for $\alpha_1\beta_1$ (16.4±0.7 μmol/mg/min) followed by $\alpha_2\beta_1$ (10.9±0.6) and $\alpha_2\beta_3$ (10.7±1.9). The $\alpha_2\beta_2$ isoform had the lowest activity (8.4±1.4). The second significantly different parameter is the apparent K$^+$-affinity. $K_{0.5}$ K$^+$ for $\alpha_2\beta_1$ was 2.7±0.14 mM compared to 1.47±0.06 mM for $\alpha_1\beta_1$. $\alpha_2\beta_2$ and $\alpha_2\beta_3$ had an even lower affinity than $\alpha_2\beta_1$ with apparent $K_{0.5}$ values of 7.4±0.19 mM and 6.4±0.50 mM, respectively. Na-titrations revealed that the affinity for Na$^+$-ions was not different between $\alpha_1\beta_1$ and $\alpha_2\beta_1$ whereas $\alpha_2\beta_2$ and $\alpha_2\beta_3$ had a somewhat higher Na-affinity.

The reduced apparent affinity for K$^+$ together with an increased affinity for Na$^+$ indicates that the conformational equilibrium of $\alpha_2\beta_2$ and $\alpha_2\beta_3$ might be shifted towards E1. In order to test this hypothesis, the apparent affinity of vanadate was determined for all four isoform complexes. Vanadate is a phosphate analogue that binds to the E2 conformation, mimicking the transition state E2PK$_2$ during dephosphorylation, thus inhibiting the enzyme. An three $\alpha_2$ isoforms had a lower vanadate affinity compared to $\alpha_1\beta_1$ (0.48 μM). $\alpha_2\beta_2$ had the lowest vanadate affinity (34 μM) followed by $\alpha_2\beta_3$ (1.9 μM) and $\alpha_2\beta_1$ (3.5 μM). Thus, the order of inhibition by vanadate equals the order of potassium activation ($K_{0.5}$K$^+$ and $K_i$ vanadate $\alpha_1\beta_1<\alpha_2\beta_1<\alpha_2\beta_3<\alpha_2\beta_3$) supporting the hypothesis proposed above.

Example 3

Selective Inhibition Assays of Isolated Na,K-ATPase

To screen for isoform selectivity of the digoxin derivatives we compared inhibition of Na,K-ATPase activity of purified detergent-soluble human isoform complexes α1β1FXYD1, α2β1FXYD1, α2β2FXTD1 and α2β3FXYD1. Although all the preparations and assays were conducted with FXYD1 in order to stabilize the complexes, the FXYD1 suffix is omitted in naming of isoform complexes for simplicity.

Na,K-ATPase activity of α/βPFXYD1 complexes was measured over one hour at 37° C. in a medium containing 130 mM NaCl, 5 mM KCl, 3 mM MgCl$_2$, 1 mM EGTA, 25 mM Histidine, pH 7.4 and 1 mM ATP using the PiColor Lock gold malachite green assay (Inova Biosciences).

The Na,K-ATPase activities were α1β1, 21.5±5.3 μmoles/min/mg; α2β1, 18.7±1.8 μmoles/min/mg, and α2β3, 10.7±1.9 μmoles/min/mg protein. As discussed below, an important kinetic property in relation to inhibition by cardiac glycosides is $K_{0.5}$ for activation by K: α1β1-1.25±0.05 mM, α2β1-2.7±0.14 mM and α2β3 6.4±0.50 mM, respectively.

Selectivity of the compounds for various isolated isoforms of human Na,K-ATPase was determined essentially as described before [Katz, A. et al., J Biol Chem., 2010, 285(25), pp. 19582-19592].

ATPase activity assays as well as titrations with NaCl, KCl and vanadate were performed as described in Lifshitz-2007 and Loayza-1998 using PiColorLock™ malachite green assay (Inova Bioscience). Inhibitor assays were performed as described in Katz-2010. [$^3$H]ouabain binding and K$^+$-[$^3$H]digoxin displacement assays were performed as described in Katz-2010.

The percent inhibition VCG/V0 was calculated and Ki values were obtained by fitting the data to the function VCG/V0=Ki/([CG]+Ki)+c (CG stands for cardiac glycoside). Inhibition was estimated in 3-5 separate experiments and average Ki values±standard error of the mean (SEM) were calculated. The ratios Ki α1β1/α2β1, α1β1/α2β2 and α1β1/α2β3 was calculated for each compound.

Table 2 shows the Ki values and selectivity ratios (Ki α1β1:α2β1, Ki α1β1:α2β2, and α1β1:α2β3) for inhibition of Na,K-ATPase activity of compounds according to embodiments of the present invention, as well as some digoxin derivatives having a non-cyclic moiety, compared to digoxin and digitoxin. Table 2 is arbitrarily sorted according to column "Ki ratio α1β1/α2β3" marked by "*".

TABLE 2

| Compound Name | No. of C atoms in R | Ki in nM ± SEM | | | | Selectivity | | |
| | | α1β1 | α2β1 | α2β2 | α2β3 | Ki ratio α1β1/α2β1 | Ki ratio α1β1/α2β2 | * Ki ratio α1β1/α2β3 |
| --- | --- | --- | --- | --- | --- | --- | --- | --- |
| DcB (cyclic) | 4 | 135 ± 11 | 8 ± 1.25 | 6 ± 1 | 4 ± 0.15 | 16.9 | 22.2 | 33.6 |
| DMcP (cyclic) | 4 | 95.8 ± 13.7 | 18.3 ± 1.6 | 8.0 ± 0.8 | 4.3 ± 0.6 | 5.2 | 12 | 22.2 |
| DESM (sulfonyl) | 2 | 464 ± 14 | 49.2 ± 1.9 | 31.7 ± 3.2 | 24.7 ± 2.1 | 9.4 | 14.6 | 18.8 |
| DiB | 4 | 92 ± 8.9 | 20.6 ± 1.4 | 10 ± 0.8 | 5.8 ± 0.6 | 4.4 | 9.0 | 16 |
| DESA (sulfonamide) | 2 | 301 ± 23 | 38.9 ± 2.2 | 31.5 ± 4.4 | 20.1 ± 0.9 | 7.7 | 9.5 | 15 |
| DiP | 3 | 149 ± 20.7 | 28.9 ± 1.7 | 16.7 ± 1.9 | 10.3 ± 1.8 | 5.1 | 8.9 | 14.4 |

TABLE 2-continued

| Compound Name | No. of C atoms in R | Ki in nM ± SEM | | | | Selectivity | | |
| --- | --- | --- | --- | --- | --- | --- | --- | --- |
| | | α1β1 | α2β1 | α2β2 | α2β3 | Ki ratio α1β1/α2β1 | Ki ratio α1β1/α2β2 | * Ki ratio α1β1/α2β3 |
| DcP (cyclic) | 3 | 109 ± 6.2 | 14.6 ± 11.6 | 13.0 ± 1.3 | 8.1 ± 1.36 | 7.5 | 8.5 | 13.4 |
| DEcP (cyclic) | 5 | 86.1 ± 7 | 14.3 ± 2 | 12.1 ± 1.9 | 7.2 ± 1 | 6.02 | 7.1 | 12.02 |
| DMSM (sulfonyl) | 3 | 944 ± 123 | 137 ± 9.8 | 123 ± 7.3 | 89 ± 8.7 | 6.9 | 7.7 | 10.6 |
| DBz (cyclic) | 6 | 57.9 ± 15.5 | 10.1 ± 2.2 | 6.8 ± 1.2 | 5.6 ± 1.6 | 5.7 | 8.5 | 10.3 |
| DcH (cyclic) | 6 | 70.4 ± 4.1 | 15.2 ± 3.7 | 15.3 ± 2.9 | 11.7 ± 4.5 | 4.6 | 4.6 | 10.1 |
| DCF$_3$ | 2 | 119 ± 15.0 | 28.6 ± 0.9 | 18.1 ± 1.9 | 12.4 ± 1.5 | 4.1 | 6.5 | 9.6 |
| DEt | 2 | 137.9 ± 12.6 | 23.2 ± 0.9 | 16.4 ± 1.6 | 14.4 ± 1.27 | 5.9 | 8.3 | 9.5 |
| DMe | 1 | 103 ± 5.6 | 15.3 ± 1.2 | 20.36 ± 1.8 | 10.8 ± 0.6 | 6.7 | 5.1 | 9.5 |
| DP | 3 | 87.7 ± 7.9 | 18.3 ± 1.68 | 10.5 ± 1.8 | 9.8 ± 1.1 | 4.8 | 8.3 | 8.8 |
| DtB | 4 | 135 ± 12.1 | 21.6 ± 5.6 | 18.4 ± 1.1 | 16.3 ± 0.28 | 6.2 | 7.3 | 8.2 |
| DMDMcB (cyclic) | 7 | 31.6 ± 0.5 | 8.6 ± 1.4 | 5.1 ± 0.5 | 3.9 ± 0.7 | 3.69 | 6.16 | 8.19 |
| DtxcB (cyclic) | 4 | 30.7 ± 7.2 | 5.4 ± 0.5 | 5.3 ± 0.8 | 4.3 ± 0.6 | 5.6 | 5.8 | 7.1 |
| DtxMcP (cyclic) | 4 | 25 ± 4 | 4.2 ± 0.4 | 5.4 ± 1.2 | 3.7 ± 0.5 | 5.9 | 4.6 | 6.7 |
| DTMS (silyl) | 4 | 72.6 ± 17.6 | 24.3 ± 4.0 | 14.3 ± 1.3 | 11.1 ± 1.6 | 3 | 5.1 | 6.5 |
| Digoxin | 0 | 268 ± 13.8 | 58.7 ± 5.4 | 58 ± 1.9 | 42.8 ± 3.0 | 4.5 | 4.6 | 6.2 |
| DcPe (cyclic) | 5 | 138 ± 21 | 33.4 ± 7.5 | 33.5 ± 11.9 | 27.6 ± 9.5 | 4.1 | 4.1 | 5 |
| Digitoxin | 0 | 89 ± 15.8 | 29.5 ± 2.7 | 40.7 ± 6.7 | 28.8 ± 5.9 | 3 | 2.1 | 3.1 |

As can be seen in Table 2, some compounds show an even greater selectivity ratio towards α2β2 and α2β3, particularly α2β3. Based on the ratios of Ki values, several derivatives show significantly improved selectivity for α2β3 compared to α2β1 over α1β1, in particular DMcP and DcB. DMcP and DcB show exceptional selectivity for α2β2 and α2β3 over α1β1 of 22-fold and 33-fold, respectively, and very low Ki values for inhibition of α2β3 (Ki about 4 nM). The full inhibition curves of DMcP and DcB emphasize the extent of the difference between α1β1 and α2β3.

Bearing in mind the large differences in $K_{0.5}$ potassium ions, a point to be aware of in analyzing the results presented in Table 2 is the well-known K-cardiac glycoside antagonism. Digoxin itself has moderate selectivity for α2β1 over α1β1 (about 4-fold) and the data in Table 2 shows increased selectivity for α2β3 over α1β1 (about 6-fold). The α2β1-selectivity of digoxin is attributed to a combination of increased binding affinity for α2 over α1 and also reduced K-digoxin antagonism in the Na,K-ATPase reaction conditions (with K, 5 mM). Similarly, the increased selectivity of digoxin for α2β3 compared to α2β1 is attributable to reduced K-cardiac glycoside antagonism due to the higher $K_{0.5}$ K of α2β3 compared to α2β1.

The compounds presented herein show a notable increase of the ratio of Ki's α1β1:α2β3 compared to α1β1:α2β1, which must be partly due to the reduced K-cardiac glycoside antagonism. However, the difference for the most α2β3-selective compounds is significantly greater than that for digoxin and cannot be explained only by this factor. In particular, there is a distinct structural effect in that the maximal α2β3-selectivity is seen for R-substituents with cyclic moiety, as well as those with four carbon atoms. In the case of DMcP and DcB, the Ki for α1β1 is about 2-3-fold lower than for digoxin itself but the Ki for α2β3 is about 10-fold lower than for digoxin, thus raising selectivity for α2β3 over α1β1 to more than 22-fold and more than 33-fold, respectively. It is also noticeable that for derivatives with five or a higher number of carbon atoms in the R-substituents, such as DEeP, DcPe, DcH, DBz and DDMcB, although the Ki values for all isoforms are all lower than for digoxin itself, the selectivity for α2β3 over α1β1, 10-12-fold, is also lower than the selectivity observed in four carbon R-substituents, DMcP and DcB. The same is true for compounds with R-substituent three carbons or shorter.

Another structural insight comes from the results obtained for two digitoxin derivatives (DtxMcP and DtxcB) compared with the digoxin derivatives DMcP and DcB. As seen in Table 2, the Ki values are relatively low for all three isoform complexes α1β1, α2β1 and α2β3, being reduced about 10-fold compared to digoxin. Consequently, these digitoxin derivatives showed little increase in selectivity for α2β3 compared to digoxin itself. Thus, the absence of a single OH group in position 12 of the steroid moiety of digitoxin reduced the effect of the sugar modification on α2β3-selectivity.

Thus, modification of the third digitoxose moiety of digoxin, but not of digitoxin, with cyclic substituents such as McP and cB confers notable α2β3-selectivity, presumably due to selective interaction with β3.

Example 4

Inhibition of Na,K-ATPase Activity Permeabilized Bovine NPE Cells

In order to prove the concept of selective inhibition of the compounds presented herein in Na,K-pumps of native ciliary epithelium, inhibition assays using Na,K-ATPase in NPE cells isolated from the ciliary body dissected out of bovine eyes were conducted.

Isolation of ciliary epithelium PE and NPE cells was carried out as previously described [Edelman, J L. et al., 1994, Am J. Physiol, 266(5 Pt 1), pp. C1210-1221], with some modifications, using 15-20 fresh bovine eyes. Ciliary bodies were isolated from bovine eyes and washed in ringer solution. The tissue was treated with trypsin and homogenized followed by separation on a density gradient of Metrizamide, which separates between the NPE and PE cells.

Using isolated human isoforms to calibrate the response of the antibodies, NPE cell lysates were shown to contain about 70% α2 and 30% α1, while PE were shown to contain about 90% α1 and 5-10% α2. After unmasking the Na,K-ATPase by treating the cells with alamethicin, Na,K-ATPase activity was measured and was found to be 0.195±0.027 and 0.035±0.008 nmoles/mg protein/min in NPE and PE cells, respectively. Ouabain-sensitive fractions of total ATPase activity were about 65% and 35% for NPE and PE cells, respectively.

To determine NaK-ATPase activity in the cells, the cells were incubated with 0.8 mg/ml alamecithin for 30 minutes at room temperature prior to transfer to the reaction medium containing 130 mM NaCl, 5 mM KCl, 3 mM $MgCl_2$, 25 mM histidine, pH 7.4, 1 mM EGTA, 1 nM sodium azide, 0.5 mM ATP, and were then incubated for 45 minutes at 37° C., with or without the tested inhibitors as indicated, or 0.5 mM ouabain to determine the ouabain insensitive ATPase activity. The data was fitted to one or two sites inhibition model.

Table 3 presents Ki values for inhibition of NPE Na,K-ATPase activity by digoxin, DMe, DMcP and DcB, fitted to a single site inhibition model.

TABLE 3

| Compound | Ki, nM ± SEM | n |
|---|---|---|
| *1 site model* | | |
| Digoxin | 91.7 ± 10.2 | 4 |
| DMe | 15.6 ± 1.3 | 4 |
| DMcP | 7.9 ± 2.2 | 5 |
| DcB | 17.3 ± 2.5 | 4 |
| *2 sites model* | | |
| DcB | Ki α2 6.9 ± 2  Ki α1 151 ± 7.6 (A α2 0.66 ± 0.090 A α1 0.34 ± 0.097) | 4 |

As can be seen in Table 3, the Ki values of the derivatives are all lower than that of digoxin. Since NPE cells contain about 70% α2 and 30% α1, Na,K-ATPase activity and inhibition should reflect the properties of the isoform mixture. Indeed, the detailed inhibition curve for the most α2β3-selective compound, DcB, was fitted better by a two site model, compared to fitting according to a one site model.

As can be seen in Table 3, the two site model provides the best fit parameters of 66% α2, Ki 6.9±2 nM; 34% α1, Ki 151±7.6 nM (Ki α1/α2=22), which are quite close to the proportions of α2β1 estimated in the immunoassays, and the selectivity ratio Ki α1β1/α2β3 is about 33.

Thus, it can be concluded that the selectivity properties of the digoxin derivative DcB observed with purified human isoforms is corroborated by the results obtained using intact NPE cells.

Example 5

Reduction of Intraocular Pressure

These experiments examined the effects of topically administered α2β3-selective digoxin derivatives, according to some embodiments of the present invention, DiB, DMcP and DcB, on IOP in rabbits. Due to the lower Ki for inhibition of α2β3, compared to digoxin, and the high hydrophobicity, these compounds were predicted to both permeate the cornea well and efficiently inhibit the α2β3 in the NPE ciliary epithelium, thus reducing inflow of aqueous humour and IOP.

New Zealand white rabbits (3-3.5 kg) about 1 year old, of either sex, were housed in pairs in cage in animal room conditions on a reversed, 12-hour dark/light cycle. For the experiments the animals were transferred to rabbit restrainers in a quiet and calm atmosphere. No ocular abnormalities were detected prior or during the experiments.

IOP measurements were made with a pneumatonometer (Model 30, Reichert technologies) either after raising IOP with 4-aminopyridine (4AP; 1 drop 40 mg/ml), or on basal IOP after addition of one drop of 1 mM solution of digoxin derivatives to the right eye (RE) and one drop of PBS to the left eye (LE) that served as control.

For comparison of effects of digoxin derivatives, such as DcB with a known glaucoma drug Latanoprost, three groups of five rabbits were used. Rabbits treated with Latanoprost, received the medication every day for 5 days before the start of the experiment. On the day of the experiment rabbits were treated at 5 minutes interval with one drop of 1 mM DcB, one drop of 0.005% Latanoprost (Xalatan™, Pfizer) or one drop each of DcB and Latanoprost (RE), or normal saline (LE, Control). IOP was measured every hour for 12 hours (DcB and Latanoprost alone) and after 24 hours (DcB with Latanoprost). Basal IOPs in both eyes, without any medication, were measured 5 days before and on the day of the experiment. All eyes were examined routinely by ophthalmic examinations and were free of any abnormalities. Corneal thickness (μm) was measured using an ultrasonic pachometer (Sonogage pachometer, Cleveland, USA).

Stock solutions of the tested compounds were dissolved in ethanol, and freshly diluted in phosphate buffer (PBS) for each experiment, such that the final ethanol concentration did not exceed 1%.

The first set of experiments examined the effects of the α2-inhibitor compounds, according to embodiments of the present invention, when applied just before 4AP, used as a pharmacological tool to transiently raise IOP. One drop of the tested compound (0.01-0.3 mM) was applied topically to the rabbit's eyes prior to the 4AP, and IOP was then measured over 5 hours.

FIGS. 1A-D present comparative plots of IOP as a function of time, showing the dose response of α2-inhibitor compounds, according to some embodiments of the present invention, in lowering IOP in live rabbits, wherein FIG. 1A shows the results obtained for DiB, FIG. 1B shows the duration of the effect of DiB while 4AP is added to every 2 hours so as to maintain the raised control IOP, FIG. 1C shows the results obtained for DMcP, and FIG. 1D shows the results obtained for DcB.

As can be seen in FIG. 1A, DiB, having Ki α1β1:α2β3 ratio of 16-fold) prevents the rise of the 4AP-induced IOP at concentrations of more than 0.030 mM while at 10 μM it is still effective. As can be seen in FIG. 1B, the duration of the DiB effect was shows that 1 mM DiB is effective for about 8 hours before the IOP begins to rise back up to control levels, which is a significantly long effect.

As can be seen in FIGS. 1B and 1C, DMcP, having a Ki α1β1:α2β3 ratio of 22-fold, and DcB, having a Ki α1β1:α2β3 ratio of 33-fold, exhibit similar IOP reduction as DiB (FIG. 1A), but in even lower concentrations. As can be seen in FIGS. 1B and 1C, low concentrations of 0.01 mM of DMcP or DcB are sufficient to prevent the 4AP-induced rise in IOP.

As can further be seen in FIGS. 1B and 1C, at higher concentrations of 0.1-0.3 mM, the IOP is reduced to levels which are significantly lower than the starting IOP. The latter observation implies that these compounds could reduce basal IOP even in the absence of 4AP.

FIGS. 2A-D present comparative plots of IOP as a function of time, demonstrating the capacity of the α2-inhibitor compounds, according to some embodiments of the present invention, to lower IOP below basal levels compared to a buffer control when administered topically to one eye of a rabbit, while the other eye received PBS as a control, wherein FIG. 2A shows the lack of effect of digoxin, FIG. 2B shows the lack of effect of MB (a non-cyclic moiety inhibitor), FIG. 2C shows the notable of effect of DMcP, and FIG. 2D shows the notable of effect of DcB.

As can be seen in FIG. 2A-B, neither digoxin nor DiB had a significant effect on lowering the basal IOP. This observation coincides with other observations with digoxin or other non-cyclic moiety digoxin derivatives, DMe, DGlyN, the latter two exhibiting enhanced selectivity for $\alpha 2\beta 1$.

As can be seen in FIGS. 2C-D, both DMcP and DcB significantly reduced the basal IOP by 20-25% (about 4 mm Hg for rabbit with a basal IOP of 17 mm Hg) over the test period of 4-5 hours. A higher concentration of DcB (2 mM) reduces the IOP similarly to 1 mM DcB.

This observation indicates that the $\alpha 2$-inhibitor compounds, according to some embodiments of the present invention, can be used effectively to treat medical conditions where there in a need to lower IOP below what is co considered to be a normal pressure, such as cases of low-tension glaucoma and normal-tension glaucoma.

A final set of experiments compared the effectiveness and duration of the effects of topical administration of DcB on basal IOP, with those of a widely used anti-glaucoma drug, Latanoprost, applied either alone or in combination (co-administration).

Groups of 5 rabbits were treated once a day for 5 days with Latanoprost and on the sixth day with DcB, Latanoprost, or DcB/Latanoprost combination. IOP measurements were made for the next 12 hours or over 24 hours for the group treated with both DcB and Latanoprost.

FIGS. 3A-C present comparative plots of IOP as a function of time, demonstrating the effect of $\alpha 2$-inhibitor compounds, according to some embodiments of the present invention, to potentiate the drug Latanoprost in lowering IOP below basal levels, wherein FIG. 3A shows the effect of DcB alone, FIG. 3B shows the effect of Latanoprost alone, and FIG. 3C shows the effect of co-administering DcB with Latanoprost.

As can be seen in FIGS. 3A-C, compared to the basal IOP values of 17-18 mmHg, after 3-8 hours the steady-state IOP was lower by 3.5±0.15, 2.6±0.11 and 3.44±0.39 mmHg with DcB, Latanoprost and DcB/Latanoprost, respectively, corresponding to steady-state IOP's of 75-80%, 85% and 75-80% of the unchanged control values.

As can further be seen in FIGS. 3A-C, DcB, $\alpha 2$-inhibitor compound according to some embodiments of the present invention, was about 25% more effective than Latanoprost in reducing the basal (normal) levels of IOP.

The combination of DcB and Latanoprost was similar in effect to DcB alone; however, with respect to the duration of the effect, for either DcB and Latanoprost, applied alone, the IOP returned to the control (normal) value after 12 hours, but with the combined DcB/Latanoprost treatment the low IOP was maintained for a significantly longer period and it returned to the control value only after 24 hours.

Latanoprost was applied for 5 days prior to the day of measurement, due to reports that this pre-treatment produces optimal effects on IOP in humans, although in these experiments with rabbits it seems that this was unnecessary since the effects of Latanoprost were observed acutely and had dissipated completely after 24 hours.

The animals which received the treatment presented in FIGS. 3A-C were used for corneal thickness measurements after topically administering drops of DcB or Latanoprost to 4 rabbits once a day for 5 additional days, totaling 6 days of treatment with DcB or Latanoprost, and the results are presented in Table 4 below.

TABLE 4

| Rabbit | Treatment to RE | Pachymetry (mm) RE | LE |
|---|---|---|---|
| 1 | DcB | 455 | 456 |
| 2 | DcB | 480 | 456 |
| 3 | DcB | 400 | 396 |
| 4 | DcB | 382 | 374 |
| 5 | Latanoprost | 467 | 471 |
| 6 | Latanoprost | 489 | 498 |

As seen in Table 4, there was no detectable effect of either drug on corneal thickness. In addition, by inspection, no significant redness or ocular irritation was observed.

In order to assess whether topical application of DcB damaged the tissues of the eye including cornea, iris, lens, cilary body, retina, choroid and sclera, a histological examination was conducted after topical application, using one drop of 1 mM DcB daily for one week in one eye of each animal, with the other eye treated topically with one drop of PBS and serving as the control. Animals were sacrificed, eyes were removed, fixed in 10% neutral buffered formalin, processed routinely for histological examination, trimmed at 4 μm, and stained with hematoxylin and eosin. No significant histological differences were observed in a comparative analysis of the treated and untreated eyes, indicating that topical treatment with DcB for a week does not cause tissue damage in the eye.

Example 6

Prodrug Synthesis and Characterization

Prodrugs of the compounds presented herein were developed in order to improve the pharmacokinetic profile of the active compounds, e.g., to avoid potential toxic effects in the cornea. The synthetic strategy included preparation of substantially inactive derivatives of the compounds, which are ineffective as an inhibitor of the major isoform of the Na,K-ATPase in the cornea (mainly the $\alpha 1\beta 1$ isoform), and which can penetrate into the eye and thereafter are converted into the active form by biodegradation processes. The biodegraded and active form of the prodrug can then inhibits the $\alpha 2\beta /3$ complex in the ciliary NPE cells and reduces inflow of aqueous humor.

Synthesis:

The synthesis of an exemplary prodrug compound, according to some embodiments of the present invention, 3',3"-bisacetyl digoxin cyclobutane (bisAcDcB), from an exemplary compound according to some embodiments of the present invention, DcB, is illustrated in Scheme 2 below.

Scheme 2

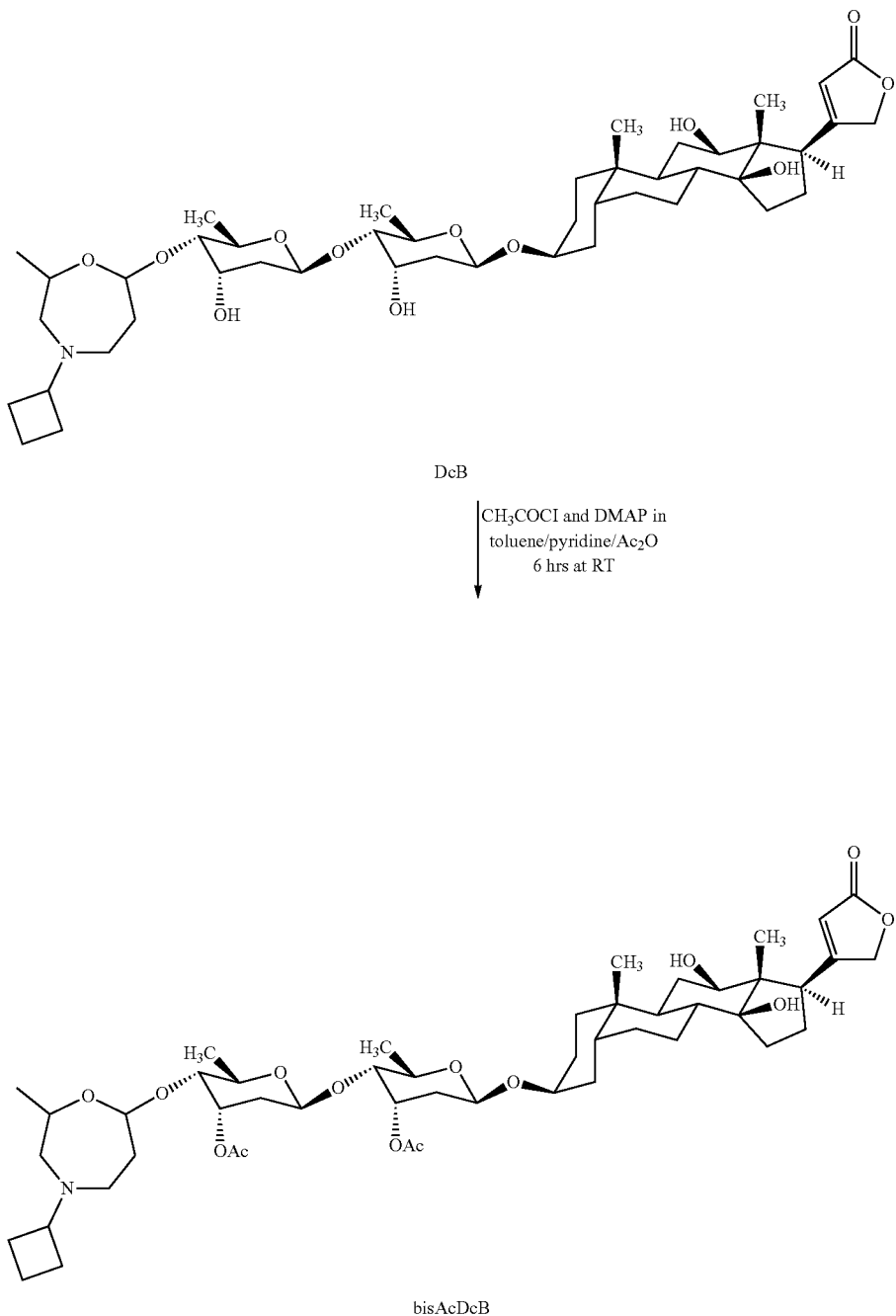

In this example, the bisacetyl derivative (IUPAC name (2R,3R,4S,6R)-3-(((2S,4S,5R,6R)-4-acetoxy-5-((4-cyclobutyl-2-methyl-1,4-oxazepan-7-yl)oxy)-6-methyltetrahydro-2H-pyran-2-yl)oxy)-6-(((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)oxy)-2-methyltetrahydro-2H-pyran-4-yl acetate) was afforded by stirring for 6 hours at room temperature a solution of DcB (10 mg, 12.3 μmol, MW=817) and 4-dimethylaminopyridine (DMAP) catalyst (0.3 mg, 2.4 μmol, MW=122) in 2 ml toluene, 2 ml pyridine and 0.7 ml acetic anhydride.

Thereafter, the resulting mixture, rich in the bis-acetylated derivative, was extracted with water and dichloromethane, and subjected to final wash with HCl-acidified water pH of about 4. The resulting residue was dried over $MgSO_4$, and purified in normal phase HPLC, using a silica gel column.

The synthesis of an exemplary prodrug compound, according to some embodiments of the present invention, 12,3',3''-trisacetyl digoxin cyclobutane (trisAcDcB), from an exemplary compound according to some embodiments of the present invention, DcB, is illustrated in Scheme 3 below.

Scheme 3

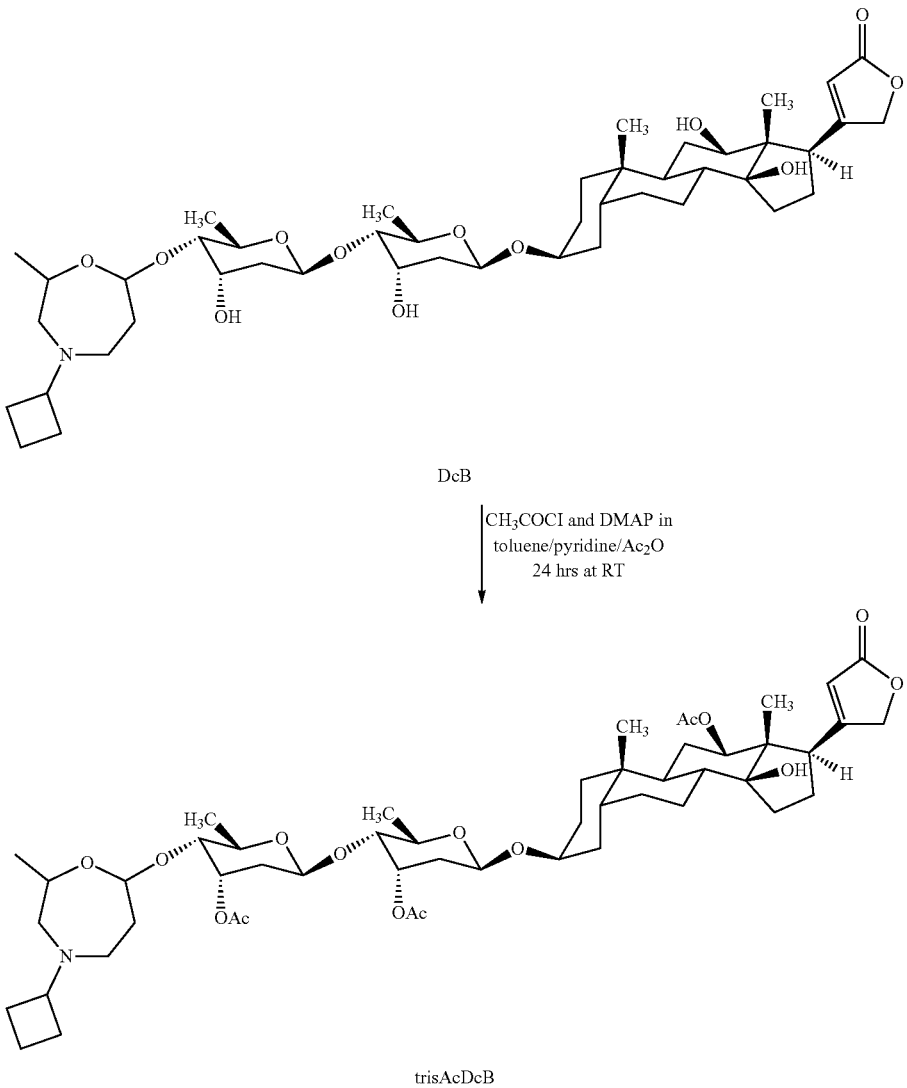

In this example, the trisacetyl derivative (IUPAC name (2R,3R,4S,6R)-6-(((3S,5R,8R,9S,10S,12R,13S,14S,17R)-12-acetoxy-14-hydroxy-10,13-dimethyl-17-(5-oxo-2,5-dihydrofuran-3-yl)hexadecahydro-1H-cyclopenta[a]phenanthren-3-yl)oxy)-3-(((2S,4S,5R,6R)-4-acetoxy-5-((4-cyclobutyl-2-methyl-1,4-oxazepam-7-yl)oxy)-6-methyltetrahydro-2H-pyran-2-yl)oxy)-2-methyltetrahydro-2H-pyran-4-yl acetate) was afforded by stirring for 24 hours at room temperature a solution of DcB3 (10 mg, 12.3 µmol, MW=817) and 4-dimethylaminopyridine (DMAP) catalyst (0.3 mg, 2.4 µmol, MW=122) in 2 ml toluene, 2 ml pyridine and 0.7 ml acetic anhydride.

Thereafter, the resulting mixture, rich in the tris-acetylated derivative, was extracted with water and dichloromethane, and subjected to final wash with HCl-acidified water pH of about 4. The resulting residue was dried over $MgSO_4$, and purified in normal phase HPLC using a silica gel column.

Calculated octanol-water partition coefficient (CLogP) for DcB is 3.43, for a mono-acetyl derivative of DcB is 3.93, for the bisAcDcB derivative is 4.37, and for the trisAcDcB derivative is 4.85 (CLogP software ALOGPS 2.1 [Tetko, I. V. et al., *J. Chem. Inf. Comput. Sci.*, 2002, 42, 1136-45])

In Vitro Inhibition Activity:

The results of the inhibition assay of purified human Na,K-ATPase (α1β1FXYD1 and α2β1FXYD1) by DcB, bisAcDcB and trisAcDcB are presented as Ki values in Table 5 below.

TABLE 5

| Compound | Ki of α1β1FXYD1 [nM] | Ki of α2β1FXYD1 [nM] |
|---|---|---|
| DcB | 135 ± 11 | 8 ± 1.25 |
| BisAcDcB | 1180 ± 280 | 395 ± 50 |
| TrisAcDcB | 13200 ± 6500 | 2500 ± 490 |

As can be seen in Table 5, the Ki values of α1β1 by the exemplary bisAcDcB prodrug derivative and the exemplary trisAcDcB prodrug derivative are about 9-fold and 100-fold higher than that observed for the corresponding exemplary compound DcB, respectively, while the Ki values of α2β1 by bisAcDcB and trisAcDcB are about 50-fold and 300-fold higher than that observed for the corresponding DcB, respectively.

In Vivo Activity—Lowering of basal IOP:

One 30 μl drop of trisAcDcB or vehicle was applied to the right or left eye of two rabbits, respectively, at 0.05, 0.1, and 0.2 mM concentrations. The IOP was then measured every 1-2 hours over 12 hours.

Figure 4:
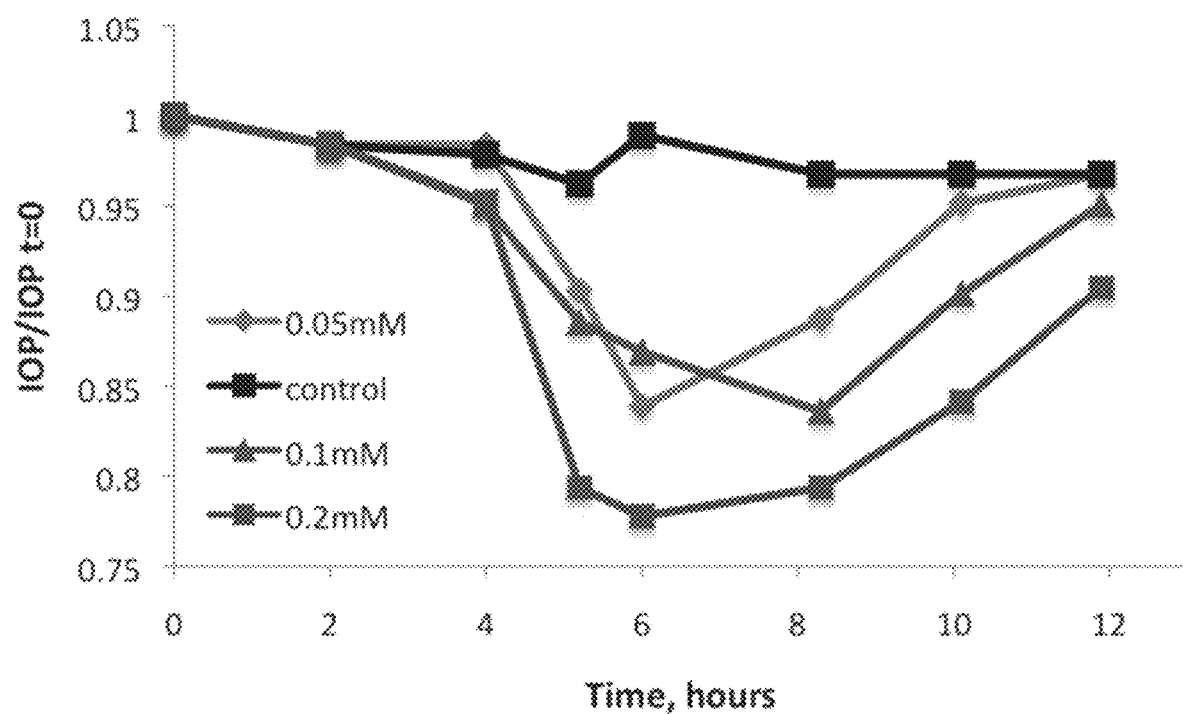
FIG. 4 presents comparative plots of IOP as a function of time, demonstrating the capacity of the trisAcDcB prodrug of the α2-inhibitor compound DcB, according to some embodiments of the present invention, to lower IOP below basal levels compared to a buffer control when administered topically to one eye of a rabbit, while the other eye received PBS as a control.

FIG. 4 presents comparative plots of IOP as a function of time, demonstrating the capacity of the trisAcDcB prodrug of the α2-inhibitor compound DcB, according to some embodiments of the present invention, to lower IOP below basal levels compared to a buffer control when administered topically to one eye of a rabbit, while the other eye received PBS as a control.

As can be seen in FIG. 4, no effect was observed at the first four hours, and after that the IOP in the drug-treated samples dropped from 15-16 mmHg to a minimum of 12 mmHg within 5-6 hours, before returning to the control level after 12 hours. In addition, the maximal effect of the trisAcDcB on TOP was essentially equal to that produced by the parent DcB (see, for example, FIG. 2D). The comparison with the parent DcB compound shows that significantly lower doses of the prodrug are required to produce the maximal effect.

Thus, it can be concluded that acetyl prodrugs of the compounds presented herein exhibit low affinity and weak inhibition of α1β1 isoform, which is the major isoform in the cornea, making it unlikely that topical application of the prodrug in human eye would cause corneal swelling or other toxic adverse effects. The lag of four hours prior to a detectable effect of the prodrug suggests that this time is required for the intra-ocular esterases to hydrolyze the acetyl groups and regenerate DcB within the to anterior chamber of the eye. Moreover, significantly lower doses of prodrug are required to achieve a comparable effect of the parent compound. This finding is consistent with a higher permeability through the cornea compared to DcB (ClogP 3.43) due to a higher lipophilicity of the esters (triAcDcB ClogP 4.85).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A compound represented by general Formula I:

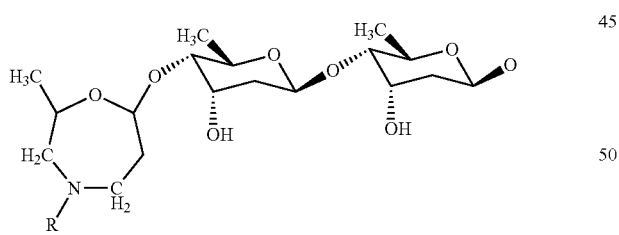
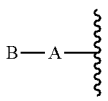
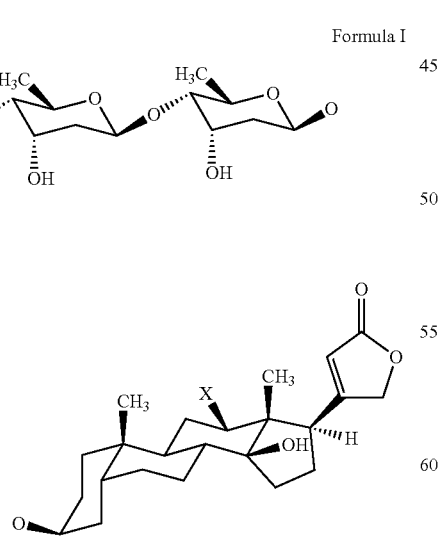

including any pharmaceutically acceptable salt, hydrate, solvate, enantiomer and diastereomer thereof, and any mixtures thereof, wherein:

X is H or OH;

R is represented by general Formula II:

A is $-CH_2-$, $-(CH_2)_2-$ or a covalent bond; and

B is a cyclic moiety selected from the group consisting of an unsubstituted alicyclic moiety, a substituted alicyclic moiety, an unsubstituted heterocyclic moiety, a substituted heterocyclic moiety, an unsubstituted heteroaryl moiety and a substituted heteroaryl moiety;

or

B is selected from the group consisting of an alkylsulfonyl, an arylsulfonyl and a sulfonamide;

or

B is $-N_1R_2$, wherein $R_1$ and $R_2$ are each independently H or a $C_1$-$C_4$ alkyl provided that at least one of $R_1$ and $R_2$ is a $C_1$-$C_4$ alkyl.

2. The compound of claim 1, wherein A is selected from the group consisting of a covalent bond, an unsubstituted $C_1$-$C_6$ alkyl, a substituted $C_1$-$C_6$ alkyl, an unsubstituted $C_1$-$C_6$ alkyl interrupted by one or more heteroatom and a substituted $C_1$-$C_6$ alkyl interrupted by one or more heteroatom.

3. The compound of claim 1, wherein said unsubstituted alicyclic moiety is selected from the group consisting of cyclopropyl, cyclobutyl, cyclopentyl, cyclohexyl and cycloheptyl.

4. The compound of claim 1, wherein said unsubstituted heteroaryl moiety is imidazolyl.

5. The compound of claim 1, wherein said alkylsulfonyl is selected from the group consisting of methylsulfonyl, ethylsulfonyl and isopropylsulfonyl.

6. The compound of claim 1, wherein said arylsulfonyl is selected from the group consisting of phenylsulfonyl, benzylsulfonyl and tosyl.

7. The compound of claim 1, wherein said sulfonamide is selected from the group consisting of methylsulfonamide, N-methylmethanesulfonamide and N,N-dimethylmethanesulfonamide.

8. The compound of claim 1, wherein B is —N(Et)$_2$.

9. The compound of claim 1, wherein R is selected from the group consisting of cyclopropyl, methylcyclopropane, ethylcyclopropane, propylcyclopropane, cyclobutyl, methylcyclobutane, methyl-3,3-dimethylcyclobutane, ethylcyclobutane, propylcyclobutane, cyclopentyl, methylcyclopentane, ethylcyclopentane, propylcyclopentane, cyclohexyl, azetidinyl, oxetanyl, thietanyl, histaminyl and benzyl.

10. The compound of claim 1, having an affinity to at least one isoform of Na,K-ATPase, wherein said isoform is selected from the group consisting of α1β1, α1β2, α1β3, α2β1, α2β2, α2β3, α3β1, α3β2, α3β3, α4β1, α4β2 and α4β3.

11. The compound of claim 10, wherein said affinity to any one of α2β1, α2β2 and α2β3 is higher than the affinity to α1β1, α1β2, α1β3, α3β1, α3β2, α3β3, α4β1, α4β2 and α4β3 by at least 100%.

12. A pharmaceutical composition comprising as an active ingredient a compound of claim 1 and a pharmaceutically acceptable carrier.

13. A method of reducing intraocular pressure (TOP) in a subject in need thereof, comprising administering to the subject a therapeutically effective amount of a compound of claim 1.

14. A method of treating a heart condition in a subject in need thereof, comprising administering to the subject a therapeutically effective amount of a compound of claim 1.

15. A pharmaceutical composition comprising as active ingredients:

at least one ingredient selected from the group consisting of a prostaglandin analog, a β-blocker, an adrenergic agent, an α2-adrenergic receptor agonist, a miotic agent, a carbonic anhydrase inhibitor and a cholinergic agonist; and a compound represented by Formula III:

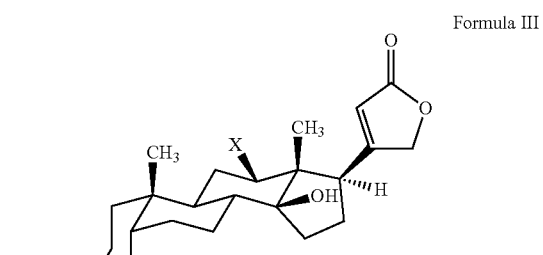

Formula III

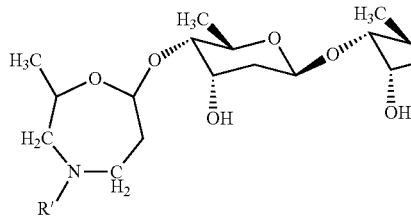

including any pharmaceutically acceptable salt, hydrate, solvate, enantiomer and diastereomer thereof, and any mixtures thereof, and a pharmaceutically acceptable carrier, wherein:

X is H or OH;

R' is represented by general Formula II:

Formula II

A is —CH$_2$—, —(CH$_2$)$_2$— or a covalent bond; and

B is a cyclic moiety selected from the group consisting of an unsubstituted alicyclic moiety, a substituted alicyclic moiety, an unsubstituted heterocyclic moiety, a substituted heterocyclic moiety, an unsubstituted heteroaryl moiety and a substituted heteroaryl moiety, or B is selected from the group consisting of an alkylsulfonyl, an arylsulfonyl and a sulfonamide, or B is —N$_1$R$_2$, wherein R$_1$ and R$_2$ are each independently H or a C$_1$-C$_4$ alkyl provided that at least one of R$_1$ and R$_2$ is a C$_1$-C$_4$ alkyl, and a pharmaceutically acceptable carrier.

16. The pharmaceutical composition of claim 15, being packaged in a packaging material and identified in print, or on said packaging material, for use in reducing intraocular pressure (TOP).

17. A method of treating a heart condition in a subject in need thereof, comprising co-administering to the subject a therapeutically effective amount of:

an agent selected from the group consisting of a β-blocker, an anticoagulation agent, an angiotensin-converting-enzyme inhibitor and an angiotensin II receptor antagonist; and a compound represented by Formula III:

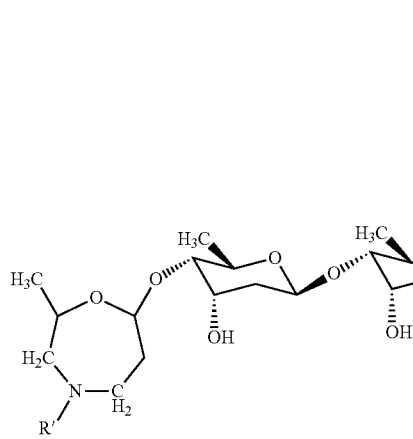
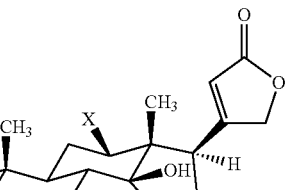

Formula III including any pharmaceutically acceptable salt, hydrate, solvate, enantiomer and diastereomer thereof, and any mixtures thereof,
wherein:
X is H or OH;
R' is represented by general Formula II:

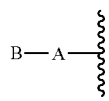

Formula II

A is a spacer moiety or a covalent bond; and

B is a cyclic moiety, or B is selected from the group consisting of an alkylsulfonyl, an arylsulfonyl and a sulfonamide, or B is —$N_1R_2$, wherein $R_1$ and $R_2$ are each independently H or a $C_1$-$C_4$ alkyl provided that at least one of $R_1$ and $R_2$ is a $C_1$-$C_4$ alkyl.

* * * * *